(12) United States Patent
Fujioka et al.

(10) Patent No.: US 8,653,234 B2
(45) Date of Patent: Feb. 18, 2014

(54) PEPTIDE VACCINES FOR CANCERS EXPRESSING MPHOSPH1 OR DEPDC1 POLYPEPTIDES

(75) Inventors: Tomoaki Fujioka, Morioka (JP); Yusuke Nakamura, Bunkyo-ku (JP); Takuya Tsunoda, Bunkyo-ku (JP); Ryuji Osawa, Kawasaki (JP); Midori Shida, Kawasaki (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 13/535,303

(22) Filed: Jun. 27, 2012

(65) Prior Publication Data

US 2012/0282286 A1     Nov. 8, 2012

Related U.S. Application Data

(62) Division of application No. 12/445,729, filed as application No. PCT/JP2007/001122 on Oct. 16, 2007.

(60) Provisional application No. 60/852,575, filed on Oct. 17, 2006.

(51) Int. Cl.
  *C07K 5/00* (2006.01)
  *C12N 15/00* (2006.01)

(52) U.S. Cl.
  USPC .......................... 530/300; 435/69.3; 435/70.1

(58) Field of Classification Search
  None
  See application file for complete search history.

(56) References Cited

U.S. PATENT DOCUMENTS

| | | | |
|---|---|---|---|
| 5,707,626 A | 1/1998 | Douvas et al. | |
| 6,294,663 B1 | 9/2001 | O'Brien et al. | |
| 7,001,999 B1 | 2/2006 | Martelange et al. | |
| 7,030,215 B2 | 4/2006 | Liu et al. | |
| 7,078,217 B2 | 7/2006 | Corcoran et al. | |
| 7,745,391 B2 | 6/2010 | Mintz et al. | |
| 7,919,467 B2 | 4/2011 | Ramakrishna et al. | |
| 2003/0068675 A1 | 4/2003 | Liu | |
| 2004/0241726 A1 | 12/2004 | Liew | |
| 2006/0024692 A1 | 2/2006 | Nakamura et al. | |
| 2007/0099251 A1 | 5/2007 | Zhang et al. | |
| 2008/0207497 A1 | 8/2008 | Ramakrishna | |
| 2009/0175844 A1 | 7/2009 | Nakamura et al. | |
| 2009/0317392 A1 | 12/2009 | Nakamura et al. | |
| 2011/0237518 A1 | 9/2011 | Nakamura et al. | |
| 2012/0014996 A1 | 1/2012 | Nakamura et al. | |

FOREIGN PATENT DOCUMENTS

| JP | 2008/532477 A | 8/2008 |
|---|---|---|
| RU | 94/038427 A1 | 2/1994 |
| WO | 93/03764 A1 | 3/1993 |
| WO | WO 00/73801 A2 | 12/2000 |
| WO | WO0216593 * | 2/2002 |
| WO | WO 02/31111 A2 | 4/2002 |
| WO | WO 02/46416 A2 | 6/2002 |
| WO | WO 03/040165 A2 | 5/2003 |
| WO | WO 03/083074 A2 | 10/2003 |
| WO | WO 2004/031413 A2 | 4/2004 |
| WO | WO 2004/112589 A2 | 12/2004 |
| WO | WO2005007090 * | 1/2005 |
| WO | 2006/085684 A2 | 8/2006 |
| WO | WO 2006/085684 A2 | 8/2006 |
| WO | WO 2007/013665 A2 | 2/2007 |
| WO | WO2007150077 * | 12/2007 |

OTHER PUBLICATIONS

Harig et al, Blood, vol. 98, p. 2999-3005, 2001.*
Akiyoshi, "Current Cancer Vaccine Therapy Research,—Trials Using Peptide Derived from Tumor-Rejection Antigen-" *Gan To Kagakuryouhou*, vol. 24(5), pp. 511-519 (1997).
Akiyoshi, "Vaccine therapy using MAGE antigenic peptides," *Igaku No Ayumi*, vol. 190(2), pp. 139-142 (1999).
Falk, et al., "Allele-specific motifs revealed by sequencing of self-peptide eluted from MHC molecules," *Nature*, vol. 351(6324), pp. 290-296 (May 23, 1991).
Rammensee, et al., "MHC ligands and peptide motifs: first listing," *Immunogenetics*, vol. 41(4), pp. 178-228 (1995).
Yamaue, "Cancer Immunotherapy using CEA antigenic peptides," *Igaku No Ayumi*, vol. 190(2), pp. 135-138 (1999).
Harada, et al., "Investigation of a novel potential therapeutic modality targeting to DEPDC1 for bladder cancer," *Abstract of Annual Meeting of the Japanese Cancer Association*, 68: 219, O-338 (2009).
Ota, et al., "Complete sequencing and characterization of 21,243 full-length human cDNAs," *Nat Genet.*, vol. 36(1), pp. 40-45 (Jan. 2004, Epub Dec. 21, 2003).
NCBI GenBank Accession No. NM_017779, 3 pages, (Oct. 28, 2004).
U.S. Appl. No. 13/536,327, filed Jun. 28, 2012, 204 pages.
Abaza, A., et al., "M Phase Phosphoprotein 1 Is a Human Plus-end-directed Kinesin-related Protein Required for Cytokinesis," *The Journal of Biological Chemistry*, vol. 278(30), pp. 27844-27852 (Jul. 25, 2003, Epub May 11, 2003).
Dionne, S., et al., "Functional characterization of CTL against gp100 altered peptide ligands," *Cancer Immunol. Immunother.*, vol. 52(4), pp. 199-206 (Apr. 2003, Epub Feb. 18, 2003).

(Continued)

*Primary Examiner* — Lei Yao
(74) *Attorney, Agent, or Firm* — Kilpatrick Townsend & Stockton LLP

(57) ABSTRACT

The present invention provides peptides having an amino acid sequence as set forth in SEQ ID NO: 7, 8, 9, 10, 11, 12, 192, 195, 197, 209, 225, 226, 228, 230, 240, 241, 243, 244, 249, 253, 254 or 255, as well as peptides having the above-mentioned amino acid sequences in which 1, 2, or several amino acids are substituted, deleted, or added, wherein the peptides possess cytotoxic T cell inducibility. The present invention also provides drugs for treating or preventing a disease associated with the over-expression of MPHOSPH1 and/or DEPDC1, e.g. cancers, containing these peptides as an active ingredient. The peptides of the present invention can also be used as vaccines.

4 Claims, 26 Drawing Sheets

(56) References Cited

OTHER PUBLICATIONS

Dionne, S., et al., Her-2/*neu* altered peptide ligand-induced CTL responses: implications for peptides with increased HLA affinity and T-cell-receptor interaction, *Cancer Immunol. Immunother.*, vol. 53(4), pp. 307-314 (Apr. 2004, Epub Nov. 5, 2003).

Ferries, E., et al., "Identification of p53 Peptides Recognized by CD8+ T Lymphocytes From Patients With Bladder Cancer," *Human Immunology*, vol. 62(8), pp. 791-798 (Aug. 2001).

Greenbaum, D., et al., "Interrelating Different Types of Genomic Data, from Proteome to Secretome: 'Oming in on Function," *Genome Research*, vol. 11(9), pp. 1463-1468 (Sep. 2001).

Greenbaum, D., et al., "Comparing protein abundance and mRNA expression levels on a genomic scale," *Genome Biology*, vol. 4(9), pp. 117.1-117.8 (2003, Epub Aug. 29, 2003).

Hoffmann, T., et al., "The Ability of Variant Peptides to Reverse the Nonresponsiveness of T Lymphocytes to the Wild-Type Sequence $p53_{264-272}$ Epitope," *J. Immunol.*, vol. 168(3), pp. 1338-1347 (Feb. 1, 2002).

Ito, K., et al., "Identification of Bladder Cancer Antigens Recognized by IgG Antibodies of a Patient with Metastatic Bladder Cancer," *Int. J. Cancer*, vol. 108(5), pp. 712-724 (Feb. 20, 2004).

Kanehira, et al., "BT-A1 involved in human bladder carcinogenesis and its possibility of therapeutic target against bladder cancers," *Proceedings, Sixty-Fifth Annual Meeting of the Japanese Cancer Association*, p. 436(#0-666) (Aug. 28, 2006).

Kanehira, M., et al., "Involvement of upregulation of DEPDC1 (DEP domain containing 1) in bladder carcinogenesis," *Oncogene*, vol. 26(44), pp. 6448-6455 (Sep. 27, 2007, Epub Apr. 23, 2007).

Kanehira, M., et al., "Oncogenic Role of MPHOSPH1, a Cancer-Testis Antigen Specific to Human Bladder Cancer," *Proceedings, 66th Annual Meeting of the Japanese Cancer Association*, p. 474(#P-1008) (Aug. 25, 2007).

Komori, H., et al., "Identification of HLA-A2- or HLA-A24-Restricted CTL Epitopes Possibly Useful for Glypican-3-Specific Immunotherapy of Hepatocellular Carcinoma," *Clin. Cancer Res.*, vol. 12(9), pp. 2689-2697 (May 1, 2006).

Kondo, A., et al., "Prominent Roles of Secondary Anchor Residues in Peptide Binding to HLA-A24 Human Class 1 Molecules," *J. Immunol.*, vol. 155(9), pp. 4307-4312 (Nov. 1, 1995).

Kubo, R., et al., "Definition of Specific Peptide Motifs for Four Major HLA-A Alleles," *J. Immunol.*, vol. 152(8), pp. 3913-3924 (Apr. 15, 1994).

Lu, P., et al., "siRNA-mediated antitumorigenesis for drug target validation and therapeutics," *Curr. Opin. Mol. Ther.*, vol. 5(3), pp. 225-234 (Jun. 2003).

Lutgendorf, S., et al., "Diurnal Cortisol Variations and Symptoms in Patients with Interstitial Cystitis," *The Journal of Urology*, vol. 167(3), pp. 1338-1343 (Mar. 2002).

Marri, *Biochemistry of Human*, vol. 1, p. 34, 6 pgs., MIR Publishing House (1993).

Sanchez-Carbayo, M., et al., "Recent advances in bladder cancer diagnostics," *Clin. Biochem.*, vol. 37(7), pp. 562-571 (Jul. 2004).

Tang, Y., et al., "FLJ20354 fis clone HEP15013," Accession No. ABP43909, 2 pgs. (Oct. 12, 2000).

Uchida, N., et al., "Ring Finger Protein 43 as a New Target for Cancer Immunotherapy," *Clin. Cancer. Res.*, vol. 10(24), pp. 8577-8586 (Dec. 15, 2004).

Zaremba, S., et al., "Identification of an Enhancer Agonist Cytotoxic T Lymphocyte Peptide from Human Carcinoembryonic Antigen," *Cancer Research*, vol. 57(20), pp. 4570-4577 (Oct. 15, 1997).

Kangawa, et al., "Neuromedin K: A novel mammalian tachykinin identified in porcine spinal cord," *Biochem Biophys Res Commun.*, vol. 114(2), pp. 533-540 (Jul. 29, 1983).

Adams, et al., "Prediction of binding to MHC class I molecules," *J Immunol Methods*, vol. 185(2), pp. 181-190.

Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (Oct. 15, 2002).

Boon, "Tumor Antigens Recognized by Cytolytic T Lymphocytes: Present Perspectives for Specific Immunotherapy," *Int J Cancer*, vol. 54(2), pp. 177-180 (May 8, 1993).

Boon, et al., "Human Tumor Antigens Recognized by T Lymphocytes," *J Exp Med.*, vol. 183(3), pp. 725-729. (Mar. 1, 1996).

Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999)

Coulie, et al, "Cytolytic T-cell responses of cancer patients vaccinated with a MAGE antigen," Immunol Rev., vol. 188, pp. 33-42 (Oct. 2002).

Fujie, et al., "A Mage-1 Encoded HLA-A24-Binding Synthetic Peptide Induces Specific Anti-Tumer Cytotoxic T Lymphocytes," *Int J Cancer*, vol. 80(2), pp. 169-172 (Jan. 18, 1999).

Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).

Kikuchi, et al., "Identification of a SART-1-Derived Peptide Capable of Inducing HLA-A24-Restricted and Tumor-Specific Cytotoxic T Lymphocytes," *Int J Cancer*, vol. 81(3), pp. 459-466 (May 5, 1999).

Oiso, et al., "A Newly Identified *Mage*-3-Derived Epitope Recognized by HLA-A24-Restricted Cytotoxic T Lymphocytes," *Int J Cancer*, vol. 81(3), pp. 387-394 (May 5, 1999).

Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).

Rosenberg, et al., "Cancer immunotherapy: moving beyond current vaccines," *Nat Med.*, vol. 10(9), pp. 909-915 (Sep. 2004).

Schueler-Furman, et al., "Structure-based prediction of binding peptides to MHC class I molecules: Application to a broad range of MHC alleles," *Protein Sci.*, vol. 9(9), pp. 1838-1846 (Sep. 2000).

Tanaka, et al., "Induction of Antitumor Cytotoxic T Lymphocytes with a MAGE-3-encoded Synthetic Peptide Presented by Human Leukocytes Antigen-A24," *Cancer Res.* vol. 57(20), pp. 4465-4468. (Oct. 15, 1997).

Van Der Burg, et al., "Immunogenicity of Peptides Bound to MHC Class I Molecules Depends on the MHC-Peptide Complex Stability" *J Immunol.*, vol. 156(9), pp. 3308-3314 (May 1, 1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.* vol. 59(21), pp. 5554-5559 (Nov. 1, 1999).

Alderson, et al., Geneseq Accession No. AAW73850 Mar. 24, 1999 "M. Tuberculosis antigen clone peptide MSF-15," 1 pg.

Barnea, et al., Geneseq Accession No ABJ20188 Apr. 10, 2003 "MHC binding peptide SEQ ID No 353," 1 pg.

Blenis, et al., Geneseq Accession No. ADW77950 Apr. 7, 2005 "Human cancer therapy target peptide 8216989," 2 pgs.

Carr, et al., Geneseq Accession No. ABG97886 Jan. 7, 2005 "Human INFbeta peptide #8 with potential MHC class II abinding activity," 1 pg.

Gao, et al., Geneseq Accession No. ADY66992 Jun. 2, 2005 "Skin tissue-specific homing peptide—SEQ ID 231," 1 pg.

Gygi, et al., Geneseq Accession No. ABU64153 Mar. 11, 2004 "Protein detection and quantification method peptide #34," 1 pg.

Hashimoto, et al., Geneseq Accession No. AAY14496 Aug. 31, 1999 "Antigenic peptide !1 from human cytochrome p450 1A1 protein," 1 pg.

Haynes, et al., Geneseq Accession No. ABG96076 Dec. 11, 2002 "Cysteine-containing peptide isolated by the invention method, #49," 2 pgs.

Hutchison, Geneseq Accession No. ABG76369 May 10, 2003 "Mutant peptide #6 derived from human parathyroid hormone (hPTH)," 1 pg.

Imperiali, et al., Geneseq Accession No. ADA09065 Nov. 6, 2003 "Lanthanide binding peptide #5," 2 pgs.

Kanehira, et al., *Cancer Res.* Apr. 1, 2007;67(7):3276-85.

Mao, et al., Geneseq Accession No. ABB05654 Apr. 29, 2002 "Human DNA binding protein RFX2-89 N-terminal peptide SED ID NO: 7," 1 pg.

Mao, et al., Geneseq Accession No. AAG79565 Dec. 23, 2002 "hAQP 14-74 N-terminal fragment," 1 pg.

(56) References Cited

OTHER PUBLICATIONS

Mao, et al., Geneseq Accession No. ABB75689 Jun. 17, 2002 "Human follicle induced axial formation protein 9 peptide fragment," 1 pg.

Rammensee, et al., Geneseq Accession No AEG71129 Jun. 1, 2006 "Huyman tumor associated T-helper cell peptide epitope SEQ ID 320," 1 pg.

Roberts, et al., Geneseq Accession No. AAM43011 Oct. 22, 2001 "Mycoplasma genitalium intermolecular complementary peptide, SEQ ID 320,"1 pg.

Roberts, et al., Geneseq Accession No. AAG85912 Sep. 11, 2001 "Saccharomyces cerevisiae peptide, SEQ ID NO: 861," 1 pg.

Schartz, et al., *Curr Opin Mol Ther*. Aug. 2002;4(4):372-81.

Shaw, et al., Geneseq Accession No. ABP75331 Feb. 20, 2003 "Chlamydia pneumonia peptide epitope #97," 1 pg.

Shimkets, et al., Geneseq Accession No. AAM98054 Jan. 24, 2002 "Human peptide #1329 encoded by a SNP oligonucleotide," 1 pg.

Shimkets, et al., Geneseq Accession No. AAM00429 Oct. 1, 2001 "Human protein fragment SEQ ID NO: 977," 1 pg.

Uger, et al., Geneseq Accession No ADB39054 Dec. 4, 2003 "Human tumour derived peptide Tyr 171," 2 pgs.

Yuen, et al., Geneseq Accession No. AEG37435 May 4, 2006 "CoC-HKU1 peptide fragment #748," 2 pgs.

\* cited by examiner

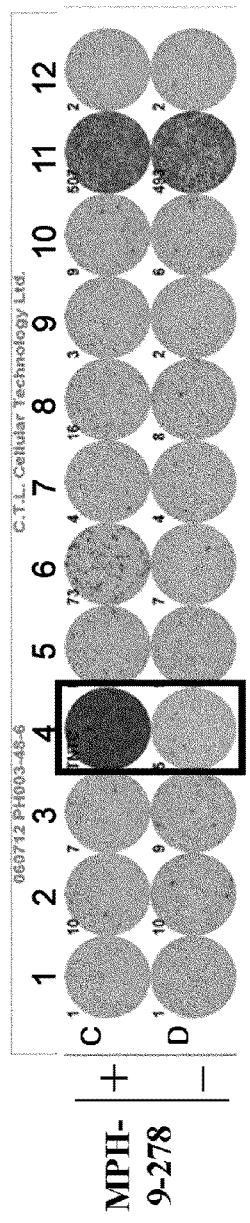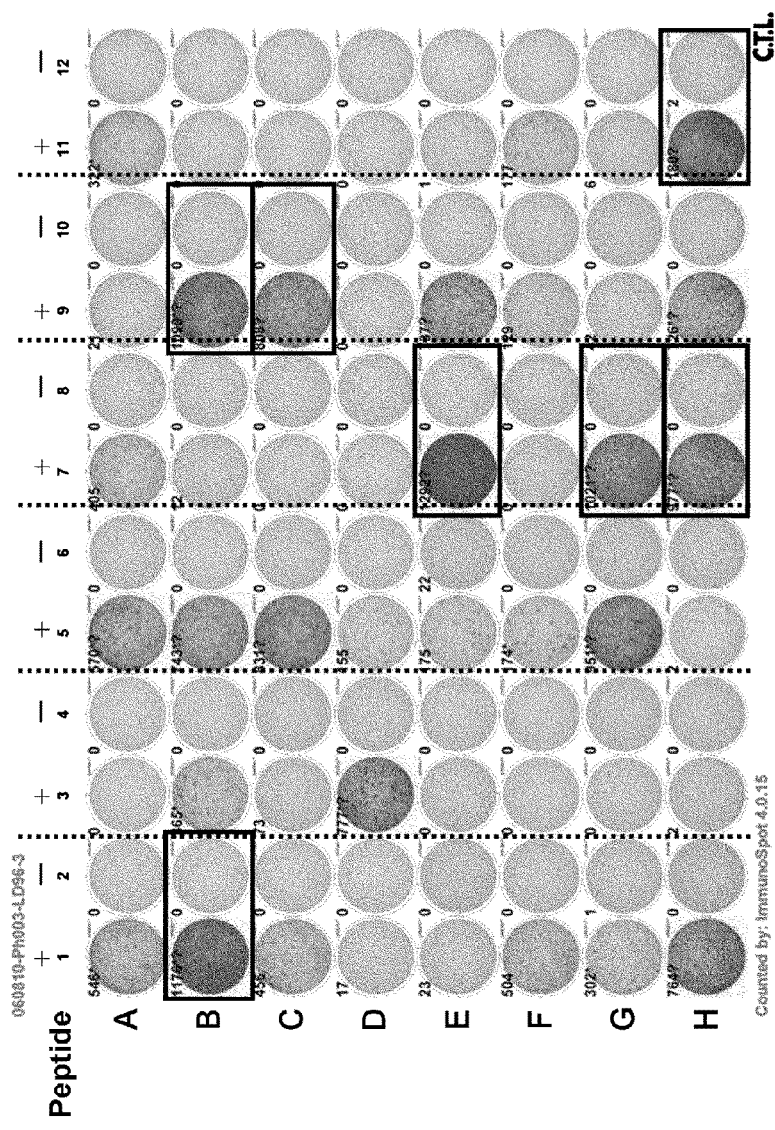
FIG. 1A
FIG. 1B

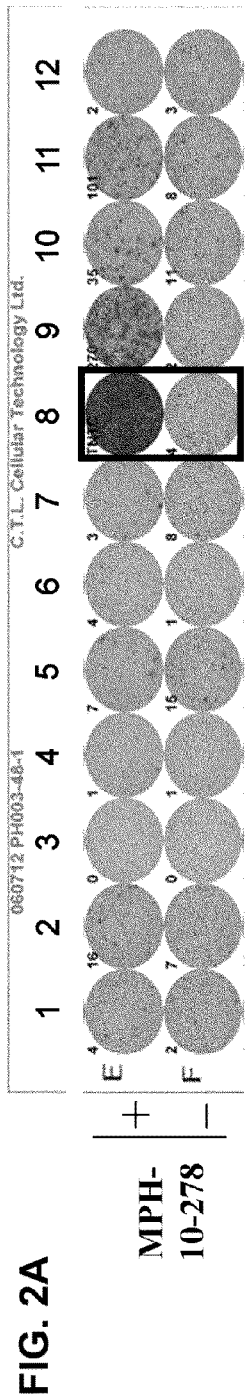
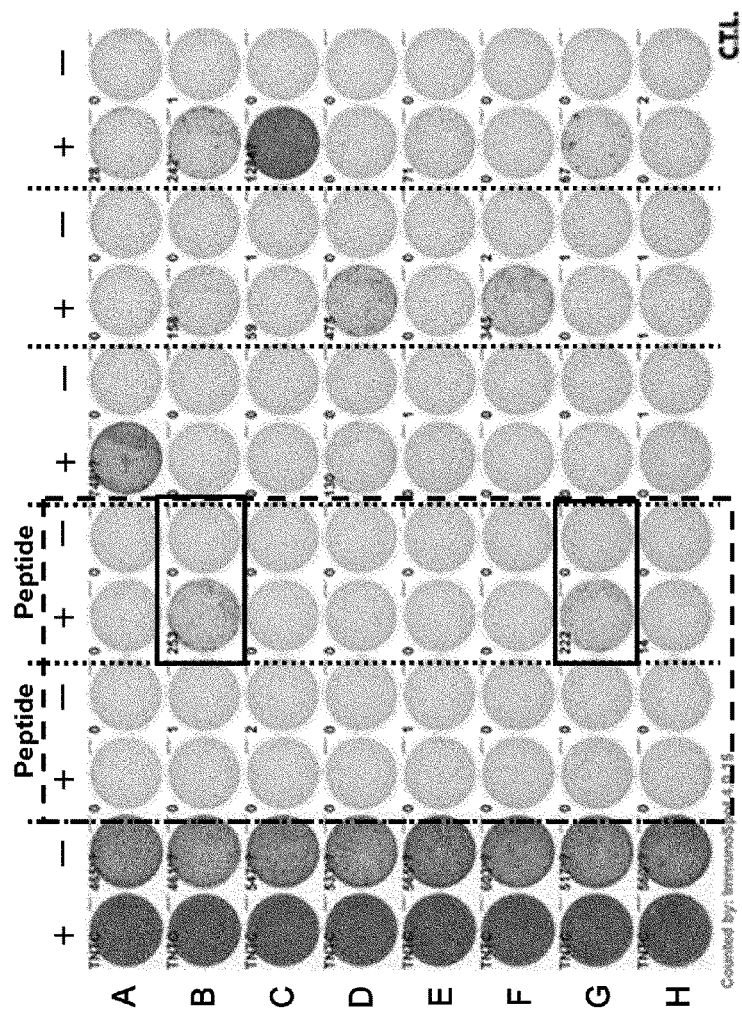
FIG. 2A
FIG. 2B

MPH-A02-9-282

MPH-A02-9-638

MPH-A02-10-1714

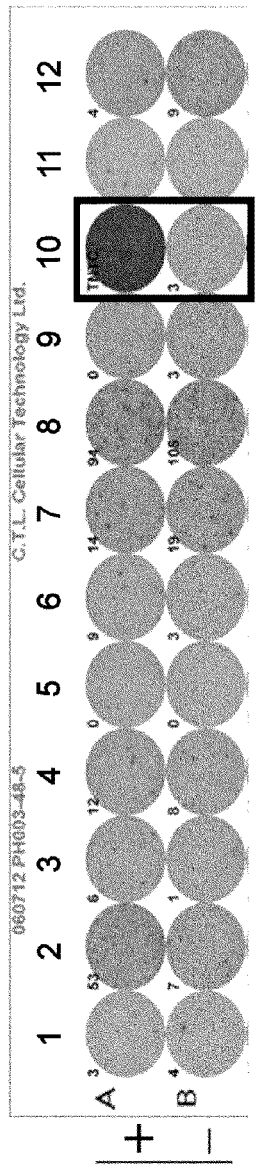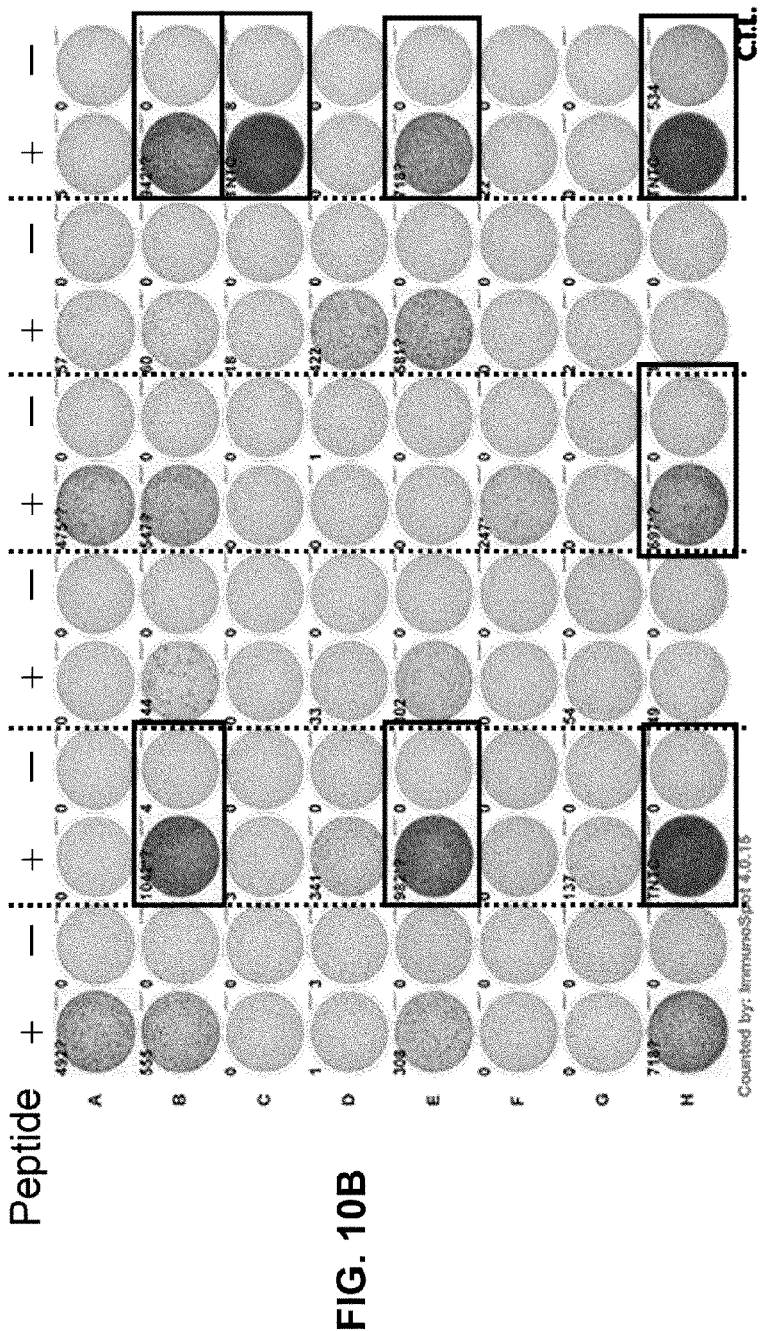
FIG. 10A
FIG. 10B

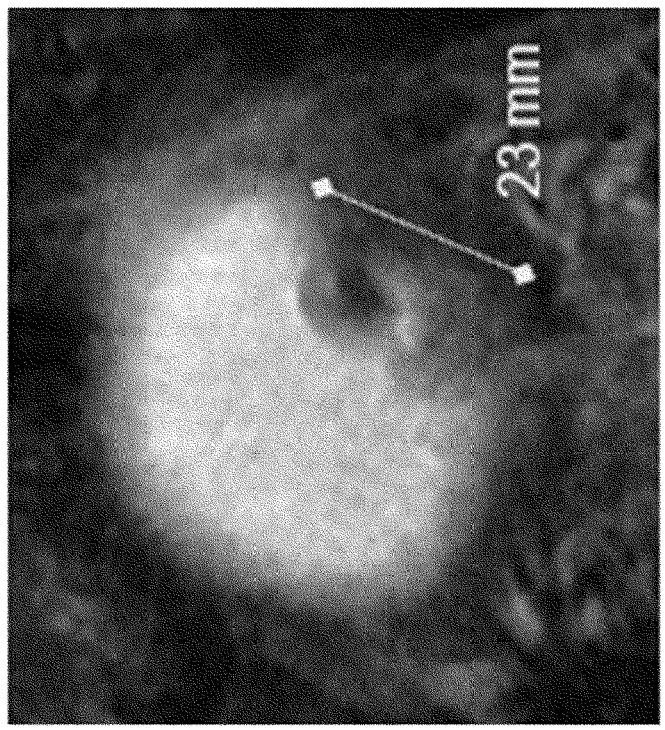
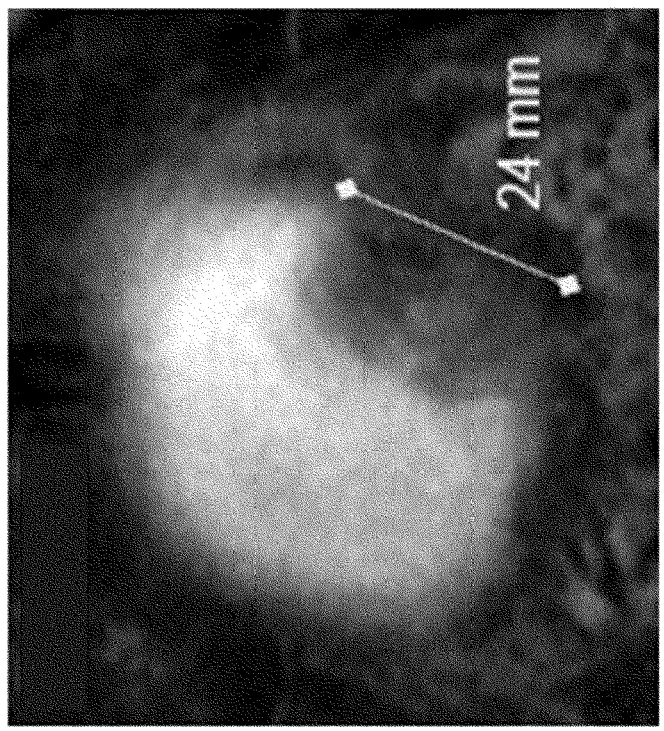
FIG. 19

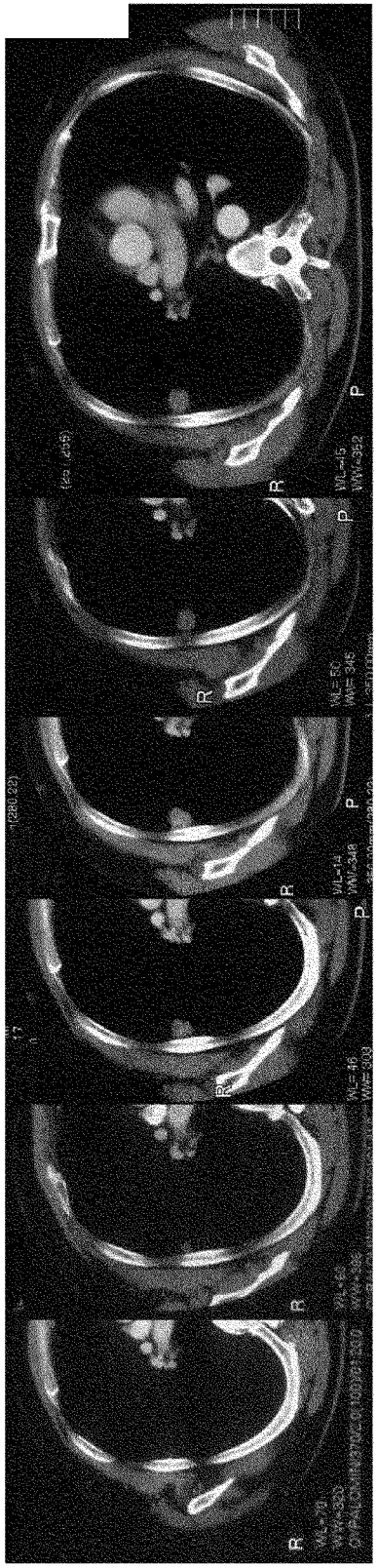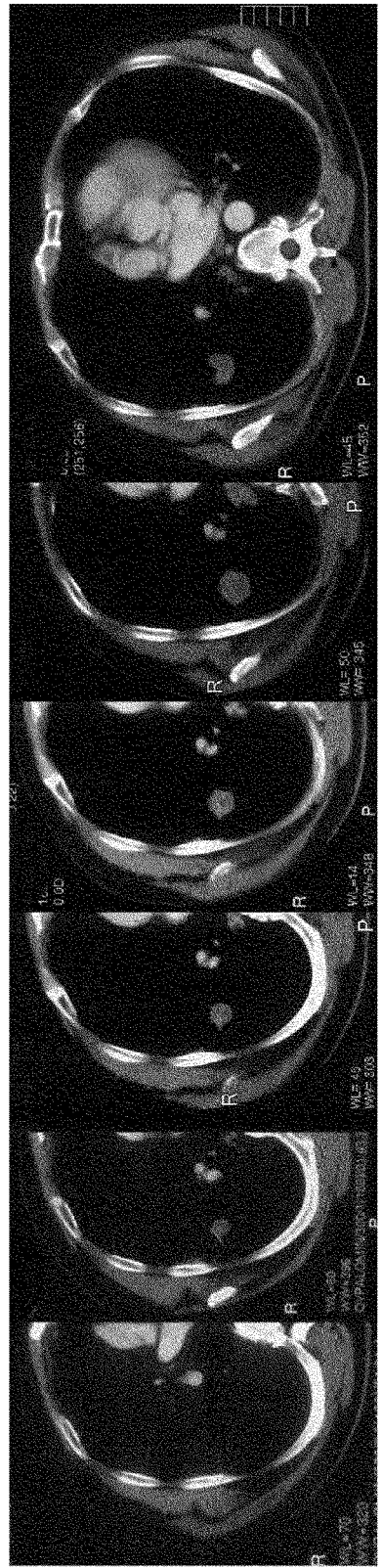
FIG. 21

```
                        SEQUENCE LISTING

<160> NUMBER OF SEQ ID NOS: 255

<210> SEQ ID NO 1
<211> LENGTH: 6319
<212> TYPE: DNA
<213> ORGANISM: Homo sapiens
<220> FEATURE:
<221> NAME/KEY: CDS
<222> LOCATION: (73)..(5415)

<400> SEQUENCE: 1
attgtttgaa tttgaaaacg gtaacatcgc agtgctgctc gcgggtctgg ctagtcaggc        60
gaagtttgca ga atg gaa tct aat ttt aat caa gag gga gta cct cga cca       111
              Met Glu Ser Asn Phe Asn Gln Glu Gly Val Pro Arg Pro
                1               5                  10 tct tat gtt ttt agt gct gac cca att gca agg cct tca gaa ata aat       159
Ser Tyr Val Phe Ser Ala Asp Pro Ile Ala Arg Pro Ser Glu Ile Asn
     15                  20                  25 ttc gat ggc att aag ctt gat ctg tct cat gaa ttt tcc tta gtt gct       207
Phe Asp Gly Ile Lys Leu Asp Leu Ser His Glu Phe Ser Leu Val Ala
 30                  35                  40                  45 cca aat act gag gca aac agt ttc gaa tct aaa gat tat ctc cag gtt       255
Pro Asn Thr Glu Ala Asn Ser Phe Glu Ser Lys Asp Tyr Leu Gln Val
                 50                  55                  60 tgt ctt cga ata aga cca ttt aca cag tca gaa aaa gaa ctt gag tct       303
Cys Leu Arg Ile Arg Pro Phe Thr Gln Ser Glu Lys Glu Leu Glu Ser
             65                  70                  75 gag ggc tgt gtg cat att ctg gat tca cag act gtt gtg ctg aaa gag       351
Glu Gly Cys Val His Ile Leu Asp Ser Gln Thr Val Val Leu Lys Glu
         80                  85                  90 cct caa tgc atc ctt ggt cgg tta agt gaa aaa agc tca ggg cag atg       399
Pro Gln Cys Ile Leu Gly Arg Leu Ser Glu Lys Ser Ser Gly Gln Met
     95                 100                 105 gca cag aaa ttc agt ttt tcc aag gtt ttt ggc cca gca act aca cag       447
Ala Gln Lys Phe Ser Phe Ser Lys Val Phe Gly Pro Ala Thr Thr Gln
110                 115                 120                 125 aag gaa ttc ttt cag ggt tgc att atg caa cca gta aaa gac ctc ttg       495
Lys Glu Phe Phe Gln Gly Cys Ile Met Gln Pro Val Lys Asp Leu Leu
                 130                 135                 140
```

| | | |
|---|---|---|
| aaa gga cag agt cgt ctg att ttt act tac ggg cta acc aat tca gga<br>Lys Gly Gln Ser Arg Leu Ile Phe Thr Tyr Gly Leu Thr Asn Ser Gly<br>              145                        150                      155 | 543 |
| aaa aca tat aca ttt caa ggg aca gaa gaa aat att ggc att ctg cct<br>Lys Thr Tyr Thr Phe Gln Gly Thr Glu Glu Asn Ile Gly Ile Leu Pro<br>160                        165                        170 | 591 |
| cga act ttg aat gta tta ttt gat agt ctt caa gaa aga ctg tat aca<br>Arg Thr Leu Asn Val Leu Phe Asp Ser Leu Gln Glu Arg Leu Tyr Thr<br>              175                        180                      185 | 639 |
| aag atg aac ctt aaa cca cat aga tcc aga gaa tac tta agg tta tca<br>Lys Met Asn Leu Lys Pro His Arg Ser Arg Glu Tyr Leu Arg Leu Ser<br>190                        195                        200                      205 | 687 |
| tca gaa caa gag aaa gaa gaa att gct agc aaa agt gca ttg ctt cgg<br>Ser Glu Gln Glu Lys Glu Glu Ile Ala Ser Lys Ser Ala Leu Leu Arg<br>                    210                        215                      220 | 735 |
| caa att aaa gag gtt act gtg cat aat gat agt gat gat act ctt tat<br>Gln Ile Lys Glu Val Thr Val His Asn Asp Ser Asp Asp Thr Leu Tyr<br>        225                        230                      235 | 783 |
| gga agt tta act aac tct ttg aat atc tca gag ttt gaa gaa tcc ata<br>Gly Ser Leu Thr Asn Ser Leu Asn Ile Ser Glu Phe Glu Glu Ser Ile<br>              240                        245                      250 | 831 |
| aaa gat tat gaa caa gcc aac ttg aat atg gct aat agt ata aaa ttt<br>Lys Asp Tyr Glu Gln Ala Asn Leu Asn Met Ala Asn Ser Ile Lys Phe<br>255                        260                        265 | 879 |
| tct gtg tgg gtt tct ttc ttt gaa att tac aat gaa tat att tat gac<br>Ser Val Trp Val Ser Phe Phe Glu Ile Tyr Asn Glu Tyr Ile Tyr Asp<br>270                        275                        280                      285 | 927 |
| tta ttt gtt cct gta tca tct aaa ttc caa aag aga aag atg ctg cgc<br>Leu Phe Val Pro Val Ser Ser Lys Phe Gln Lys Arg Lys Met Leu Arg<br>                    290                        295                      300 | 975 |
| ctt tcc caa gac gta aag ggc tat tct ttt ata aaa gat cta caa tgg<br>Leu Ser Gln Asp Val Lys Gly Tyr Ser Phe Ile Lys Asp Leu Gln Trp<br>        305                        310                      315 | 1023 |
| att caa gta tct gat tcc aaa gaa gcc tat aga ctt tta aaa cta gga<br>Ile Gln Val Ser Asp Ser Lys Glu Ala Tyr Arg Leu Leu Lys Leu Gly<br>              320                        325                      330 | 1071 |
| ata aag cac cag agt gtt gcc ttc aca aaa ttg aat aat gct tcc agt<br>Ile Lys His Gln Ser Val Ala Phe Thr Lys Leu Asn Asn Ala Ser Ser<br>335                        340                        345 | 1119 |
| aga agt cac agc ata ttc act gtt aaa ata tta cag att gaa gat tct<br>Arg Ser His Ser Ile Phe Thr Val Lys Ile Leu Gln Ile Glu Asp Ser<br>350                        355                        360                      365 | 1167 |
| gaa atg tct cgt gta att cga gtc agt gaa tta tct tta tgt gat ctt<br>Glu Met Ser Arg Val Ile Arg Val Ser Glu Leu Ser Leu Cys Asp Leu<br>                    370                        375                      380 | 1215 |
| gct ggt tca gaa cga act atg aag aca cag aat gaa ggt gaa agg tta<br>Ala Gly Ser Glu Arg Thr Met Lys Thr Gln Asn Glu Gly Glu Arg Leu<br>        385                        390                      395 | 1263 |
| aga gag act ggg aat atc aac act tct tta ttg act ctg gga aag tgt<br>Arg Glu Thr Gly Asn Ile Asn Thr Ser Leu Leu Thr Leu Gly Lys Cys<br>400                        405                        410 | 1311 |
| att aac gtc ttg aag aat agt gaa aag tca aag ttt caa cag cat gtg<br>Ile Asn Val Leu Lys Asn Ser Glu Lys Ser Lys Phe Gln Gln His Val<br>              415                        420                      425 | 1359 |
| cct ttc cgg gaa agt aaa ctg act cac tat ttt caa agt ttt ttt aat<br>Pro Phe Arg Glu Ser Lys Leu Thr His Tyr Phe Gln Ser Phe Phe Asn<br>430                        435                        440                      445 | 1407 |
| ggt aaa ggg aaa att tgt atg att gtc aat atc agc caa tgt tat tta<br>Gly Lys Gly Lys Ile Cys Met Ile Val Asn Ile Ser Gln Cys Tyr Leu<br>                    450                        455                      460 | 1455 |

```
gcc tat gat gaa aca ctc aat gta ttg aag ttc tcc gcc att gca caa    1503
Ala Tyr Asp Glu Thr Leu Asn Val Leu Lys Phe Ser Ala Ile Ala Gln
            465                 470                 475 aaa gtt tgt gtc cca gac act tta aat tcc tct caa gag aaa tta ttt    1551
Lys Val Cys Val Pro Asp Thr Leu Asn Ser Ser Gln Glu Lys Leu Phe
        480                 485                 490 gga cct gtc aaa tct tct caa gat gta tca cta gac agt aat tca aac    1599
Gly Pro Val Lys Ser Ser Gln Asp Val Ser Leu Asp Ser Asn Ser Asn
495                 500                 505 agt aaa ata tta aat gta aaa aga gcc acc att tca tgg gaa aat agt    1647
Ser Lys Ile Leu Asn Val Lys Arg Ala Thr Ile Ser Trp Glu Asn Ser
510                 515                 520                 525 cta gaa gat ttg atg gaa gac gag gat ttg gtt gag gag cta gaa aac    1695
Leu Glu Asp Leu Met Glu Asp Glu Asp Leu Val Glu Glu Leu Glu Asn
                530                 535                 540 gct gaa gaa act caa aat gtg gaa act aaa ctt ctt gat gaa gat cta    1743
Ala Glu Glu Thr Gln Asn Val Glu Thr Lys Leu Leu Asp Glu Asp Leu
            545                 550                 555 gat aaa aca tta gag gaa aat aag gct ttc att agc cac gag gag aaa    1791
Asp Lys Thr Leu Glu Glu Asn Lys Ala Phe Ile Ser His Glu Glu Lys
        560                 565                 570 aga aaa ctg ttg gac tta ata gaa gac ttg aaa aaa aaa ctg ata aat    1839
Arg Lys Leu Leu Asp Leu Ile Glu Asp Leu Lys Lys Lys Leu Ile Asn
    575                 580                 585 gaa aaa aag gaa aaa tta acc ttg gaa ttt aaa att cga gaa gaa gtt    1887
Glu Lys Lys Glu Lys Leu Thr Leu Glu Phe Lys Ile Arg Glu Glu Val
590                 595                 600                 605 aca cag gag ttt act cag tat tgg gct caa cgg gaa gct gac ttt aag    1935
Thr Gln Glu Phe Thr Gln Tyr Trp Ala Gln Arg Glu Ala Asp Phe Lys
                610                 615                 620 gag act ctg ctt caa gaa cga gag ata tta gaa gaa aat gct gaa cgt    1983
Glu Thr Leu Leu Gln Glu Arg Glu Ile Leu Glu Glu Asn Ala Glu Arg
            625                 630                 635 cgt ttg gct atc ttc aag gat ttg gtt ggt aaa tgt gac act cga gaa    2031
Arg Leu Ala Ile Phe Lys Asp Leu Val Gly Lys Cys Asp Thr Arg Glu
        640                 645                 650 gaa gca gcg aaa gac att tgt gcc aca aaa gtt gaa act gaa gaa gct    2079
Glu Ala Ala Lys Asp Ile Cys Ala Thr Lys Val Glu Thr Glu Glu Ala
    655                 660                 665 act gct tgt tta gaa cta aag ttt aat caa att aaa gct gaa tta gct    2127
Thr Ala Cys Leu Glu Leu Lys Phe Asn Gln Ile Lys Ala Glu Leu Ala
670                 675                 680                 685 aaa acc aaa gga gaa tta atc aaa acc aaa gaa gag tta aaa aag aga    2175
Lys Thr Lys Gly Glu Leu Ile Lys Thr Lys Glu Glu Leu Lys Lys Arg
                690                 695                 700 gaa aat gaa tca gat tca ttg att caa gag ctt gag aca tct aat aag    2223
Glu Asn Glu Ser Asp Ser Leu Ile Gln Glu Leu Glu Thr Ser Asn Lys
            705                 710                 715 aaa ata att aca cag aat caa aga att aaa gaa ttg ata aat ata att    2271
Lys Ile Ile Thr Gln Asn Gln Arg Ile Lys Glu Leu Ile Asn Ile Ile
        720                 725                 730 gat caa aaa gaa gat act atc aac gaa ttt cag aac cta aag tct cat    2319
Asp Gln Lys Glu Asp Thr Ile Asn Glu Phe Gln Asn Leu Lys Ser His
    735                 740                 745 atg gaa aac aca ttt aaa tgc aat gac aag gct gat aca tct tct tta    2367
Met Glu Asn Thr Phe Lys Cys Asn Asp Lys Ala Asp Thr Ser Ser Leu
750                 755                 760                 765 ata ata aac aat aaa ttg att tgt aat gaa aca gtt gaa gta cct aag    2415
Ile Ile Asn Asn Lys Leu Ile Cys Asn Glu Thr Val Glu Val Pro Lys
                770                 775                 780
```

-continued

```
gac agc aaa tct aaa atc tgt tca gaa aga aaa aga gta aat gaa aat    2463
Asp Ser Lys Ser Lys Ile Cys Ser Glu Arg Lys Arg Val Asn Glu Asn
        785                 790                 795 gaa ctt cag caa gat gaa cca cca gca aag aaa ggg tct atc cat gtt    2511
Glu Leu Gln Gln Asp Glu Pro Pro Ala Lys Lys Gly Ser Ile His Val
            800                 805                 810 agt tca gct atc act gaa gac caa aag aaa agt gaa gaa gtg cga ccg    2559
Ser Ser Ala Ile Thr Glu Asp Gln Lys Lys Ser Glu Glu Val Arg Pro
                815                 820                 825 aac att gca gaa att gaa gac atc aga gtt tta caa gaa aat aat gaa    2607
Asn Ile Ala Glu Ile Glu Asp Ile Arg Val Leu Gln Glu Asn Asn Glu
830                 835                 840                 845 gga ctg aga gca ttt tta ctc act att gag aat gaa ctt aaa aat gaa    2655
Gly Leu Arg Ala Phe Leu Leu Thr Ile Glu Asn Glu Leu Lys Asn Glu
                    850                 855                 860 aag gaa gaa aaa gca gaa tta aat aaa cag att gtt cat ttt cag cag    2703
Lys Glu Glu Lys Ala Glu Leu Asn Lys Gln Ile Val His Phe Gln Gln
                865                 870                 875 gaa ctt tct ctt tct gaa aaa aag aat tta act tta agt aaa gag gtc    2751
Glu Leu Ser Leu Ser Glu Lys Lys Asn Leu Thr Leu Ser Lys Glu Val
            880                 885                 890 caa caa att cag tca aat tat gat att gca att gct gaa tta cat gtg    2799
Gln Gln Ile Gln Ser Asn Tyr Asp Ile Ala Ile Ala Glu Leu His Val
        895                 900                 905 cag aaa agt aaa aat caa gaa cag gag gaa aag atc atg aaa ttg tca    2847
Gln Lys Ser Lys Asn Gln Glu Gln Glu Glu Lys Ile Met Lys Leu Ser
910                 915                 920                 925 aat gag ata gaa act gct aca aga agc att aca aat gtt tca caa       2895
Asn Glu Ile Glu Thr Ala Thr Arg Ser Ile Thr Asn Asn Val Ser Gln
                    930                 935                 940 ata aaa tta atg cac acg aaa ata gac gaa cta cgt act ctt gat tca   2943
Ile Lys Leu Met His Thr Lys Ile Asp Glu Leu Arg Thr Leu Asp Ser
                945                 950                 955 gtt tct cag att tca aac ata gat ttg ctc aat ctc agg gat ctg tca   2991
Val Ser Gln Ile Ser Asn Ile Asp Leu Leu Asn Leu Arg Asp Leu Ser
            960                 965                 970 aat ggt tct gag gag gat aat ttg cca aat aca cag tta gac ctt tta   3039
Asn Gly Ser Glu Glu Asp Asn Leu Pro Asn Thr Gln Leu Asp Leu Leu
        975                 980                 985 ggt aat gat tat ttg gta agt aag caa gtt aaa gaa tat cga att caa   3087
Gly Asn Asp Tyr Leu Val Ser Lys Gln Val Lys Glu Tyr Arg Ile Gln
990                 995                 1000                1005 gaa ccc aat agg gaa aat tct ttc cac tct agt att gaa gct att       3132
Glu Pro Asn Arg Glu Asn Ser Phe His Ser Ser Ile Glu Ala Ile
                    1010                1015                1020 tgg gaa gaa tgt aaa gag att gtg aag gcc tct tcc aaa aaa agt       3177
Trp Glu Glu Cys Lys Glu Ile Val Lys Ala Ser Ser Lys Lys Ser
                1025                1030                1035 cat cag att gag gaa ctg gaa caa caa att gaa aaa ttg cag gca       3222
His Gln Ile Glu Glu Leu Glu Gln Gln Ile Glu Lys Leu Gln Ala
            1040                1045                1050 gaa gta aaa ggc tat aag gat gaa aac aat aga cta aag gag aag       3267
Glu Val Lys Gly Tyr Lys Asp Glu Asn Asn Arg Leu Lys Glu Lys
        1055                1060                1065 gag cat aaa aac caa gat gac cta cta aaa gaa aaa gaa act ctt       3312
Glu His Lys Asn Gln Asp Asp Leu Leu Lys Glu Lys Glu Thr Leu
    1070                1075                1080 ata cag cag ctg aaa gaa gaa ttg caa gaa aaa aat gtt act ctt       3357
Ile Gln Gln Leu Lys Glu Glu Leu Gln Glu Lys Asn Val Thr Leu
1085                1090                1095
```

```
gat gtt caa ata cag  cat gta gtt gaa gga  aag aga gcg ctt tca       3402
Asp Val Gln Ile Gln  His Val Val Glu Gly  Lys Arg Ala Leu Ser
            1100               1105               1110 gaa ctt aca caa ggt  gtt act tgc tat aag  gca aaa ata aag gaa       3447
Glu Leu Thr Gln Gly  Val Thr Cys Tyr Lys  Ala Lys Ile Lys Glu
            1115               1120               1125 ctt gaa aca att tta  gag act cag aaa gtt  gaa tgt agt cat tca       3492
Leu Glu Thr Ile Leu  Glu Thr Gln Lys Val  Glu Cys Ser His Ser
            1130               1135               1140 gcc aag tta gaa caa  gac att ttg gaa aag  gaa tct atc atc tta       3537
Ala Lys Leu Glu Gln  Asp Ile Leu Glu Lys  Glu Ser Ile Ile Leu
            1145               1150               1155 aag cta gaa aga aat  ttg aag gaa ttt caa  gaa cat ctt cag gat       3582
Lys Leu Glu Arg Asn  Leu Lys Glu Phe Gln  Glu His Leu Gln Asp
            1160               1165               1170 tct gtc aaa aac acc  aaa gat tta aat gta  aag gaa ctc aag ctg       3627
Ser Val Lys Asn Thr  Lys Asp Leu Asn Val  Lys Glu Leu Lys Leu
            1175               1180               1185 aaa gaa gaa atc aca  cag tta aca aat aat  ttg caa gat atg aaa       3672
Lys Glu Glu Ile Thr  Gln Leu Thr Asn Asn  Leu Gln Asp Met Lys
            1190               1195               1200 cat tta ctt caa tta  aaa gaa gaa gaa gaa  gaa acc aac agg caa       3717
His Leu Leu Gln Leu  Lys Glu Glu Glu Glu  Glu Thr Asn Arg Gln
            1205               1210               1215 gaa aca gaa aaa ttg  aaa gag gaa ctc tct  gca agc tct gct cgt       3762
Glu Thr Glu Lys Leu  Lys Glu Glu Leu Ser  Ala Ser Ser Ala Arg
            1220               1225               1230 acc cag aat ctg aaa  gca gat ctt cag agg  aag gaa gaa gat tat       3807
Thr Gln Asn Leu Lys  Ala Asp Leu Gln Arg  Lys Glu Glu Asp Tyr
            1235               1240               1245 gct gac ctg aaa gag  aaa ctg act gat gcc  aaa aag cag att aag       3852
Ala Asp Leu Lys Glu  Lys Leu Thr Asp Ala  Lys Lys Gln Ile Lys
            1250               1255               1260 caa gta cag aaa gag  gta tct gta atg cgt  gat gag gat aaa tta       3897
Gln Val Gln Lys Glu  Val Ser Val Met Arg  Asp Glu Asp Lys Leu
            1265               1270               1275 ctg agg att aaa att  aat gaa ctg gag aaa  aag aaa aac cag tgt       3942
Leu Arg Ile Lys Ile  Asn Glu Leu Glu Lys  Lys Lys Asn Gln Cys
            1280               1285               1290 tct cag gaa tta gat  atg aaa cag cga acc  att cag caa ctc aag       3987
Ser Gln Glu Leu Asp  Met Lys Gln Arg Thr  Ile Gln Gln Leu Lys
            1295               1300               1305 gag cag tta aat aat  cag aaa gtg gaa gaa  gct ata caa cag tat       4032
Glu Gln Leu Asn Asn  Gln Lys Val Glu Glu  Ala Ile Gln Gln Tyr
            1310               1315               1320 gag aga gca tgc aaa  gat cta aat gtt aaa  gag aaa ata att gaa       4077
Glu Arg Ala Cys Lys  Asp Leu Asn Val Lys  Glu Lys Ile Ile Glu
            1325               1330               1335 gac atg cga atg aca  cta gaa gaa cag gaa  caa act cag gta gaa       4122
Asp Met Arg Met Thr  Leu Glu Glu Gln Glu  Gln Thr Gln Val Glu
            1340               1345               1350 cag gat caa gtg ctt  gag gct aaa tta gag  gaa gtt gaa agg ctg       4167
Gln Asp Gln Val Leu  Glu Ala Lys Leu Glu  Glu Val Glu Arg Leu
            1355               1360               1365 gcc aca gaa ttg gaa  aaa tgg aag gaa aaa  tgc aat gat ttg gaa       4212
Ala Thr Glu Leu Glu  Lys Trp Lys Glu Lys  Cys Asn Asp Leu Glu
            1370               1375               1380 acc aaa aac aat caa  agg tca aat aaa gaa  cat gag aac aac aca       4257
Thr Lys Asn Asn Gln  Arg Ser Asn Lys Glu  His Glu Asn Asn Thr
            1385               1390               1395
```

```
                                    -continued
gat gtg ctt gga aag  ctc act aat ctt caa  gat gag tta cag gag      4302
Asp Val Leu Gly Lys  Leu Thr Asn Leu Gln  Asp Glu Leu Gln Glu
            1400                 1405                  1410 tct gaa cag aaa tat  aat gct gat aga aag  aaa tgg tta gaa gaa      4347
Ser Glu Gln Lys Tyr  Asn Ala Asp Arg Lys  Lys Trp Leu Glu Glu
            1415                 1420                  1425 aaa atg atg ctt atc  act caa gcg aaa gaa  gca gag aat ata cga      4392
Lys Met Met Leu Ile  Thr Gln Ala Lys Glu  Ala Glu Asn Ile Arg
            1430                 1435                  1440 aat aaa gag atg aaa  aaa tat gct gag gac  agg gag cgt ttt ttt      4437
Asn Lys Glu Met Lys  Lys Tyr Ala Glu Asp  Arg Glu Arg Phe Phe
            1445                 1450                  1455 aag caa cag aat gaa  atg gaa ata ctg aca  gcc cag ctg aca gag      4482
Lys Gln Gln Asn Glu  Met Glu Ile Leu Thr  Ala Gln Leu Thr Glu
            1460                 1465                  1470 aaa gat agt gac ctt  caa aag tgg cga gaa  gaa cga gat caa ctg      4527
Lys Asp Ser Asp Leu  Gln Lys Trp Arg Glu  Glu Arg Asp Gln Leu
            1475                 1480                  1485 gtt gca gct tta gaa  ata cag cta aaa gca  ctg ata tcc agt aat      4572
Val Ala Ala Leu Glu  Ile Gln Leu Lys Ala  Leu Ile Ser Ser Asn
            1490                 1495                  1500 gta cag aaa gat aat  gaa att gaa caa cta  aaa agg atc ata tca      4617
Val Gln Lys Asp Asn  Glu Ile Glu Gln Leu  Lys Arg Ile Ile Ser
            1505                 1510                  1515 gag act tct aaa ata  gaa aca caa atc atg  gat atc aag ccc aaa      4662
Glu Thr Ser Lys Ile  Glu Thr Gln Ile Met  Asp Ile Lys Pro Lys
            1520                 1525                  1530 cgt att agt tca gca  gat cct gac aaa ctt  caa act gaa cct cta      4707
Arg Ile Ser Ser Ala  Asp Pro Asp Lys Leu  Gln Thr Glu Pro Leu
            1535                 1540                  1545 tcg aca agt ttt gaa  att tcc aga aat aaa  ata gag gat gga tct      4752
Ser Thr Ser Phe Glu  Ile Ser Arg Asn Lys  Ile Glu Asp Gly Ser
            1550                 1555                  1560 gta gtc ctt gac tct  tgt gaa gtg tca aca  gaa aat gat caa agc      4797
Val Val Leu Asp Ser  Cys Glu Val Ser Thr  Glu Asn Asp Gln Ser
            1565                 1570                  1575 act cga ttt cca aaa  cct gag tta gag att  caa ttt aca cct tta      4842
Thr Arg Phe Pro Lys  Pro Glu Leu Glu Ile  Gln Phe Thr Pro Leu
            1580                 1585                  1590 cag cca aac aaa atg  gca gtg aaa cac cct  ggt tgt acc aca cca      4887
Gln Pro Asn Lys Met  Ala Val Lys His Pro  Gly Cys Thr Thr Pro
            1595                 1600                  1605 gtg aca gtt aag att  ccc aag gct cgg aag  agg aag agt aat gaa      4932
Val Thr Val Lys Ile  Pro Lys Ala Arg Lys  Arg Lys Ser Asn Glu
            1610                 1615                  1620 atg gag gag gac ttg  gtg aaa tgt gaa aat  aag aag aat gct aca      4977
Met Glu Glu Asp Leu  Val Lys Cys Glu Asn  Lys Lys Asn Ala Thr
            1625                 1630                  1635 ccc aga act aat ttg  aaa ttt cct att tca  gat gat aga aat tct      5022
Pro Arg Thr Asn Leu  Lys Phe Pro Ile Ser  Asp Asp Arg Asn Ser
            1640                 1645                  1650 tct gtc aaa aag gaa  caa aag gtt gcc ata  cgt cca tca tct aag      5067
Ser Val Lys Lys Glu  Gln Lys Val Ala Ile  Arg Pro Ser Ser Lys
            1655                 1660                  1665 aaa aca tat tct tta  cgg agt cag gca tcc  ata att ggt gta aac      5112
Lys Thr Tyr Ser Leu  Arg Ser Gln Ala Ser  Ile Ile Gly Val Asn
            1670                 1675                  1680 ctg gcc act aag aaa  aaa gaa gga aca cta  cag aaa ttt gga gac      5157
Leu Ala Thr Lys Lys  Lys Glu Gly Thr Leu  Gln Lys Phe Gly Asp
            1685                 1690                  1695
```

```
ttc tta caa cat tct ccc tca att ctt caa tca aaa gca aag aag    5202
Phe Leu Gln His Ser Pro Ser Ile Leu Gln Ser Lys Ala Lys Lys
            1700            1705            1710 ata att gaa aca atg agc tct tca aag ctc tca aat gta gaa gca    5247
Ile Ile Glu Thr Met Ser Ser Ser Lys Leu Ser Asn Val Glu Ala
        1715            1720            1725 agt aaa gaa aat gtg tct caa cca aaa cga gcc aaa cgg aaa tta    5292
Ser Lys Glu Asn Val Ser Gln Pro Lys Arg Ala Lys Arg Lys Leu
    1730            1735            1740 tac aca agt gaa att tca tct cct att gat ata tca ggc caa gtg    5337
Tyr Thr Ser Glu Ile Ser Ser Pro Ile Asp Ile Ser Gly Gln Val
1745            1750            1755 att tta atg gac cag aaa atg aag gag agt gat cac cag att atc    5382
Ile Leu Met Asp Gln Lys Met Lys Glu Ser Asp His Gln Ile Ile
        1760            1765            1770 aaa cga cga ctt cga aca aaa aca gcc aaa taa atcacttatg          5425
Lys Arg Arg Leu Arg Thr Lys Thr Ala Lys
    1775            1780 gaaatgttta atataaattt tatagtcata gtcattggaa cttgcatcct gtattgtaaa    5485
tataaatgta tatattatgc attaaatcac tctgcatata gattgctgtt ttatacatag    5545
tataatttta attcaataaa tgagtcaaaa tttgtatatt tttataaggc tttttttataa   5605 tagcttcttt caaactgtat ttccctatta tctcagacat tggatcagtg aagatcctag    5665
gaaagaggct gttattctca tttattttgc tatacaggat gtaataggtc aggtatttgg    5725
tttacttata tttaacaatg tcttatgaat tttttttact ttatctgtta tacaactgat    5785
tttacatatc tgtttggatt atagctagga tttggagaat aagtgtgtac agatcacaaa    5845
acatgtatat acattattta gaaaagatct caagtcttta attagaatgt ctcacttatt    5905
ttgtaaacat tttgtgggta catagtacat gtatatattt acggggtatg tgagatgttt    5965
tgacacaggc atgcaatgtg aaatacgtgt atcatggaga atgaggtatc catcccctca    6025
agcatttttc ctttgaatta cagataatcc aattacattc tttagatcat ttaaaaatat    6085
acaagtaagt tattattgat tatagtcact ctattgtgct atcagatagt agatcattct    6145
ttttatctta tttgtttttg tacccattaa ccatccccac ctcccctgc aaccgtcagt     6205 acccttacca gccactggta accattcttc tactctgtat gcccatgagg tcaattgatt    6265
ttatttttag atcccataaa taaatgagaa catgcagtct ttgtcaaaaa aaaa          6319

<210> SEQ ID NO 2
<211> LENGTH: 1780
<212> TYPE: PRT
<213> ORGANISM: Homo sapiens

<400> SEQUENCE: 2

Met Glu Ser Asn Phe Asn Gln Glu Gly Val Pro Arg Pro Ser Tyr Val
1               5                   10                  15

Phe Ser Ala Asp Pro Ile Ala Arg Pro Ser Glu Ile Asn Phe Asp Gly
            20                  25                  30

Ile Lys Leu Asp Leu Ser His Glu Phe Ser Leu Val Ala Pro Asn Thr
        35                  40                  45

Glu Ala Asn Ser Phe Glu Ser Lys Asp Tyr Leu Gln Val Cys Leu Arg
    50                  55                  60

Ile Arg Pro Phe Thr Gln Ser Glu Lys Glu Leu Glu Ser Glu Gly Cys
65                  70                  75                  80

Val His Ile Leu Asp Ser Gln Thr Val Val Leu Lys Glu Pro Gln Cys
                85                  90                  95
```

```
Ile Leu Gly Arg Leu Ser Glu Lys Ser Ser Gly Gln Met Ala Gln Lys
            100                 105                 110

Phe Ser Phe Ser Lys Val Phe Gly Pro Ala Thr Thr Gln Lys Glu Phe
        115                 120                 125

Phe Gln Gly Cys Ile Met Gln Pro Val Lys Asp Leu Leu Lys Gly Gln
    130                 135                 140

Ser Arg Leu Ile Phe Thr Tyr Gly Leu Thr Asn Ser Gly Lys Thr Tyr
145                 150                 155                 160

Thr Phe Gln Gly Thr Glu Asn Ile Gly Ile Leu Pro Arg Thr Leu
                165                 170                 175

Asn Val Leu Phe Asp Ser Leu Gln Glu Arg Leu Tyr Thr Lys Met Asn
                180                 185                 190

Leu Lys Pro His Arg Ser Arg Glu Tyr Leu Arg Leu Ser Ser Glu Gln
                195                 200                 205

Glu Lys Glu Glu Ile Ala Ser Lys Ser Ala Leu Leu Arg Gln Ile Lys
        210                 215                 220

Glu Val Thr Val His Asn Asp Ser Asp Asp Thr Leu Tyr Gly Ser Leu
225                 230                 235                 240

Thr Asn Ser Leu Asn Ile Ser Glu Phe Glu Glu Ser Ile Lys Asp Tyr
                245                 250                 255

Glu Gln Ala Asn Leu Asn Met Ala Asn Ser Ile Lys Phe Ser Val Trp
            260                 265                 270

Val Ser Phe Phe Glu Ile Tyr Asn Glu Tyr Ile Tyr Asp Leu Phe Val
        275                 280                 285

Pro Val Ser Ser Lys Phe Gln Lys Arg Lys Met Leu Arg Leu Ser Gln
    290                 295                 300

Asp Val Lys Gly Tyr Ser Phe Ile Lys Asp Leu Gln Trp Ile Gln Val
305                 310                 315                 320

Ser Asp Ser Lys Glu Ala Tyr Arg Leu Leu Lys Leu Gly Ile Lys His
                325                 330                 335

Gln Ser Val Ala Phe Thr Lys Leu Asn Asn Ala Ser Ser Arg Ser His
            340                 345                 350

Ser Ile Phe Thr Val Lys Ile Leu Gln Ile Glu Asp Ser Glu Met Ser
        355                 360                 365

Arg Val Ile Arg Val Ser Glu Leu Ser Leu Cys Asp Leu Ala Gly Ser
370                 375                 380

Glu Arg Thr Met Lys Thr Gln Asn Glu Gly Glu Arg Leu Arg Glu Thr
385                 390                 395                 400

Gly Asn Ile Asn Thr Ser Leu Leu Thr Leu Gly Lys Cys Ile Asn Val
                405                 410                 415

Leu Lys Asn Ser Glu Lys Ser Lys Phe Gln Gln His Val Pro Phe Arg
            420                 425                 430

Glu Ser Lys Leu Thr His Tyr Phe Gln Ser Phe Phe Asn Gly Lys Gly
        435                 440                 445

Lys Ile Cys Met Ile Val Asn Ile Ser Gln Cys Tyr Leu Ala Tyr Asp
    450                 455                 460

Glu Thr Leu Asn Val Leu Lys Phe Ser Ala Ile Ala Gln Lys Val Cys
465                 470                 475                 480

Val Pro Asp Thr Leu Asn Ser Ser Gln Glu Lys Leu Phe Gly Pro Val
                485                 490                 495

Lys Ser Ser Gln Asp Val Ser Leu Asp Ser Asn Ser Asn Ser Lys Ile
            500                 505                 510

Leu Asn Val Lys Arg Ala Thr Ile Ser Trp Glu Asn Ser Leu Glu Asp
        515                 520                 525
```

-continued

Leu Met Glu Asp Glu Asp Leu Val Glu Leu Glu Asn Ala Glu Glu
    530                 535                 540

Thr Gln Asn Val Glu Thr Lys Leu Leu Asp Glu Asp Leu Asp Lys Thr
545                 550                 555                 560

Leu Glu Glu Asn Lys Ala Phe Ile Ser His Glu Glu Lys Arg Lys Leu
                565                 570                 575

Leu Asp Leu Ile Glu Asp Leu Lys Lys Lys Leu Ile Asn Glu Lys Lys
                580                 585                 590

Glu Lys Leu Thr Leu Glu Phe Lys Ile Arg Glu Glu Val Thr Gln Glu
                595                 600                 605

Phe Thr Gln Tyr Trp Ala Gln Arg Glu Ala Asp Phe Lys Glu Thr Leu
    610                 615                 620

Leu Gln Glu Arg Glu Ile Leu Glu Glu Asn Ala Glu Arg Arg Leu Ala
625                 630                 635                 640

Ile Phe Lys Asp Leu Val Gly Lys Cys Asp Thr Arg Glu Glu Ala Ala
                645                 650                 655

Lys Asp Ile Cys Ala Thr Lys Val Glu Thr Glu Glu Ala Thr Ala Cys
                660                 665                 670

Leu Glu Leu Lys Phe Asn Gln Ile Lys Ala Glu Leu Ala Lys Thr Lys
                675                 680                 685

Gly Glu Leu Ile Lys Thr Lys Glu Glu Leu Lys Lys Arg Glu Asn Glu
690                 695                 700

Ser Asp Ser Leu Ile Gln Glu Leu Glu Thr Ser Asn Lys Lys Ile Ile
705                 710                 715                 720

Thr Gln Asn Gln Arg Ile Lys Glu Leu Ile Asn Ile Asp Gln Lys
                725                 730                 735

Glu Asp Thr Ile Asn Glu Phe Gln Asn Leu Lys Ser His Met Glu Asn
                740                 745                 750

Thr Phe Lys Cys Asn Asp Lys Ala Asp Thr Ser Ser Leu Ile Ile Asn
    755                 760                 765

Asn Lys Leu Ile Cys Asn Glu Thr Val Glu Val Pro Lys Asp Ser Lys
    770                 775                 780

Ser Lys Ile Cys Ser Glu Arg Lys Arg Val Asn Glu Asn Glu Leu Gln
785                 790                 795                 800

Gln Asp Glu Pro Pro Ala Lys Lys Gly Ser Ile His Val Ser Ser Ala
                805                 810                 815

Ile Thr Glu Asp Gln Lys Lys Ser Glu Glu Val Arg Pro Asn Ile Ala
                820                 825                 830

Glu Ile Glu Asp Ile Arg Val Leu Gln Glu Asn Asn Glu Gly Leu Arg
                835                 840                 845

Ala Phe Leu Leu Thr Ile Glu Asn Glu Leu Lys Asn Glu Lys Glu Glu
    850                 855                 860

Lys Ala Glu Leu Asn Lys Gln Ile Val His Phe Gln Gln Glu Leu Ser
865                 870                 875                 880

Leu Ser Glu Lys Lys Asn Leu Thr Leu Ser Lys Glu Val Gln Gln Ile
                885                 890                 895

Gln Ser Asn Tyr Asp Ile Ala Ile Ala Glu Leu His Val Gln Lys Ser
                900                 905                 910

Lys Asn Gln Glu Gln Glu Lys Ile Met Lys Leu Ser Asn Glu Ile
                915                 920                 925

Glu Thr Ala Thr Arg Ser Ile Thr Asn Asn Val Ser Gln Ile Lys Leu
    930                 935                 940

Met His Thr Lys Ile Asp Glu Leu Arg Thr Leu Asp Ser Val Ser Gln

-continued

```
         945                 950                 955                 960
Ile Ser Asn Ile Asp Leu Leu Asn Leu Arg Asp Leu Ser Asn Gly Ser
             965                 970                 975
Glu Glu Asp Asn Leu Pro Asn Thr Gln Leu Asp Leu Leu Gly Asn Asp
             980                 985                 990
Tyr Leu Val Ser Lys Gln Val Lys Glu Tyr Arg Ile Gln Glu Pro Asn
             995                1000                1005
Arg Glu Asn Ser Phe His Ser Ser Ile Glu Ala Ile Trp Glu Glu
            1010                1015                1020
Cys Lys Glu Ile Val Lys Ala Ser Ser Lys Lys Ser His Gln Ile
            1025                1030                1035
Glu Glu Leu Glu Gln Gln Ile Glu Lys Leu Gln Ala Glu Val Lys
            1040                1045                1050
Gly Tyr Lys Asp Glu Asn Asn Arg Leu Lys Glu Lys Glu His Lys
            1055                1060                1065
Asn Gln Asp Asp Leu Leu Lys Glu Lys Glu Thr Leu Ile Gln Gln
            1070                1075                1080
Leu Lys Glu Glu Leu Gln Glu Lys Asn Val Thr Leu Asp Val Gln
            1085                1090                1095
Ile Gln His Val Val Glu Gly Lys Arg Ala Leu Ser Glu Leu Thr
            1100                1105                1110
Gln Gly Val Thr Cys Tyr Lys Ala Lys Ile Lys Glu Leu Glu Thr
            1115                1120                1125
Ile Leu Glu Thr Gln Lys Val Glu Cys Ser His Ser Ala Lys Leu
            1130                1135                1140
Glu Gln Asp Ile Leu Glu Lys Glu Ser Ile Ile Leu Lys Leu Glu
            1145                1150                1155
Arg Asn Leu Lys Glu Phe Gln Glu His Leu Gln Asp Ser Val Lys
            1160                1165                1170
Asn Thr Lys Asp Leu Asn Val Lys Glu Leu Lys Leu Lys Glu Glu
            1175                1180                1185
Ile Thr Gln Leu Thr Asn Asn Leu Gln Asp Met Lys His Leu Leu
            1190                1195                1200
Gln Leu Lys Glu Glu Glu Glu Thr Asn Arg Gln Glu Thr Glu
            1205                1210                1215
Lys Leu Lys Glu Glu Leu Ser Ala Ser Ala Arg Thr Gln Asn
            1220                1225                1230
Leu Lys Ala Asp Leu Gln Arg Lys Glu Glu Asp Tyr Ala Asp Leu
            1235                1240                1245
Lys Glu Lys Leu Thr Asp Ala Lys Lys Gln Ile Lys Gln Val Gln
            1250                1255                1260
Lys Glu Val Ser Val Met Arg Asp Glu Asp Lys Leu Leu Arg Ile
            1265                1270                1275
Lys Ile Asn Glu Leu Glu Lys Lys Lys Asn Gln Cys Ser Gln Glu
            1280                1285                1290
Leu Asp Met Lys Gln Arg Thr Ile Gln Gln Leu Lys Glu Gln Leu
            1295                1300                1305
Asn Asn Gln Lys Val Glu Glu Ala Ile Gln Gln Tyr Glu Arg Ala
            1310                1315                1320
Cys Lys Asp Leu Asn Val Lys Glu Lys Ile Ile Glu Asp Met Arg
            1325                1330                1335
Met Thr Leu Glu Glu Gln Glu Gln Thr Gln Val Glu Gln Asp Gln
            1340                1345                1350
```

-continued

| | | | | | | | | | | | |
|---|---|---|---|---|---|---|---|---|---|---|---|
|Val|Leu|Glu|Ala|Lys|Leu|Glu|Glu|Val|Glu|Arg|Leu|Ala|Thr|Glu|
| |1355| | | |1360| | | |1365| | | | | |

Val Leu Glu Ala Lys Leu Glu Glu Val Glu Arg Leu Ala Thr Glu
    1355                1360                1365

Leu Glu Lys Trp Lys Glu Lys Cys Asn Asp Leu Glu Thr Lys Asn
    1370                1375                1380

Asn Gln Arg Ser Asn Lys Glu His Glu Asn Asn Thr Asp Val Leu
    1385                1390                1395

Gly Lys Leu Thr Asn Leu Gln Asp Glu Leu Gln Glu Ser Glu Gln
    1400                1405                1410

Lys Tyr Asn Ala Asp Arg Lys Lys Trp Leu Glu Glu Lys Met Met
    1415                1420                1425

Leu Ile Thr Gln Ala Lys Glu Ala Glu Asn Ile Arg Asn Lys Glu
    1430                1435                1440

Met Lys Lys Tyr Ala Glu Asp Arg Glu Arg Phe Phe Lys Gln Gln
    1445                1450                1455

Asn Glu Met Glu Ile Leu Thr Ala Gln Leu Thr Glu Lys Asp Ser
    1460                1465                1470

Asp Leu Gln Lys Trp Arg Glu Glu Arg Asp Gln Leu Val Ala Ala
    1475                1480                1485

Leu Glu Ile Gln Leu Lys Ala Leu Ile Ser Ser Asn Val Gln Lys
    1490                1495                1500

Asp Asn Glu Ile Glu Gln Leu Lys Arg Ile Ile Ser Glu Thr Ser
    1505                1510                1515

Lys Ile Glu Thr Gln Ile Met Asp Ile Lys Pro Lys Arg Ile Ser
    1520                1525                1530

Ser Ala Asp Pro Asp Lys Leu Gln Thr Glu Pro Leu Ser Thr Ser
    1535                1540                1545

Phe Glu Ile Ser Arg Asn Lys Ile Glu Asp Gly Ser Val Val Leu
    1550                1555                1560

Asp Ser Cys Glu Val Ser Thr Glu Asn Asp Gln Ser Thr Arg Phe
    1565                1570                1575

Pro Lys Pro Glu Leu Glu Ile Gln Phe Thr Pro Leu Gln Pro Asn
    1580                1585                1590

Lys Met Ala Val Lys His Pro Gly Cys Thr Thr Pro Val Thr Val
    1595                1600                1605

Lys Ile Pro Lys Ala Arg Lys Arg Lys Ser Asn Glu Met Glu Glu
    1610                1615                1620

Asp Leu Val Lys Cys Glu Asn Lys Lys Asn Ala Thr Pro Arg Thr
    1625                1630                1635

Asn Leu Lys Phe Pro Ile Ser Asp Asp Arg Asn Ser Ser Val Lys
    1640                1645                1650

Lys Glu Gln Lys Val Ala Ile Arg Pro Ser Ser Lys Lys Thr Tyr
    1655                1660                1665

Ser Leu Arg Ser Gln Ala Ser Ile Ile Gly Val Asn Leu Ala Thr
    1670                1675                1680

Lys Lys Lys Glu Gly Thr Leu Gln Lys Phe Gly Asp Phe Leu Gln
    1685                1690                1695

His Ser Pro Ser Ile Leu Gln Ser Lys Ala Lys Lys Ile Ile Glu
    1700                1705                1710

Thr Met Ser Ser Ser Lys Leu Ser Asn Val Glu Ala Ser Lys Glu
    1715                1720                1725

Asn Val Ser Gln Pro Lys Arg Ala Lys Arg Lys Leu Tyr Thr Ser
    1730                1735                1740

Glu Ile Ser Ser Pro Ile Asp Ile Ser Gly Gln Val Ile Leu Met
    1745                1750                1755

```
Asp Gln  Lys Met Lys Glu  Ser  Asp His Gln Ile Ile  Lys Arg Arg
    1760         1765              1770

Leu Arg  Thr Lys Thr Ala Lys
    1775         1780

<210> SEQ ID NO 3
<211> LENGTH: 5318
<212> TYPE: DNA
<213> ORGANISM: Homo sapiens
<220> FEATURE:
<221> NAME/KEY: CDS
<222> LOCATION: (79)..(2511)

<400> SEQUENCE: 3
gagactcgcc actgccgcgg ccgctgggcc tgagtgtcgc cttcgccgcc atggacgcca         60
ccgggcgctg acagacct atg gag agt cag ggt gtg cct ccc ggg cct tat        111
                    Met Glu Ser Gln Gly Val Pro Pro Gly Pro Tyr
                      1               5                  10 cgg gcc acc aag ctg tgg aat gaa gtt acc aca tct ttt cga gca gga        159
Arg Ala Thr Lys Leu Trp Asn Glu Val Thr Thr Ser Phe Arg Ala Gly
             15                  20                  25 atg cct cta aga aaa cac aga caa cac ttt aaa aaa tat ggc aat tgt        207
Met Pro Leu Arg Lys His Arg Gln His Phe Lys Lys Tyr Gly Asn Cys
         30                  35                  40 ttc aca gca gga gaa gca gtg gat tgg ctt tat gac cta tta aga aat        255
Phe Thr Ala Gly Glu Ala Val Asp Trp Leu Tyr Asp Leu Leu Arg Asn
     45                  50                  55 aat agc aat ttt ggt cct gaa gtt aca agg caa cag act atc caa ctg        303
Asn Ser Asn Phe Gly Pro Glu Val Thr Arg Gln Gln Thr Ile Gln Leu
 60                  65                  70                  75 ttg agg aaa ttt ctt aag aat cat gta att gaa gat atc aaa ggg agg        351
Leu Arg Lys Phe Leu Lys Asn His Val Ile Glu Asp Ile Lys Gly Arg
                 80                  85                  90 tgg gga tca gaa aat gtt gat gat aac aac cag ctc ttc aga ttt cct        399
Trp Gly Ser Glu Asn Val Asp Asp Asn Asn Gln Leu Phe Arg Phe Pro
             95                 100                 105 gca act tcg cca ctt aaa act cta cca cga agg tat cca gaa ttg aga        447
Ala Thr Ser Pro Leu Lys Thr Leu Pro Arg Arg Tyr Pro Glu Leu Arg
         110                 115                 120 aaa aac aac ata gag aac ttt tcc aaa gat aaa gat agc att ttt aaa        495
Lys Asn Asn Ile Glu Asn Phe Ser Lys Asp Lys Asp Ser Ile Phe Lys
     125                 130                 135 tta cga aac tta tct cgt aga act cct aaa agg cat gga tta cat tta        543
Leu Arg Asn Leu Ser Arg Arg Thr Pro Lys Arg His Gly Leu His Leu
 140                 145                 150                 155 tct cag gaa aat ggc gag aaa ata aag cat gaa ata atc aat gaa gat        591
Ser Gln Glu Asn Gly Glu Lys Ile Lys His Glu Ile Ile Asn Glu Asp
                 160                 165                 170 caa gaa aat gca att gat aat aga gaa cta agc cag gaa gat gtt gaa        639
Gln Glu Asn Ala Ile Asp Asn Arg Glu Leu Ser Gln Glu Asp Val Glu
             175                 180                 185 gaa gtt tgg aga tat gtt att ctg atc tac ctg caa acc att tta ggt        687
Glu Val Trp Arg Tyr Val Ile Leu Ile Tyr Leu Gln Thr Ile Leu Gly
         190                 195                 200 gtg cca tcc cta gaa gaa gtc ata aat cca aaa caa gta att ccc caa        735
Val Pro Ser Leu Glu Glu Val Ile Asn Pro Lys Gln Val Ile Pro Gln
     205                 210                 215 tat ata atg tac aac atg gcc aat aca agt aaa cgt gga gta gtt ata        783
Tyr Ile Met Tyr Asn Met Ala Asn Thr Ser Lys Arg Gly Val Val Ile
220                 225                 230                 235
```

```
cta caa aac aaa tca gat gac ctc cct cac tgg gta tta tct gcc atg      831
Leu Gln Asn Lys Ser Asp Asp Leu Pro His Trp Val Leu Ser Ala Met
            240             245             250 aag tgc cta gca aat tgg cca aga agc aat gat atg aat aat cca act      879
Lys Cys Leu Ala Asn Trp Pro Arg Ser Asn Asp Met Asn Asn Pro Thr
        255             260             265 tat gtt gga ttt gaa cga gat gta ttc aga aca atc gca gat tat ttt      927
Tyr Val Gly Phe Glu Arg Asp Val Phe Arg Thr Ile Ala Asp Tyr Phe
        270             275             280 cta gat ctc cct gaa cct cta ctt act ttt gaa tat tac gaa tta ttt      975
Leu Asp Leu Pro Glu Pro Leu Leu Thr Phe Glu Tyr Tyr Glu Leu Phe
        285             290             295 gta aac att ttg gtt gtt tgt ggc tac atc aca gtt tca gat aga tcc     1023
Val Asn Ile Leu Val Val Cys Gly Tyr Ile Thr Val Ser Asp Arg Ser
300             305             310             315 agt ggg ata cat aaa att caa gat gat cca cag tct tca aaa ttc ctt     1071
Ser Gly Ile His Lys Ile Gln Asp Asp Pro Gln Ser Ser Lys Phe Leu
            320             325             330 cac tta aac aat ttg aat tcc ttc aaa tca act gag tgc ctt ctt ctc     1119
His Leu Asn Asn Leu Asn Ser Phe Lys Ser Thr Glu Cys Leu Leu Leu
            335             340             345 agt ctg ctt cat aga gaa aaa aac aaa gaa gaa tca gat tct act gag     1167
Ser Leu Leu His Arg Glu Lys Asn Lys Glu Glu Ser Asp Ser Thr Glu
        350             355             360 aga cta cag ata agc aat cca gga ttt caa gaa aga tgt gct aag aaa     1215
Arg Leu Gln Ile Ser Asn Pro Gly Phe Gln Glu Arg Cys Ala Lys Lys
        365             370             375 atg cag cta gtt aat tta aga aac aga aga gtg agt gct aat gac ata     1263
Met Gln Leu Val Asn Leu Arg Asn Arg Arg Val Ser Ala Asn Asp Ile
380             385             390             395 atg gga gga agt tgt cat aat tta ata ggg tta agt aat atg cat gat     1311
Met Gly Gly Ser Cys His Asn Leu Ile Gly Leu Ser Asn Met His Asp
            400             405             410 cta tcc tct aac agc aaa cca agg tgc tgt tct ttg gaa gga att gta     1359
Leu Ser Ser Asn Ser Lys Pro Arg Cys Cys Ser Leu Glu Gly Ile Val
            415             420             425 gat gtg cca ggg aat tca agt aaa gag gca tcc agt gtc ttt cat caa     1407
Asp Val Pro Gly Asn Ser Ser Lys Glu Ala Ser Ser Val Phe His Gln
        430             435             440 tct ttt ccg aac ata gaa gga caa aat aat aaa ctg ttt tta gag tct     1455
Ser Phe Pro Asn Ile Glu Gly Gln Asn Asn Lys Leu Phe Leu Glu Ser
        445             450             455 aag ccc aaa cag gaa ttc ctg ttg aat ctt cat tca gag gaa aat att     1503
Lys Pro Lys Gln Glu Phe Leu Leu Asn Leu His Ser Glu Glu Asn Ile
460             465             470             475 caa aag cca ttc agt gct ggt ttt aag aga acc tct act ttg act gtt     1551
Gln Lys Pro Phe Ser Ala Gly Phe Lys Arg Thr Ser Thr Leu Thr Val
            480             485             490 caa gac caa gag gag ttg tgt aat ggg aaa tgc aag tca aaa cag ctt     1599
Gln Asp Gln Glu Glu Leu Cys Asn Gly Lys Cys Lys Ser Lys Gln Leu
        495             500             505 tgt agg tct cag agt ttg ctt tta aga agt agt aca aga agg aat agt     1647
Cys Arg Ser Gln Ser Leu Leu Leu Arg Ser Ser Thr Arg Arg Asn Ser
        510             515             520 tat atc aat aca cca gtg gct gaa att atc atg aaa cca aat gtt gga     1695
Tyr Ile Asn Thr Pro Val Ala Glu Ile Ile Met Lys Pro Asn Val Gly
525             530             535 caa ggc agc aca agt gtg caa aca gct atg gaa agt gaa ctc gga gag     1743
Gln Gly Ser Thr Ser Val Gln Thr Ala Met Glu Ser Glu Leu Gly Glu
540             545             550             555
```

```
tct agt gcc aca atc aat aaa aga ctc tgc aaa agt aca ata gaa ctt    1791
Ser Ser Ala Thr Ile Asn Lys Arg Leu Cys Lys Ser Thr Ile Glu Leu
            560                 565                 570 tca gaa aat tct tta ctt cca gct tct tct atg ttg act ggc aca caa    1839
Ser Glu Asn Ser Leu Leu Pro Ala Ser Ser Met Leu Thr Gly Thr Gln
        575                 580                 585 agc ttg ctg caa cct cat tta gag agg gtt gcc atc gat gct cta cag    1887
Ser Leu Leu Gln Pro His Leu Glu Arg Val Ala Ile Asp Ala Leu Gln
    590                 595                 600 tta tgt tgt ttg tta ctt ccc cca cca aat cgt aga aag ctt caa ctt    1935
Leu Cys Cys Leu Leu Leu Pro Pro Pro Asn Arg Arg Lys Leu Gln Leu
605                 610                 615 tta atg cgt atg att tcc cga atg agt caa aat gtt gat atg ccc aaa    1983
Leu Met Arg Met Ile Ser Arg Met Ser Gln Asn Val Asp Met Pro Lys
620                 625                 630                 635 ctt cat gat gca atg ggt acg agg tca ctg atg ata cat acc ttt tct    2031
Leu His Asp Ala Met Gly Thr Arg Ser Leu Met Ile His Thr Phe Ser
            640                 645                 650 cga tgt gtg tta tgc tgt gct gaa gaa gtg gat ctt gat gag ctt ctt    2079
Arg Cys Val Leu Cys Cys Ala Glu Glu Val Asp Leu Asp Glu Leu Leu
        655                 660                 665 gct gga aga tta gtt tct ttc tta atg gat cat cat cag gaa att ctt    2127
Ala Gly Arg Leu Val Ser Phe Leu Met Asp His His Gln Glu Ile Leu
    670                 675                 680 caa gta ccc tct tac tta cag act gca gtg gaa aaa cat ctt gac tac    2175
Gln Val Pro Ser Tyr Leu Gln Thr Ala Val Glu Lys His Leu Asp Tyr
685                 690                 695 tta aaa aag gga cat att gaa aat cct gga gat gga cta ttt gct cct    2223
Leu Lys Lys Gly His Ile Glu Asn Pro Gly Asp Gly Leu Phe Ala Pro
700                 705                 710                 715 ttg cca act tac tca tac tgt aag cag att agt gct cag gag ttt gat    2271
Leu Pro Thr Tyr Ser Tyr Cys Lys Gln Ile Ser Ala Gln Glu Phe Asp
            720                 725                 730 gag caa aaa gtt tct acc tct caa gct gca att gca gaa ctt tta gaa    2319
Glu Gln Lys Val Ser Thr Ser Gln Ala Ala Ile Ala Glu Leu Leu Glu
        735                 740                 745 aat att att aaa aac agg agt tta cct cta aag gag aaa aga aaa aaa    2367
Asn Ile Ile Lys Asn Arg Ser Leu Pro Leu Lys Glu Lys Arg Lys Lys
    750                 755                 760 cta aaa cag ttt cag aag gaa tat cct ttg ata tat cag aaa aga ttt    2415
Leu Lys Gln Phe Gln Lys Glu Tyr Pro Leu Ile Tyr Gln Lys Arg Phe
765                 770                 775 cca acc acg gag agt gaa gca gca ctt ttt ggt gac aaa cct aca atc    2463
Pro Thr Thr Glu Ser Glu Ala Ala Leu Phe Gly Asp Lys Pro Thr Ile
780                 785                 790                 795 aag caa cca atg ctg att tta aga aaa cca aag ttc cgt agt cta aga    2511
Lys Gln Pro Met Leu Ile Leu Arg Lys Pro Lys Phe Arg Ser Leu Arg
            800                 805                 810 taactaactg aattaaaaat tatgtaatac ttgtggaact ttgataaatg aagccatatc   2571
tgagaatgta gctactcaaa aggaagtctg tcattaataa ggtatttcta aataaacaca   2631
ttatgtaagg aagtgccaaa atagttatca atgtgagact cttaggaaac taactagatc   2691
tcaattgaga gcacataaca atagatgata ccaaatactt tttgttttta acacagctat   2751
ccagtaaggc tatcatgatg tgtgctaaaa ttttatttac ttgaattttg aaaactgagc   2811
tgtgttaggg attaaactat aattctgttc ttaaaagaaa atttatctgc aaatgtgcaa   2871
gttctgagat attagctaat gaattagttg tttggggtta cttctttgtt tctaagtata   2931
agaatgtgaa gaatatttga aaactcaatg aaataattct cagctgccaa atgttgcact   2991
```

```
cttttatata ttcttttcc acttttgatc tatttatata tatgtatgtg ttttaaaat      3051
atgtgtatat tttatcagat ttggttttgc cttaaatatt atccccaatt gcttcagtca      3111
ttcatttgtt cagtatatat attttgaatt ctagttttca taatctatta gaagatgggg      3171
atataaaaga agtataaggc aatcatatat tcattcaaaa gatatttatt tagcaactgc      3231
tatgtgcctt tcgttgttcc agatatgcag agacaatgat aaataaaaca tataatctct      3291
tccataaggt atttattttt taatcaaggg agatacacct atcagatgtt taaaataaca      3351
acactaccca ctgaaatcag ggcatataga atcattcagc taaagagtga cttctatgat      3411
gatggaacag gtctctaagc tagtggtttt caaactggta cacattagac tcacccgagg      3471
aattttaaaa cagcctatat gcccagggcc taacttacac taattaaatc tgaattttgg      3531
ggatgttgta tagggattag tatttttttt aatctaggtg attccaatat tcagccaact      3591
gtgagaatca atggcctaaa tgctttttat aaacattttt ataagtgtca agataatggc      3651
acattgactt tattttttca ttggaagaaa atgcctgcca agtataaatg actctcatct      3711
taaaacaagg ttcttcaggt ttctgcttga ttgacttggt acaaacttga agcaagttgc      3771
cttctaattt ttactccaag attgtttcat atctattcct taagtgtaaa gaaatatata      3831
atgcatggtt tgtaataaaa tcttaatgtt taatgactgt tctcatttct caatgtaatt      3891
tcatactgtt tctctataaa atgatagtat tccatttaac attactgatt tttattaaaa      3951
acctggacag aaaattataa attataaata tgactttatc ctggctataa aattattgaa      4011
ccaaaatgaa ttcttctaa ggcatttgaa tactaaaacg tttattgttt atagatatgt      4071
aaaatgtgga ttatgttgca aattgagatt aaaattattt ggggttttgt aacaatataa      4131
ttttgctttt gtattataga caaatatata aataataaag gcaggcaact ttcatttgca      4191
ctaatgtaca tgcaattgag attacaaaat acatggtaca atgctttaat aacaaactct      4251
gccagtcagg tttgaatcct actgtgctat taactagcta gtaaactcag acaagttact      4311
taacttctct aagccccagt tttgttatct ataaaatgaa tattataata gtacctcttt      4371
ttaggattgc gaggattaag caggataatg catgtaaagt gttagcacag tgtctcacat      4431
agaataagca ctctataaat attttactag aatcacctag gattatagca ctagaagaga      4491
tcttagcaaa aatgtggtcc tttctgttgc tttggacaga catgaaccaa aacaaaatta      4551
cggacaattg atgagcctta ttaactatct tttcattatg agacaaaggt tctgattatg      4611
cctactggtt gaaatttttt aatctagtca agaaggaaaa tttgatgagg aaggaaggaa      4671
tggatatctt cagaagggct tcgcctaagc tggaacatgg atagattcca ttctaacata      4731
aagatcttta agttcaaata tagatgagtt gactggtaga tttggtggta gttgctttct      4791
cgggatataa gaagcaaaat caactgctac aagtaaagag gggatgggga aggtgttgca      4851
catttaaaga gagaaagtgt gaaaaagcct aattgtggga atgcacaggt ttcaccagat      4911
cagatgatgt ctggttattc tgtaaattat agttcttatc ccagaaatta ctgcctccac      4971
catccctaat atcttctaat tggtatcata taatgaccca ctcttcttat gttatccaaa      5031
cagttatgtg gcatttagta atggaatgta catggaattt cccactgact tacctttctg      5091
tccttgggaa gcttaaactc tgaatcttct catctgtaaa atgtgaatta agtatctac      5151
ctaactgagt tgtgattgta gtgaaagaaa ggcaatatat ttaaatcttg aatttagcaa      5211
gcccacgctc gatttttatg tcctttcctc ttgccttgta ttgagtttaa gatctctact      5271
gattaaaact cttttgctat caaaaaaaaa aaaaaaaaa aaaaaaa                    5318
```

<210> SEQ ID NO 4

```
<211> LENGTH: 811
<212> TYPE: PRT
<213> ORGANISM: Homo sapiens

<400> SEQUENCE: 4
```

| | | | | | | | | | | | | | | |
|---|---|---|---|---|---|---|---|---|---|---|---|---|---|---|
| Met | Glu | Ser | Gln | Gly | Val | Pro | Pro | Gly | Pro | Tyr | Arg | Ala | Thr | Lys | Leu |
| 1 | | | | 5 | | | | | 10 | | | | | 15 | |

| Trp | Asn | Glu | Val | Thr | Thr | Ser | Phe | Arg | Ala | Gly | Met | Pro | Leu | Arg | Lys |
| | | | 20 | | | | | 25 | | | | | 30 | | |

| His | Arg | Gln | His | Phe | Lys | Lys | Tyr | Gly | Asn | Cys | Phe | Thr | Ala | Gly | Glu |
| | | | 35 | | | | | 40 | | | | | 45 | | |

| Ala | Val | Asp | Trp | Leu | Tyr | Asp | Leu | Leu | Arg | Asn | Asn | Ser | Asn | Phe | Gly |
| | 50 | | | | | 55 | | | | | 60 | | | | |

| Pro | Glu | Val | Thr | Arg | Gln | Gln | Thr | Ile | Gln | Leu | Leu | Arg | Lys | Phe | Leu |
| 65 | | | | | 70 | | | | | 75 | | | | | 80 |

| Lys | Asn | His | Val | Ile | Glu | Asp | Ile | Lys | Gly | Arg | Trp | Gly | Ser | Glu | Asn |
| | | | | 85 | | | | | 90 | | | | | 95 | |

| Val | Asp | Asp | Asn | Asn | Gln | Leu | Phe | Arg | Phe | Pro | Ala | Thr | Ser | Pro | Leu |
| | | | 100 | | | | | 105 | | | | | 110 | | |

| Lys | Thr | Leu | Pro | Arg | Arg | Tyr | Pro | Glu | Leu | Arg | Lys | Asn | Asn | Ile | Glu |
| | | | | 115 | | | | | 120 | | | | | 125 | |

| Asn | Phe | Ser | Lys | Asp | Lys | Asp | Ser | Ile | Phe | Lys | Leu | Arg | Asn | Leu | Ser |
| | 130 | | | | | 135 | | | | | 140 | | | | |

| Arg | Arg | Thr | Pro | Lys | Arg | His | Gly | Leu | His | Leu | Ser | Gln | Glu | Asn | Gly |
| 145 | | | | | 150 | | | | | 155 | | | | | 160 |

| Glu | Lys | Ile | Lys | His | Glu | Ile | Ile | Asn | Glu | Asp | Gln | Glu | Asn | Ala | Ile |
| | | | | 165 | | | | | 170 | | | | | 175 | |

| Asp | Asn | Arg | Glu | Leu | Ser | Gln | Glu | Asp | Val | Glu | Glu | Val | Trp | Arg | Tyr |
| | | | 180 | | | | | 185 | | | | | 190 | | |

| Val | Ile | Leu | Ile | Tyr | Leu | Gln | Thr | Ile | Leu | Gly | Val | Pro | Ser | Leu | Glu |
| | | | | 195 | | | | | 200 | | | | | 205 | |

| Glu | Val | Ile | Asn | Pro | Lys | Gln | Val | Ile | Pro | Gln | Tyr | Ile | Met | Tyr | Asn |
| | 210 | | | | | 215 | | | | | 220 | | | | |

| Met | Ala | Asn | Thr | Ser | Lys | Arg | Gly | Val | Val | Ile | Leu | Gln | Asn | Lys | Ser |
| 225 | | | | | 230 | | | | | 235 | | | | | 240 |

| Asp | Asp | Leu | Pro | His | Trp | Val | Leu | Ser | Ala | Met | Lys | Cys | Leu | Ala | Asn |
| | | | | 245 | | | | | 250 | | | | | 255 | |

| Trp | Pro | Arg | Ser | Asn | Asp | Met | Asn | Asn | Pro | Thr | Tyr | Val | Gly | Phe | Glu |
| | | | 260 | | | | | 265 | | | | | 270 | | |

| Arg | Asp | Val | Phe | Arg | Thr | Ile | Ala | Asp | Tyr | Phe | Leu | Asp | Leu | Pro | Glu |
| | | | | 275 | | | | | 280 | | | | | 285 | |

| Pro | Leu | Leu | Thr | Phe | Glu | Tyr | Tyr | Glu | Leu | Phe | Val | Asn | Ile | Leu | Val |
| | 290 | | | | | 295 | | | | | 300 | | | | |

| Val | Cys | Gly | Tyr | Ile | Thr | Val | Ser | Asp | Arg | Ser | Ser | Gly | Ile | His | Lys |
| 305 | | | | | 310 | | | | | 315 | | | | | 320 |

| Ile | Gln | Asp | Asp | Pro | Gln | Ser | Ser | Lys | Phe | Leu | His | Leu | Asn | Asn | Leu |
| | | | | 325 | | | | | 330 | | | | | 335 | |

| Asn | Ser | Phe | Lys | Ser | Thr | Glu | Cys | Leu | Leu | Leu | Ser | Leu | Leu | His | Arg |
| | | | 340 | | | | | 345 | | | | | 350 | | |

| Glu | Lys | Asn | Lys | Glu | Glu | Ser | Asp | Ser | Thr | Glu | Arg | Leu | Gln | Ile | Ser |
| | | | | 355 | | | | | 360 | | | | | 365 | |

| Asn | Pro | Gly | Phe | Gln | Glu | Arg | Cys | Ala | Lys | Lys | Met | Gln | Leu | Val | Asn |
| | 370 | | | | | 375 | | | | | 380 | | | | |

| Leu | Arg | Asn | Arg | Arg | Val | Ser | Ala | Asn | Asp | Ile | Met | Gly | Gly | Ser | Cys |
| 385 | | | | | 390 | | | | | 395 | | | | | 400 |

```
His Asn Leu Ile Gly Leu Ser Asn Met His Asp Leu Ser Ser Asn Ser
                405                 410                 415
Lys Pro Arg Cys Cys Ser Leu Glu Gly Ile Val Asp Val Pro Gly Asn
            420                 425                 430
Ser Ser Lys Glu Ala Ser Ser Val Phe His Gln Ser Phe Pro Asn Ile
            435                 440                 445
Glu Gly Gln Asn Asn Lys Leu Phe Leu Glu Ser Lys Pro Lys Gln Glu
    450                 455                 460
Phe Leu Leu Asn Leu His Ser Glu Glu Asn Ile Gln Lys Pro Phe Ser
465                 470                 475                 480
Ala Gly Phe Lys Arg Thr Ser Thr Leu Thr Val Gln Asp Gln Glu Glu
                485                 490                 495
Leu Cys Asn Gly Lys Cys Lys Ser Lys Gln Leu Cys Arg Ser Gln Ser
                500                 505                 510
Leu Leu Leu Arg Ser Ser Thr Arg Arg Asn Ser Tyr Ile Asn Thr Pro
            515                 520                 525
Val Ala Glu Ile Ile Met Lys Pro Asn Val Gly Gln Gly Ser Thr Ser
        530                 535                 540
Val Gln Thr Ala Met Glu Ser Glu Leu Gly Glu Ser Ser Ala Thr Ile
545                 550                 555                 560
Asn Lys Arg Leu Cys Lys Ser Thr Ile Glu Leu Ser Glu Asn Ser Leu
                565                 570                 575
Leu Pro Ala Ser Ser Met Leu Thr Gly Thr Gln Ser Leu Leu Gln Pro
            580                 585                 590
His Leu Glu Arg Val Ala Ile Asp Ala Leu Gln Leu Cys Cys Leu Leu
        595                 600                 605
Leu Pro Pro Pro Asn Arg Arg Lys Leu Gln Leu Leu Met Arg Met Ile
    610                 615                 620
Ser Arg Met Ser Gln Asn Val Asp Met Pro Lys Leu His Asp Ala Met
625                 630                 635                 640
Gly Thr Arg Ser Leu Met Ile His Thr Phe Ser Arg Cys Val Leu Cys
                645                 650                 655
Cys Ala Glu Glu Val Asp Leu Asp Glu Leu Leu Ala Gly Arg Leu Val
            660                 665                 670
Ser Phe Leu Met Asp His His Gln Glu Ile Leu Gln Val Pro Ser Tyr
            675                 680                 685
Leu Gln Thr Ala Val Glu Lys His Leu Asp Tyr Leu Lys Lys Gly His
    690                 695                 700
Ile Glu Asn Pro Gly Asp Gly Leu Phe Ala Pro Leu Pro Thr Tyr Ser
705                 710                 715                 720
Tyr Cys Lys Gln Ile Ser Ala Gln Glu Phe Asp Glu Gln Lys Val Ser
                725                 730                 735
Thr Ser Gln Ala Ala Ile Ala Glu Leu Leu Glu Asn Ile Ile Lys Asn
            740                 745                 750
Arg Ser Leu Pro Leu Lys Glu Arg Lys Lys Leu Lys Gln Phe Gln
            755                 760                 765
Lys Glu Tyr Pro Leu Ile Tyr Gln Lys Arg Phe Pro Thr Thr Glu Ser
    770                 775                 780
Glu Ala Ala Leu Phe Gly Asp Lys Pro Thr Ile Lys Gln Pro Met Leu
785                 790                 795                 800
Ile Leu Arg Lys Pro Lys Phe Arg Ser Leu Arg
            805                 810
```

-continued

```
<210> SEQ ID NO 5
<211> LENGTH: 8666
<212> TYPE: DNA
<213> ORGANISM: Homo sapiens
<220> FEATURE:
<221> NAME/KEY: CDS
<222> LOCATION: (79)..(1659)

<400> SEQUENCE: 5
gagactcgcc actgccgcgg ccgctgggcc tgagtgtcgc cttcgccgcc atggacgcca      60
ccgggcgctg acagacct atg gag agt cag ggt gtg cct ccc ggg cct tat     111
                    Met Glu Ser Gln Gly Val Pro Pro Gly Pro Tyr
                     1               5                  10 cgg gcc acc aag ctg tgg aat gaa gtt acc aca tct ttt cga gca gga     159
Arg Ala Thr Lys Leu Trp Asn Glu Val Thr Thr Ser Phe Arg Ala Gly
             15                  20                  25 atg cct cta aga aaa cac aga caa cac ttt aaa aaa tat ggc aat tgt     207
Met Pro Leu Arg Lys His Arg Gln His Phe Lys Lys Tyr Gly Asn Cys
         30                  35                  40 ttc aca gca gga gaa gca gtg gat tgg ctt tat gac cta tta aga aat     255
Phe Thr Ala Gly Glu Ala Val Asp Trp Leu Tyr Asp Leu Leu Arg Asn
     45                  50                  55 aat agc aat ttt ggt cct gaa gtt aca agg caa cag act atc caa ctg     303
Asn Ser Asn Phe Gly Pro Glu Val Thr Arg Gln Gln Thr Ile Gln Leu
 60                  65                  70                  75 ttg agg aaa ttt ctt aag aat cat gta att gaa gat atc aaa ggg agg     351
Leu Arg Lys Phe Leu Lys Asn His Val Ile Glu Asp Ile Lys Gly Arg
                 80                  85                  90 tgg gga tca gaa aat gtt gat gat aac aac cag ctc ttc aga ttt cct     399
Trp Gly Ser Glu Asn Val Asp Asp Asn Asn Gln Leu Phe Arg Phe Pro
             95                 100                 105 gca act tcg cca ctt aaa act cta cca cga agg tat cca gaa ttg aga     447
Ala Thr Ser Pro Leu Lys Thr Leu Pro Arg Arg Tyr Pro Glu Leu Arg
        110                 115                 120 aaa aac aac ata gag aac ttt tcc aaa gat aaa gat agc att ttt aaa     495
Lys Asn Asn Ile Glu Asn Phe Ser Lys Asp Lys Asp Ser Ile Phe Lys
    125                 130                 135 tta cga aac tta tct cgt aga act cct aaa agg cat gga tta cat tta     543
Leu Arg Asn Leu Ser Arg Arg Thr Pro Lys Arg His Gly Leu His Leu
140                 145                 150                 155 tct cag gaa aat ggc gag aaa ata aag cat gaa ata atc aat gaa gat     591
Ser Gln Glu Asn Gly Glu Lys Ile Lys His Glu Ile Ile Asn Glu Asp
                160                 165                 170 caa gaa aat gca att gat aat aga gaa cta agc cag gaa gat gtt gaa     639
Gln Glu Asn Ala Ile Asp Asn Arg Glu Leu Ser Gln Glu Asp Val Glu
            175                 180                 185 gaa gtt tgg aga tat gtt att ctg atc tac ctg caa acc att tta ggt     687
Glu Val Trp Arg Tyr Val Ile Leu Ile Tyr Leu Gln Thr Ile Leu Gly
        190                 195                 200 gtg cca tcc cta gaa gaa gtc ata aat cca aaa caa gta att ccc caa     735
Val Pro Ser Leu Glu Glu Val Ile Asn Pro Lys Gln Val Ile Pro Gln
    205                 210                 215 tat ata atg tac aac atg gcc aat aca agt aaa cgt gga gta gtt ata     783
Tyr Ile Met Tyr Asn Met Ala Asn Thr Ser Lys Arg Gly Val Val Ile
220                 225                 230                 235 cta caa aac aaa tca gat gac ctc cct cac tgg gta tta tct gcc atg     831
Leu Gln Asn Lys Ser Asp Asp Leu Pro His Trp Val Leu Ser Ala Met
                240                 245                 250 aag tgc cta gca aat tgg cca aga agc aat gat atg aat aat cca act     879
Lys Cys Leu Ala Asn Trp Pro Arg Ser Asn Asp Met Asn Asn Pro Thr
            255                 260                 265
```

| | | | | | | | | | | | | | | | | |
|---|---|---|---|---|---|---|---|---|---|---|---|---|---|---|---|---|
| tat | gtt | gga | ttt | gaa | cga | gat | gta | ttc | aga | aca | atc | gca | gat | tat | ttt | 927 |
| Tyr | Val | Gly | Phe | Glu | Arg | Asp | Val | Phe | Arg | Thr | Ile | Ala | Asp | Tyr | Phe | |
| | | 270 | | | | 275 | | | | 280 | | | | | | |
| cta | gat | ctc | cct | gaa | cct | cta | ctt | act | ttt | gaa | tat | tac | gaa | tta | ttt | 975 |
| Leu | Asp | Leu | Pro | Glu | Pro | Leu | Leu | Thr | Phe | Glu | Tyr | Tyr | Glu | Leu | Phe | |
| 285 | | | | | 290 | | | | | 295 | | | | | | |
| gta | aac | att | ttg | gtt | gtt | tgt | ggc | tac | atc | aca | gtt | tca | gat | aga | tcc | 1023 |
| Val | Asn | Ile | Leu | Val | Val | Cys | Gly | Tyr | Ile | Thr | Val | Ser | Asp | Arg | Ser | |
| 300 | | | | | 305 | | | | | 310 | | | | | 315 | |
| agt | ggg | ata | cat | aaa | att | caa | gat | gat | cca | cag | tct | tca | aaa | ttc | ctt | 1071 |
| Ser | Gly | Ile | His | Lys | Ile | Gln | Asp | Asp | Pro | Gln | Ser | Ser | Lys | Phe | Leu | |
| | | | | 320 | | | | | 325 | | | | | 330 | | |
| cac | tta | aac | aat | ttg | aat | tcc | ttc | aaa | tca | act | gag | tgc | ctt | ctt | ctc | 1119 |
| His | Leu | Asn | Asn | Leu | Asn | Ser | Phe | Lys | Ser | Thr | Glu | Cys | Leu | Leu | Leu | |
| | | 335 | | | | | 340 | | | | | 345 | | | | |
| agt | ctg | ctt | cat | aga | gaa | aaa | aac | aaa | gaa | gaa | tca | gat | tct | act | gag | 1167 |
| Ser | Leu | Leu | His | Arg | Glu | Lys | Asn | Lys | Glu | Glu | Ser | Asp | Ser | Thr | Glu | |
| | | | 350 | | | | | 355 | | | | | 360 | | | |
| aga | cta | cag | ata | agc | aat | cca | gga | ttt | caa | gaa | aga | tgt | gct | aag | aaa | 1215 |
| Arg | Leu | Gln | Ile | Ser | Asn | Pro | Gly | Phe | Gln | Glu | Arg | Cys | Ala | Lys | Lys | |
| | 365 | | | | | 370 | | | | | 375 | | | | | |
| atg | cag | cta | gtt | aat | tta | aga | aac | aga | aga | gtg | agt | gct | aat | gac | ata | 1263 |
| Met | Gln | Leu | Val | Asn | Leu | Arg | Asn | Arg | Arg | Val | Ser | Ala | Asn | Asp | Ile | |
| 380 | | | | | 385 | | | | | 390 | | | | | 395 | |
| atg | gga | gga | agt | tgt | cat | aat | tta | ata | ggg | tta | agt | aat | atg | cat | gat | 1311 |
| Met | Gly | Gly | Ser | Cys | His | Asn | Leu | Ile | Gly | Leu | Ser | Asn | Met | His | Asp | |
| | | | | 400 | | | | | 405 | | | | | 410 | | |
| cta | tcc | tct | aac | agc | aaa | cca | agg | tgc | tgt | tct | ttg | gaa | gga | att | gta | 1359 |
| Leu | Ser | Ser | Asn | Ser | Lys | Pro | Arg | Cys | Cys | Ser | Leu | Glu | Gly | Ile | Val | |
| | | | 415 | | | | | 420 | | | | | 425 | | | |
| gat | gtg | cca | ggg | aat | tca | agt | aaa | gag | gca | tcc | agt | gtc | ttt | cat | caa | 1407 |
| Asp | Val | Pro | Gly | Asn | Ser | Ser | Lys | Glu | Ala | Ser | Ser | Val | Phe | His | Gln | |
| | | 430 | | | | | 435 | | | | | 440 | | | | |
| tct | ttt | ccg | aac | ata | gaa | gga | caa | aat | aat | aaa | ctg | ttt | tta | gag | tct | 1455 |
| Ser | Phe | Pro | Asn | Ile | Glu | Gly | Gln | Asn | Asn | Lys | Leu | Phe | Leu | Glu | Ser | |
| 445 | | | | | 450 | | | | | 455 | | | | | | |
| aag | ccc | aaa | cag | gaa | ttc | ctg | ttg | aat | ctt | cat | tca | gag | gaa | aat | att | 1503 |
| Lys | Pro | Lys | Gln | Glu | Phe | Leu | Leu | Asn | Leu | His | Ser | Glu | Glu | Asn | Ile | |
| 460 | | | | | 465 | | | | | 470 | | | | | 475 | |
| caa | aag | cca | ttc | agt | gct | ggt | ttt | aag | aga | acc | tct | act | ttg | act | gtt | 1551 |
| Gln | Lys | Pro | Phe | Ser | Ala | Gly | Phe | Lys | Arg | Thr | Ser | Thr | Leu | Thr | Val | |
| | | | | 480 | | | | | 485 | | | | | 490 | | |
| caa | gac | caa | gag | gag | ttg | tgt | aat | ggg | aaa | tgc | aag | tca | aaa | cag | ctt | 1599 |
| Gln | Asp | Gln | Glu | Glu | Leu | Cys | Asn | Gly | Lys | Cys | Lys | Ser | Lys | Gln | Leu | |
| | | | | 495 | | | | | 500 | | | | | 505 | | |
| tgt | agg | tct | cag | agt | ttg | ctt | tta | aga | agt | agt | aca | aga | agg | aat | agt | 1647 |
| Cys | Arg | Ser | Gln | Ser | Leu | Leu | Leu | Arg | Ser | Ser | Thr | Arg | Arg | Asn | Ser | |
| | | 510 | | | | | 515 | | | | | 520 | | | | |
| tat | atc | aat | aca | ccagtggctg | | aaattatcat | | gaaaccaaat | | gttggacaag | | | | | | 1699 |
| Tyr | Ile | Asn | Thr | | | | | | | | | | | | | |
| | 525 | | | | | | | | | | | | | | | |

| | |
|---|---|
| gcagcacaag tgtgcaaaca gctatggaaa gtgaactcgg agagtctagt gccacaatca | 1759 |
| ataaaagact ctgcaaaagt acaatagaac tttcagaaaa ttctttactt ccagcttctt | 1819 |
| ctatgttgac tggcacacaa agcttgctgc aacctcattt agagagggtt gccatcgatg | 1879 |
| ctctacagtt atgttgtttg ttacttcccc caccaaatcg tagaaagctt caacttttaa | 1939 |
| tgcgtatgat ttcccgaatg agtcaaaatg ttgatatgcc caaacttcat gatgcaatgg | 1999 |
| gtacgaggtc actgatgata catacccttt ctcgatgtgt gttatgctgt gctgaagaag | 2059 |

```
tggatcttga tgagcttctt gctggaagat tagtttcttt cttaatggat catcatcagg    2119
aaattcttca agtaccctct tacttacaga ctgcagtgga aaaacatctt gactacttaa    2179
aaaagggaca tattgaaaat cctggagatg gactatttgc tcctttgcca acttactcat    2239
actgtaagca gattagtgct caggagtttg atgagcaaaa agtttctacc tctcaagctg    2299
caattgcaga acttttagaa aatattatta aaaacaggag tttacctcta aaggagaaaa    2359
gaaaaaaact aaaacagttt cagaaggaat atcctttgat atatcagaaa agatttccaa    2419
ccacggagag tgaagcagca cttttttggtg acaaacctac aatcaagcaa ccaatgctga    2479
ttttaagaaa accaaagttc cgtagtctaa gataactaac tgaattaaaa attatgtaat    2539
acttgtggaa ctttgataaa tgaagccata tctgagaatg tagctactca aaaggaagtc    2599
tgtcattaat aaggtatttc taaataaaca cattatgtaa ggaagtgcca aaatagttat    2659
caatgtgaga ctcttaggaa actaactaga tctcaattga gagcacataa caatagatga    2719
taccaaatac ttttttgtttt taacacagct atccagtaag gctatcatga tgtgtgctaa    2779
aatttttattt acttgaattt tgaaaactga gctgtgttag ggattaaact ataattctgt    2839
tcttaaaaga aaatttatct gcaaatgtgc aagttctgag atattagcta atgaattagt    2899
tgtttggggt tacttctttg tttctaagta taagaatgtg aagaatattt gaaaactcaa    2959
tgaaataatt ctcagctgcc aaatgttgca ctctttttata tattcttttt ccactttga    3019
tctatttata tatatgtatg tgttttttaaa atatgtgtat attttatcag atttggtttt    3079
gccttaaata ttatccccaa ttgcttcagt cattcatttg ttcagtatat atattttgaa    3139
ttctagttttt cataatctat tagaagatgg ggatataaaa gaagtataag gcaatcatat    3199
attcattcaa aagatattta tttagcaact gctatgtgcc tttcgttgtt ccagatatgc    3259
agagacaatg ataaataaaa catataatct cttccataag gtatttattt tttaatcaag    3319
ggagatacac ctatcagatg tttaaaataa caacactacc cactgaaatc agggcatata    3379
gaatcattca gctaaagagt gacttctatg atgatggaac aggtctctaa gctagtggtt    3439
ttcaaactgg tacacattag actcacccga ggaattttaa aacagcctat atgcccaggg    3499
cctaacttac actaattaaa tctgaatttt ggggatgttg tatagggatt agtatttttt    3559
ttaatctagg tgattccaat attcagccaa ctgtgagaat caatggccta aatgcttttt    3619
ataaacattt ttataagtgt caagataatg gcacattgac tttatttttt cattggaaga    3679
aaatgcctgc caagtataaa tgactctcat cttaaaacaa ggttcttcag gtttctgctt    3739
gattgacttg gtacaaactt gaagcaagtt gccttctaat ttttactcca agattgtttc    3799
atatctattc cttaagtgta aagaaatata taatgcatgg tttgtaataa aatcttaatg    3859
tttaatgact gttctcatttt ctcaatgtaa tttcatactg tttctctata aaatgatagt    3919
attccatttta acattactga ttttttattaa aaacctggac agaaaattat aaattataaa    3979
tatgacttta tcctggctat aaaattattg aaccaaaatg aattctttct aaggcatttg    4039
aatactaaaa cgtttattgt ttatagatat gtaaaatgtg gattatgttg caaattgaga    4099
ttaaaattat ttggggtttt gtaacaatat aattttgctt ttgtattata gacaaatata    4159
taaataataa aggcaggcaa ctttcatttg cactaatgta cgagactcgc cactgccgcg    4219
gccgctgggc ctgagtgtcg ccttcgccgc catggacgcc accgggcgct gacagaccta    4279
tggagagtca gggtgtgcct cccgggcctt atcgggccac caagctgtgg aatgaagtta    4339
ccacatcttt tcgagcagga atgcctctaa gaaaacacag acaacacttt aaaaaatatg    4399
gcaattgttt cacagcagga gaagcagtgg attggcttta tgacctatta agaaataata    4459
```

```
gcaattttgg tcctgaagtt acaaggcaac agactatcca actgttgagg aaatttctta    4519
agaatcatgt aattgaagat atcaaaggga ggtggggatc agaaaatgtt gatgataaca    4579
accagctctt cagatttcct gcaacttcgc cacttaaaac tctaccacga aggtatccag    4639
aattgagaaa aaacaacata gagaactttt ccaaagataa agatagcatt tttaaattac    4699
gaaacttatc tcgtagaact cctaaaaggc atggattaca tttatctcag gaaaatggcg    4759
agaaaataaa gcatgaaata atcaatgaag atcaagaaaa tgcaattgat aatagagaac    4819
taagccagga agatgttgaa gaagtttgga gatatgttat tctgatctac ctgcaaacca    4879 tttttaggtgt gccatcccta gaagaagtca taaatccaaa acaagtaatt ccccaatata    4939
taatgtacaa catggccaat acaagtaaac gtggagtagt tatactacaa aacaaatcag    4999
atgacctccc tcactgggta ttatctgcca tgaagtgcct agcaaattgg ccaagaagca    5059
atgatatgaa taatccaact tatgttggat tgaacgaga tgtattcaga acaatcgcag    5119
attattttct agatctccct gaacctctac ttacttttga atattacgaa ttatttgtaa    5179
acattttggg cttgctgcaa cctcatttag agagggttgc catcgatgct ctacagttat    5239
gttgtttgtt acttcccccca ccaaatcgta gaaagcttca acttttaatg cgtatgattt    5299
cccgaatgag tcaaaatgtt gatatgccca aacttcatga tgcaatgggt acgaggtcac    5359
tgatgataca tacctttttct cgatgtgtgt tatgctgtgc tgaagaagtg gatcttgatg    5419
agcttcttgc tggaagatta gtttctttct taatggatca tcatcaggaa attcttcaag    5479
taccctctta cttacagact gcagtggaaa acatcttga ctactaaaaa aagggacata    5539
ttgaaaatcc tggagatgga ctatttgctc ctttgccaac ttactcatac tgtaagcaga    5599
ttagtgctca ggagtttgat gagcaaaaag tttctacctc tcaagctgca attgcagaac    5659
ttttagaaaa tattattaaa aacaggagtt tacctctaaa ggagaaaaga aaaaaactaa    5719
aacagtttca gaaggaatat cctttgatat atcagaaaag atttccaacc acggagagtg    5779
aagcagcact ttttggtgac aaacctacaa tcaagcaacc aatgctgatt ttaagaaaac    5839
caaagttccg tagtctaaga taactaactg aattaaaaat tatgtaatac ttgtggaact    5899
ttgataaatg aagccatatc tgagaatgta gctactcaaa aggaagtctg tcattaataa    5959
ggtatttcta aataaacaca ttatgtaagg aagtgccaaa atagttatca atgtgagact    6019
cttaggaaac taactagatc tcaattgaga gcacataaca atagatgata ccaaatactt    6079
tttgttttta acacagctat ccagtaaggc tatcatgatg tgtgctaaaa ttttattac    6139 ttgaattttg aaaactgagc tgtgttaggg attaaactat aattctgttc ttaaaagaaa    6199
atttatctgc aaatgtgcaa gttctgagat attagctaat gaattagttg tttggggtta    6259
cttctttgtt tctaagtata agaatgtgaa gaatatttga aaactcaatg aaataattct    6319
cagctgccaa atgttgcact ctttatata ttcttttttcc acttttgatc tatttatata    6379
tatgtatgtg ttttaaaat atgtgtatat tttatcagat ttggttttgc cttaaatatt    6439
atccccaatt gcttcagtca ttcatttgtt cagtatatat attttgaatt ctagttttca    6499
taatctatta gaagatgggg atataaaaga agtataaggc aatcatatat tcattcaaaa    6559
gatatttatt tagcaactgc tatgtgcctt tcgttgttcc agatatgcag agacaatgat    6619
aaataaaaca tataatctct tccataaggt attttattttt taatcaaggg agatacacct    6679
atcagatgtt taaaataaca acactaccca ctgaaatcag ggcatataga atcattcagc    6739
taaagagtga cttctatgat gatggaacag gtctctaagc tagtggtttt caaactggta    6799
cacattagac tcacccgagg aattttaaaa cagcctatat gcccagggcc taacttacac    6859
```

```
taattaaatc tgaattttgg ggatgttgta tagggattag tattttttt aatctaggtg      6919 attccaatat tcagccaact gtgagaatca atggcctaaa tgcttttat aaacattttt      6979 ataagtgtca agataatggc acattgactt tattttttca ttggaagaaa atgcctgcca      7039
agtataaatg actctcatct taaaacaagg ttcttcaggt ttctgcttga ttgacttggt      7099
acaaacttga agcaagttgc cttctaattt ttactccaag attgtttcat atctattcct      7159
taagtgtaaa gaaatatata atgcatggtt tgtaataaaa tcttaatgtt taatgactgt      7219
tctcatttct caatgtaatt tcatactgtt tctctataaa atgatagtat tccatttaac      7279
attactgatt tttattaaaa acctggacag aaaattataa attataaata tgactttatc      7339
ctggctataa aattattgaa ccaaaatgaa ttctttctaa ggcatttgaa tactaaaacg      7399
tttattgttt atagatatgt aaaatgtgga ttatgttgca aattgagatt aaaattattt      7459
ggggttttgt aacaatataa ttttgctttt gtattataga caaatatata aataataaag      7519
gcaggcaact ttcatttgca ctaatgtaca tgcaattgag attacaaaat acatggtaca      7579
atgctttaat aacaaactct gccagtcagg tttgaatcct actgtgctat taactagcta      7639
gtaaactcag acaagttact taacttctct aagccccagt tttgttatct ataaaatgaa      7699
tattataata gtacctcttt ttaggattgc gaggattaag caggataatg catgtaaagt      7759
gttagcacag tgtctcacat agaataagca ctctataaat attttactag aatcacctag      7819
gattatagca ctagaagaga tcttagcaaa aatgtggtcc tttctgttgc tttggacaga      7879
catgaaccaa aacaaaatta cggacaattg atgagcctta ttaactatct tttcattatg      7939
agacaaaggt tctgattatg cctactggtt gaaattttt aatctagtca agaaggaaaa      7999
tttgatgagg aaggaaggaa tggatatctt cagaagggct tcgcctaagc tggaacatgg      8059
atagattcca ttctaacata aagatcttta agttcaaata tagatgagtt gactggtaga      8119
tttggtggta gttgctttct cgggatataa gaagcaaaat caactgctac aagtaaagag      8179
gggatgggga aggtgttgca catttaaaga gagaaagtgt gaaaaagcct aattgtggga      8239
atgcacaggt ttcaccagat cagatgatgt ctggttattc tgtaaattat agttcttatc      8299
ccagaaatta ctgcctccac catccctaat atcttctaat tggtatcata taatgaccca      8359
ctcttcttat gttatccaaa cagttatgtg gcatttagta atggaatgta catggaattt      8419
cccactgact tacctttctg tccttgggaa gcttaaactc tgaatcttct catctgtaaa      8479
atgtgaatta agtatctac ctaactgagt tgtgattgta gtgaaagaaa ggcaatatat      8539
ttaaatcttg aatttagcaa gcccacgctc gattttatg tcctttcctc ttgccttgta      8599
ttgagtttaa gatctctact gattaaaact cttttgctat caaaaaaaaa aaaaaaaaa      8659 aaaaaaa                                                              8666
```

<210> SEQ ID NO 6
<211> LENGTH: 527
<212> TYPE: PRT
<213> ORGANISM: Homo sapiens

<400> SEQUENCE: 6

Met Glu Ser Gln Gly Val Pro Pro Gly Pro Tyr Arg Ala Thr Lys Leu
1               5                   10                  15

Trp Asn Glu Val Thr Thr Ser Phe Arg Ala Gly Met Pro Leu Arg Lys
            20                  25                  30

His Arg Gln His Phe Lys Lys Tyr Gly Asn Cys Phe Thr Ala Gly Glu
        35                  40                  45

Ala Val Asp Trp Leu Tyr Asp Leu Leu Arg Asn Asn Ser Asn Phe Gly

```
                50                    55                    60
Pro Glu Val Thr Arg Gln Gln Thr Ile Gln Leu Leu Arg Lys Phe Leu
 65                  70                  75                  80

Lys Asn His Val Ile Glu Asp Ile Lys Gly Arg Trp Gly Ser Glu Asn
                     85                  90                  95

Val Asp Asp Asn Asn Gln Leu Phe Arg Phe Pro Ala Thr Ser Pro Leu
                    100                 105                 110

Lys Thr Leu Pro Arg Arg Tyr Pro Glu Leu Arg Lys Asn Asn Ile Glu
                115                 120                 125

Asn Phe Ser Lys Asp Lys Asp Ser Ile Phe Lys Leu Arg Asn Leu Ser
            130                 135                 140

Arg Arg Thr Pro Lys Arg His Gly Leu His Leu Ser Gln Glu Asn Gly
145                 150                 155                 160

Glu Lys Ile Lys His Glu Ile Ile Asn Glu Asp Gln Glu Asn Ala Ile
                165                 170                 175

Asp Asn Arg Glu Leu Ser Gln Glu Asp Val Glu Val Trp Arg Tyr
            180                 185                 190

Val Ile Leu Ile Tyr Leu Gln Thr Ile Leu Gly Val Pro Ser Leu Glu
                195                 200                 205

Glu Val Ile Asn Pro Lys Gln Val Ile Pro Gln Tyr Ile Met Tyr Asn
210                 215                 220

Met Ala Asn Thr Ser Lys Arg Gly Val Val Ile Leu Gln Asn Lys Ser
225                 230                 235                 240

Asp Asp Leu Pro His Trp Val Leu Ser Ala Met Lys Cys Leu Ala Asn
                245                 250                 255

Trp Pro Arg Ser Asn Asp Met Asn Asn Pro Thr Tyr Val Gly Phe Glu
                260                 265                 270

Arg Asp Val Phe Arg Thr Ile Ala Asp Tyr Phe Leu Asp Leu Pro Glu
            275                 280                 285

Pro Leu Leu Thr Phe Glu Tyr Tyr Glu Leu Phe Val Asn Ile Leu Val
            290                 295                 300

Val Cys Gly Tyr Ile Thr Val Ser Asp Arg Ser Ser Gly Ile His Lys
305                 310                 315                 320

Ile Gln Asp Asp Pro Gln Ser Ser Lys Phe Leu His Leu Asn Asn Leu
                325                 330                 335

Asn Ser Phe Lys Ser Thr Glu Cys Leu Leu Ser Leu Leu His Arg
                340                 345                 350

Glu Lys Asn Lys Glu Glu Ser Asp Ser Thr Glu Arg Leu Gln Ile Ser
            355                 360                 365

Asn Pro Gly Phe Gln Glu Arg Cys Ala Lys Lys Met Gln Leu Val Asn
    370                 375                 380

Leu Arg Asn Arg Arg Val Ser Ala Asn Asp Ile Met Gly Gly Ser Cys
385                 390                 395                 400

His Asn Leu Ile Gly Leu Ser Asn Met His Asp Leu Ser Ser Asn Ser
                405                 410                 415

Lys Pro Arg Cys Cys Ser Leu Glu Gly Ile Val Asp Val Pro Gly Asn
            420                 425                 430

Ser Ser Lys Glu Ala Ser Ser Val Phe His Gln Ser Phe Pro Asn Ile
        435                 440                 445

Glu Gly Gln Asn Asn Lys Leu Phe Leu Glu Ser Lys Pro Lys Gln Glu
    450                 455                 460

Phe Leu Leu Asn Leu His Ser Glu Glu Asn Ile Gln Lys Pro Phe Ser
465                 470                 475                 480
```

```
Ala Gly Phe Lys Arg Thr Ser Thr Leu Thr Val Gln Asp Gln Glu Glu
            485                 490                 495

Leu Cys Asn Gly Lys Cys Lys Ser Lys Gln Leu Cys Arg Ser Gln Ser
        500                 505                 510

Leu Leu Leu Arg Ser Ser Thr Arg Arg Asn Ser Tyr Ile Asn Thr
    515                 520                 525

<210> SEQ ID NO 7
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 7

Ile Tyr Asn Glu Tyr Ile Tyr Asp Leu
1               5

<210> SEQ ID NO 8
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 8

Ile Tyr Asn Glu Tyr Ile Tyr Asp Leu Phe
1               5                   10

<210> SEQ ID NO 9
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 9

Tyr Ile Tyr Asp Leu Phe Val Pro Val
1               5

<210> SEQ ID NO 10
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 10

Arg Leu Ala Ile Phe Lys Asp Leu Val
1               5

<210> SEQ ID NO 11
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 11

Thr Met Ser Ser Ser Lys Leu Ser Asn Val
1               5                   10

<210> SEQ ID NO 12
<211> LENGTH: 9
<212> TYPE: PRT
<213> ORGANISM: Artificial
<220> FEATURE:
```

<223> OTHER INFORMATION: An artificially synthesized peptide sequence

<400> SEQUENCE: 12

Glu Tyr Tyr Glu Leu Phe Val Asn Ile
1               5

<210> SEQ ID NO 13
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 13

Asp Tyr Ala Asp Leu Lys Glu Lys Leu
1               5

<210> SEQ ID NO 14
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 14

Gln Tyr Glu Arg Ala Cys Lys Asp Leu
1               5

<210> SEQ ID NO 15
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 15

Cys Tyr Leu Ala Tyr Asp Glu Thr Leu
1               5

<210> SEQ ID NO 16
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 16

Ala Tyr Asp Glu Thr Leu Asn Val Leu
1               5

<210> SEQ ID NO 17
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 17

Gly Tyr Lys Asp Glu Asn Asn Arg Leu
1               5

<210> SEQ ID NO 18
<211> LENGTH: 9
<212> TYPE: PRT
<213> ORGANISM: Artificial
<220> FEATURE:
<223> OTHER INFORMATION: An artificially synthesized peptide sequence

```
<400> SEQUENCE: 18

Leu Tyr Gly Ser Leu Thr Asn Ser Leu
1               5

<210> SEQ ID NO 19
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 19

Lys Tyr Ala Glu Asp Arg Glu Arg Phe
1               5

<210> SEQ ID NO 20
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 20

Asn Tyr Asp Ile Ala Ile Ala Glu Leu
1               5

<210> SEQ ID NO 21
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 21

Cys Tyr Lys Ala Lys Ile Lys Glu Leu
1               5

<210> SEQ ID NO 22
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 22

Asp Tyr Leu Gln Val Cys Leu Arg Ile
1               5

<210> SEQ ID NO 23
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 23

Lys Phe Asn Gln Ile Lys Ala Glu Leu
1               5

<210> SEQ ID NO 24
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 24
```

```
Ser Tyr Val Phe Ser Ala Asp Pro Ile
1               5
```

<210> SEQ ID NO 25
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 25

```
Ala Tyr Arg Leu Leu Lys Leu Gly Ile
1               5
```

<210> SEQ ID NO 26
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 26

```
Asp Tyr Glu Gln Ala Asn Leu Asn Met
1               5
```

<210> SEQ ID NO 27
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 27

```
Asn Phe Asp Gly Ile Lys Leu Asp Leu
1               5
```

<210> SEQ ID NO 28
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 28

```
Leu Phe Val Pro Val Ser Ser Lys Phe
1               5
```

<210> SEQ ID NO 29
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 29

```
Leu Phe Asp Ser Leu Gln Glu Arg Leu
1               5
```

<210> SEQ ID NO 30
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 30

```
Lys Phe Ser Val Trp Val Ser Phe Phe
1               5
```

```
<210> SEQ ID NO 31
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 31

Lys Leu Leu Asp Leu Ile Glu Asp Leu
1               5

<210> SEQ ID NO 32
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 32

Arg Phe Pro Lys Pro Glu Leu Glu Ile
1               5

<210> SEQ ID NO 33
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 33

Lys Tyr Asn Ala Asp Arg Lys Lys Trp
1               5

<210> SEQ ID NO 34
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 34

Arg Thr Gln Asn Leu Lys Ala Asp Leu
1               5

<210> SEQ ID NO 35
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 35

Lys Trp Leu Glu Glu Lys Met Met Leu
1               5

<210> SEQ ID NO 36
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 36

Lys Ser Asn Glu Met Glu Glu Asp Leu
1               5
```

```
<210> SEQ ID NO 37
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 37

Lys Ile Glu Asp Gly Ser Val Val Leu
1               5

<210> SEQ ID NO 38
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 38

Lys Gln Gln Asn Glu Met Glu Ile Leu
1               5

<210> SEQ ID NO 39
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 39

Lys Thr Gln Asn Glu Gly Glu Arg Leu
1               5

<210> SEQ ID NO 40
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 40

Lys Trp Lys Glu Lys Cys Asn Asp Leu
1               5

<210> SEQ ID NO 41
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 41

Lys Ile Lys Glu Leu Glu Thr Ile Leu
1               5

<210> SEQ ID NO 42
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 42

Phe Leu Leu Thr Ile Glu Asn Glu Leu
1               5

<210> SEQ ID NO 43
<211> LENGTH: 9
```

```
<212> TYPE: PRT
<213> ORGANISM: Artificial
<220> FEATURE:
<223> OTHER INFORMATION: An artificially synthesized peptide sequence

<400> SEQUENCE: 43

Ser Ser Leu Ile Ile Asn Asn Lys Leu
1               5

<210> SEQ ID NO 44
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 44

Lys Leu Thr Asn Leu Gln Asp Glu Leu
1               5

<210> SEQ ID NO 45
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 45

Ile Met Gln Pro Val Lys Asp Leu Leu
1               5

<210> SEQ ID NO 46
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 46

Lys Tyr Asn Ala Asp Arg Lys Lys Trp Leu
1               5                   10

<210> SEQ ID NO 47
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 47

Lys Tyr Ala Glu Asp Arg Glu Arg Phe Phe
1               5                   10

<210> SEQ ID NO 48
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 48

Gln Tyr Trp Ala Gln Arg Glu Ala Asp Phe
1               5                   10

<210> SEQ ID NO 49
<211> LENGTH: 10
<212> TYPE: PRT
<213> ORGANISM: Artificial
```

```
<220> FEATURE:
<223> OTHER INFORMATION: An artificially synthesized peptide sequence

<400> SEQUENCE: 49

Leu Tyr Thr Ser Glu Ile Ser Ser Pro Ile
1               5                   10

<210> SEQ ID NO 50
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 50

Lys Phe Gln Lys Arg Lys Met Leu Arg Leu
1               5                   10

<210> SEQ ID NO 51
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 51

Ala Phe Leu Leu Thr Ile Glu Asn Glu Leu
1               5                   10

<210> SEQ ID NO 52
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 52

Thr Tyr Ser Leu Arg Ser Gln Ala Ser Ile
1               5                   10

<210> SEQ ID NO 53
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 53

Asp Phe Leu Gln His Ser Pro Ser Ile Leu
1               5                   10

<210> SEQ ID NO 54
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 54

Arg Thr Leu Asn Val Leu Phe Asp Ser Leu
1               5                   10

<210> SEQ ID NO 55
<211> LENGTH: 10
<212> TYPE: PRT
<213> ORGANISM: Artificial
<220> FEATURE:
<223> OTHER INFORMATION: An artificially synthesized peptide sequence
```

-continued

```
<400> SEQUENCE: 55

Lys Gln Ile Val His Phe Gln Gln Glu Leu
1               5                   10

<210> SEQ ID NO 56
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 56

Lys Leu Leu Arg Ile Lys Ile Asn Glu Leu
1               5                   10

<210> SEQ ID NO 57
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 57

Lys Ile Ile Glu Asp Met Arg Met Thr Leu
1               5                   10

<210> SEQ ID NO 58
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 58

Arg Thr Ile Gln Gln Leu Lys Glu Gln Leu
1               5                   10

<210> SEQ ID NO 59
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 59

Lys Val Glu Cys Ser His Ser Ala Lys Leu
1               5                   10

<210> SEQ ID NO 60
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 60

Lys Asn Glu Lys Glu Glu Lys Ala Glu Leu
1               5                   10

<210> SEQ ID NO 61
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 61
```

```
Lys Leu Ile Asn Glu Lys Lys Glu Lys Leu
1               5                   10

<210> SEQ ID NO 62
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 62

Lys Leu Met His Thr Lys Ile Asp Glu Leu
1               5                   10

<210> SEQ ID NO 63
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 63

Arg Val Leu Gln Glu Asn Asn Glu Gly Leu
1               5                   10

<210> SEQ ID NO 64
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 64

Arg Val Ile Arg Val Ser Glu Leu Ser Leu
1               5                   10

<210> SEQ ID NO 65
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 65

Arg Asn Leu Lys Glu Phe Gln Glu His Leu
1               5                   10

<210> SEQ ID NO 66
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 66

Glu Tyr Ile Tyr Asp Leu Phe Val Pro Val
1               5                   10

<210> SEQ ID NO 67
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 67

Lys Met Leu Arg Leu Ser Gln Asp Val
```

```
<210> SEQ ID NO 68
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 68

Ala Leu Leu Arg Gln Ile Lys Glu Val
1               5

<210> SEQ ID NO 69
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 69

Ala Leu Ser Glu Leu Thr Gln Gly Val
1               5

<210> SEQ ID NO 70
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 70

Lys Leu Gly Ile Lys His Gln Ser Val
1               5

<210> SEQ ID NO 71
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 71

Thr Leu Gln Lys Phe Gly Asp Phe Leu
1               5

<210> SEQ ID NO 72
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 72

Lys Leu Thr Asp Ala Lys Lys Gln Ile
1               5

<210> SEQ ID NO 73
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 73

Gln Leu Thr Glu Lys Asp Ser Asp Leu
1               5
```

<210> SEQ ID NO 74
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 74

Asn Leu Gln Asp Met Lys His Leu Leu
1               5

<210> SEQ ID NO 75
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 75

Ser Val Trp Val Ser Phe Phe Glu Ile
1               5

<210> SEQ ID NO 76
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 76

Phe Gln Gly Cys Ile Met Gln Pro Val
1               5

<210> SEQ ID NO 77
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 77

Val Leu Gln Glu Asn Asn Glu Gly Leu
1               5

<210> SEQ ID NO 78
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 78

Thr Leu Asp Val Gln Ile Gln His Val
1               5

<210> SEQ ID NO 79
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 79

Ala Ile Trp Glu Glu Cys Lys Glu Ile
1               5

<210> SEQ ID NO 80

```
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 80

Phe Leu Gln His Ser Pro Ser Ile Leu
1               5

<210> SEQ ID NO 81
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 81

Asp Leu Met Glu Asp Glu Asp Leu Val
1               5

<210> SEQ ID NO 82
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 82

Ser Leu Leu Thr Leu Gly Lys Cys Ile
1               5

<210> SEQ ID NO 83
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 83

Gly Ile Leu Pro Arg Thr Leu Asn Val
1               5

<210> SEQ ID NO 84
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 84

Ile Leu Pro Arg Thr Leu Asn Val Leu
1               5

<210> SEQ ID NO 85
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 85

Lys Ile Cys Ser Glu Arg Lys Arg Val
1               5

<210> SEQ ID NO 86
<211> LENGTH: 9
<212> TYPE: PRT
```

```
<213> ORGANISM: Artificial
<220> FEATURE:
<223> OTHER INFORMATION: An artificially synthesized peptide sequence

<400> SEQUENCE: 86

Ser Leu Ser Glu Lys Lys Asn Leu Thr
1               5

<210> SEQ ID NO 87
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 87

Leu Met His Thr Lys Ile Asp Glu Leu
1               5

<210> SEQ ID NO 88
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 88

Trp Leu Glu Glu Lys Met Met Leu Ile
1               5

<210> SEQ ID NO 89
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 89

Thr Leu Asn Val Leu Lys Phe Ser Ala
1               5

<210> SEQ ID NO 90
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 90

Lys Leu Gln Thr Glu Pro Leu Ser Thr
1               5

<210> SEQ ID NO 91
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 91

Cys Ile Met Gln Pro Val Lys Asp Leu
1               5

<210> SEQ ID NO 92
<211> LENGTH: 9
<212> TYPE: PRT
<213> ORGANISM: Artificial
<220> FEATURE:
```

```
<223> OTHER INFORMATION: An artificially synthesized peptide sequence

<400> SEQUENCE: 92

Lys Gln Val Gln Lys Glu Val Ser Val
1               5

<210> SEQ ID NO 93
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 93

Lys Leu Lys Glu Glu Ile Thr Gln Leu
1               5

<210> SEQ ID NO 94
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 94

Thr Leu Ser Lys Glu Val Gln Gln Ile
1               5

<210> SEQ ID NO 95
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 95

Asn Glu Tyr Ile Tyr Asp Leu Phe Val
1               5

<210> SEQ ID NO 96
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 96

Leu Leu Asp Glu Asp Leu Asp Lys Thr
1               5

<210> SEQ ID NO 97
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 97

Leu Ala Tyr Asp Glu Thr Leu Asn Val
1               5

<210> SEQ ID NO 98
<211> LENGTH: 9
<212> TYPE: PRT
<213> ORGANISM: Artificial
<220> FEATURE:
<223> OTHER INFORMATION: An artificially synthesized peptide sequence
```

```
<400> SEQUENCE: 98

Asn Leu Pro Asn Thr Gln Leu Asp Leu
1               5

<210> SEQ ID NO 99
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 99

Thr Leu Gly Lys Cys Ile Asn Val Leu
1               5

<210> SEQ ID NO 100
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 100

Thr Leu Asn Val Leu Phe Asp Ser Leu
1               5

<210> SEQ ID NO 101
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 101

Lys Leu Ser Asn Glu Ile Glu Thr Ala
1               5

<210> SEQ ID NO 102
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 102

Lys Glu His Glu Asn Asn Thr Asp Val
1               5

<210> SEQ ID NO 103
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 103

Asp Leu Leu Gly Asn Asp Tyr Leu Val
1               5

<210> SEQ ID NO 104
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 104
```

```
Lys Ile Met Lys Leu Ser Asn Glu Ile
1               5

<210> SEQ ID NO 105
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 105

Ile Leu Gln Ser Lys Ala Lys Lys Ile
1               5

<210> SEQ ID NO 106
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 106

Ile Leu Asn Val Lys Arg Ala Thr Ile
1               5

<210> SEQ ID NO 107
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 107

Lys Glu Leu Glu Thr Ile Leu Glu Thr
1               5

<210> SEQ ID NO 108
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 108

Ile Val Asn Ile Ser Gln Cys Tyr Leu
1               5

<210> SEQ ID NO 109
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 109

Leu Ile Cys Asn Glu Thr Val Glu Val
1               5

<210> SEQ ID NO 110
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 110

Thr Leu Leu Gln Glu Arg Glu Ile Leu
1               5
```

```
<210> SEQ ID NO 111
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 111

Thr Leu Glu Glu Asn Lys Ala Phe Ile
1               5

<210> SEQ ID NO 112
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 112

Tyr Asn Ala Asp Arg Lys Lys Trp Leu
1               5

<210> SEQ ID NO 113
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 113

Lys Gly Tyr Ser Phe Ile Lys Asp Leu
1               5

<210> SEQ ID NO 114
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 114

Lys Met Ala Val Lys His Pro Gly Cys
1               5

<210> SEQ ID NO 115
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 115

Ser Glu Met Ser Arg Val Ile Arg Val
1               5

<210> SEQ ID NO 116
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 116

Gln Leu Thr Asn Asn Leu Gln Asp Met
1               5
```

```
<210> SEQ ID NO 117
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 117

Gln Ile Val His Phe Gln Gln Glu Leu
1               5

<210> SEQ ID NO 118
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 118

Asn Ile Ser Glu Phe Glu Glu Ser Ile
1               5

<210> SEQ ID NO 119
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 119

Thr Leu Asn Ser Ser Gln Glu Lys Leu
1               5

<210> SEQ ID NO 120
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 120

Ser Leu Ile Ile Asn Asn Lys Leu Ile
1               5

<210> SEQ ID NO 121
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 121

Leu Ile Asn Glu Lys Lys Glu Lys Leu
1               5

<210> SEQ ID NO 122
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 122

Lys Leu Leu Asp Glu Asp Leu Asp Lys Thr
1               5                   10

<210> SEQ ID NO 123
<211> LENGTH: 10
```

```
<212> TYPE: PRT
<213> ORGANISM: Artificial
<220> FEATURE:
<223> OTHER INFORMATION: An artificially synthesized peptide sequence

<400> SEQUENCE: 123

Tyr Leu Ala Tyr Asp Glu Thr Leu Asn Val
1               5                   10

<210> SEQ ID NO 124
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 124

Asn Met Ala Asn Ser Ile Lys Phe Ser Val
1               5                   10

<210> SEQ ID NO 125
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 125

Val Leu Phe Asp Ser Leu Gln Glu Arg Leu
1               5                   10

<210> SEQ ID NO 126
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 126

Lys Leu Ile Cys Asn Glu Thr Val Glu Val
1               5                   10

<210> SEQ ID NO 127
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 127

Lys Leu Asp Leu Ser His Glu Phe Ser Leu
1               5                   10

<210> SEQ ID NO 128
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 128

Leu Leu Thr Leu Gly Lys Cys Ile Asn Val
1               5                   10

<210> SEQ ID NO 129
<211> LENGTH: 10
<212> TYPE: PRT
<213> ORGANISM: Artificial
```

```
<220> FEATURE:
<223> OTHER INFORMATION: An artificially synthesized peptide sequence

<400> SEQUENCE: 129

Gln Val Leu Glu Ala Lys Leu Glu Glu Val
1               5                   10

<210> SEQ ID NO 130
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 130

Ser Leu Ser Glu Lys Lys Asn Leu Thr Leu
1               5                   10

<210> SEQ ID NO 131
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 131

Thr Leu Tyr Gly Ser Leu Thr Asn Ser Leu
1               5                   10

<210> SEQ ID NO 132
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 132

Ala Ile Trp Glu Glu Cys Lys Glu Ile Val
1               5                   10

<210> SEQ ID NO 133
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 133

Leu Leu Asp Glu Asp Leu Asp Lys Thr Leu
1               5                   10

<210> SEQ ID NO 134
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 134

Val Thr Leu Asp Val Gln Ile Gln His Val
1               5                   10

<210> SEQ ID NO 135
<211> LENGTH: 10
<212> TYPE: PRT
<213> ORGANISM: Artificial
<220> FEATURE:
<223> OTHER INFORMATION: An artificially synthesized peptide sequence
```

```
<400> SEQUENCE: 135

Lys Thr Leu Glu Glu Asn Lys Ala Phe Ile
1               5                   10

<210> SEQ ID NO 136
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 136

Gly Leu Thr Asn Ser Gly Lys Thr Tyr Thr
1               5                   10

<210> SEQ ID NO 137
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 137

Asn Ile Ala Glu Ile Glu Asp Ile Arg Val
1               5                   10

<210> SEQ ID NO 138
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 138

Ser Leu Gln Glu Arg Leu Tyr Thr Lys Met
1               5                   10

<210> SEQ ID NO 139
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 139

Gln Gln Ile Glu Lys Leu Gln Ala Glu Val
1               5                   10

<210> SEQ ID NO 140
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 140

Gln Gln Tyr Glu Arg Ala Cys Lys Asp Leu
1               5                   10

<210> SEQ ID NO 141
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 141
```

Met Ile Val Asn Ile Ser Gln Cys Tyr Leu
1               5                   10

<210> SEQ ID NO 142
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 142

Lys Leu Ser Asn Glu Ile Glu Thr Ala Thr
1               5                   10

<210> SEQ ID NO 143
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 143

Lys Gln Ile Lys Gln Val Gln Lys Glu Val
1               5                   10

<210> SEQ ID NO 144
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 144

Asn Leu Pro Asn Thr Gln Leu Asp Leu Leu
1               5                   10

<210> SEQ ID NO 145
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 145

Gln Leu Asp Leu Leu Gly Asn Asp Tyr Leu
1               5                   10

<210> SEQ ID NO 146
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 146

Met Met Leu Ile Thr Gln Ala Lys Glu Ala
1               5                   10

<210> SEQ ID NO 147
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 147

Gln Ile Met Asp Ile Lys Pro Lys Arg Ile

```
                1               5                   10

<210> SEQ ID NO 148
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 148

Gln Leu Val Ala Ala Leu Glu Ile Gln Leu
1               5                   10

<210> SEQ ID NO 149
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 149

Thr Leu Asn Val Leu Lys Phe Ser Ala Ile
1               5                   10

<210> SEQ ID NO 150
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 150

Lys Ile Leu Asn Val Lys Arg Ala Thr Ile
1               5                   10

<210> SEQ ID NO 151
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 151

Thr Leu Glu Glu Gln Glu Gln Thr Gln Val
1               5                   10

<210> SEQ ID NO 152
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 152

Arg Val Ser Glu Leu Ser Leu Cys Asp Leu
1               5                   10

<210> SEQ ID NO 153
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 153

Val Val Leu Asp Ser Cys Glu Val Ser Thr
1               5                   10
```

<210> SEQ ID NO 154
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 154

Tyr Ser Phe Ile Lys Asp Leu Gln Trp Ile
1               5                   10

<210> SEQ ID NO 155
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 155

Ser Ile Phe Thr Val Lys Ile Leu Gln Ile
1               5                   10

<210> SEQ ID NO 156
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 156

Thr Leu Asp Val Gln Ile Gln His Val Val
1               5                   10

<210> SEQ ID NO 157
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 157

Gly Thr Leu Gln Lys Phe Gly Asp Phe Leu
1               5                   10

<210> SEQ ID NO 158
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 158

Phe Ile Lys Asp Leu Gln Trp Ile Gln Val
1               5                   10

<210> SEQ ID NO 159
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 159

Thr Leu Ile Gln Gln Leu Lys Glu Glu Leu
1               5                   10

<210> SEQ ID NO 160

```
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 160

Thr Ile Leu Glu Thr Gln Lys Val Glu Cys
1               5                   10

<210> SEQ ID NO 161
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 161

Ala Ala Leu Glu Ile Gln Leu Lys Ala Leu
1               5                   10

<210> SEQ ID NO 162
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 162

Gly Ile Leu Pro Arg Thr Leu Asn Val Leu
1               5                   10

<210> SEQ ID NO 163
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 163

Tyr Tyr Glu Leu Phe Val Asn Ile Leu
1               5

<210> SEQ ID NO 164
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 164

Tyr Phe Leu Asp Leu Pro Glu Pro Leu
1               5

<210> SEQ ID NO 165
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 165

Arg Tyr Pro Glu Leu Arg Lys Asn Asn
1               5

<210> SEQ ID NO 166
<211> LENGTH: 9
<212> TYPE: PRT
```

```
<213> ORGANISM: Artificial
<220> FEATURE:
<223> OTHER INFORMATION: An artificially synthesized peptide sequence

<400> SEQUENCE: 166

Ser Phe Lys Ser Thr Glu Cys Leu Leu
1               5

<210> SEQ ID NO 167
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 167

Lys Gln Leu Cys Arg Ser Gln Ser Leu
1               5

<210> SEQ ID NO 168
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 168

Val Phe Arg Thr Ile Ala Asp Tyr Phe
1               5

<210> SEQ ID NO 169
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 169

His Phe Lys Lys Tyr Gly Asn Cys Phe
1               5

<210> SEQ ID NO 170
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 170

Gly Tyr Ile Thr Val Ser Asp Arg Ser
1               5

<210> SEQ ID NO 171
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 171

Leu Phe Val Asn Ile Leu Gly Leu Leu
1               5

<210> SEQ ID NO 172
<211> LENGTH: 10
<212> TYPE: PRT
<213> ORGANISM: Artificial
<220> FEATURE:
```

<223> OTHER INFORMATION: An artificially synthesized peptide sequence

<400> SEQUENCE: 172

Glu Tyr Tyr Glu Leu Phe Val Asn Ile Leu
1               5                   10

<210> SEQ ID NO 173
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 173

Asp Tyr Phe Leu Asp Leu Pro Glu Pro Leu
1               5                   10

<210> SEQ ID NO 174
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 174

Arg Tyr Pro Glu Leu Arg Lys Asn Asn Ile
1               5                   10

<210> SEQ ID NO 175
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 175

Glu Tyr Pro Leu Ile Tyr Gln Lys Arg Phe
1               5                   10

<210> SEQ ID NO 176
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 176

Thr Tyr Val Gly Phe Glu Arg Asp Val Phe
1               5                   10

<210> SEQ ID NO 177
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 177

Ser Tyr Ile Asn Thr Pro Val Ala Glu Ile
1               5                   10

<210> SEQ ID NO 178
<211> LENGTH: 10
<212> TYPE: PRT
<213> ORGANISM: Artificial
<220> FEATURE:
<223> OTHER INFORMATION: An artificially synthesized peptide sequence

```
<400> SEQUENCE: 178

Tyr Phe Leu Asp Leu Pro Glu Pro Leu Leu
1               5                   10

<210> SEQ ID NO 179
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 179

Arg Tyr Val Ile Leu Ile Tyr Leu Gln Thr
1               5                   10

<210> SEQ ID NO 180
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 180

Ser Phe Lys Ser Thr Glu Cys Leu Leu Leu
1               5                   10

<210> SEQ ID NO 181
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 181

Leu Phe Arg Phe Pro Ala Thr Ser Pro Leu
1               5                   10

<210> SEQ ID NO 182
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 182

Val Phe Arg Thr Ile Ala Asp Tyr Phe Leu
1               5                   10

<210> SEQ ID NO 183
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 183

Lys Thr Leu Pro Arg Arg Tyr Pro Glu Leu
1               5                   10

<210> SEQ ID NO 184
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 184
```

```
Arg Thr Ile Ala Asp Tyr Phe Leu Asp Leu
1               5                   10
```

<210> SEQ ID NO 185
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 185

```
Gly Phe Glu Arg Asp Val Phe Arg Thr Ile
1               5                   10
```

<210> SEQ ID NO 186
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 186

```
Arg Thr Pro Lys Arg His Gly Leu His Leu
1               5                   10
```

<210> SEQ ID NO 187
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 187

```
Lys Gln Leu Cys Arg Ser Gln Ser Leu Leu
1               5                   10
```

<210> SEQ ID NO 188
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 188

```
Lys Ser Thr Glu Cys Leu Leu Leu Ser Leu
1               5                   10
```

<210> SEQ ID NO 189
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 189

```
Tyr Tyr Glu Leu Phe Val Asn Ile Leu Val
1               5                   10
```

<210> SEQ ID NO 190
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 190

```
Asn Phe Ser Lys Asp Lys Asp Ser Ile Phe
1               5                   10
```

```
<210> SEQ ID NO 191
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 191

Phe Leu Met Asp His His Gln Glu Ile
1               5

<210> SEQ ID NO 192
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 192

Leu Leu Gln Pro His Leu Glu Arg Val
1               5

<210> SEQ ID NO 193
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 193

Ser Leu Leu Pro Ala Ser Ser Met Leu
1               5

<210> SEQ ID NO 194
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 194

Trp Val Leu Ser Ala Met Lys Cys Leu
1               5

<210> SEQ ID NO 195
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 195

Leu Leu Met Arg Met Ile Ser Arg Met
1               5

<210> SEQ ID NO 196
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 196

Ser Met Leu Thr Gly Thr Gln Ser Leu
1               5
```

```
<210> SEQ ID NO 197
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 197

Leu Leu Thr Phe Glu Tyr Tyr Glu Leu
1               5

<210> SEQ ID NO 198
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 198

Tyr Ile Met Tyr Asn Met Ala Asn Thr
1               5

<210> SEQ ID NO 199
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 199

Phe Leu Asp Leu Pro Glu Pro Leu Leu
1               5

<210> SEQ ID NO 200
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 200

Ala Leu Phe Gly Asp Lys Pro Thr Ile
1               5

<210> SEQ ID NO 201
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 201

Met Leu Thr Gly Thr Gln Ser Leu Leu
1               5

<210> SEQ ID NO 202
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 202

Leu Ile Tyr Gln Lys Arg Phe Pro Thr
1               5

<210> SEQ ID NO 203
<211> LENGTH: 9
```

```
<212> TYPE: PRT
<213> ORGANISM: Artificial
<220> FEATURE:
<223> OTHER INFORMATION: An artificially synthesized peptide sequence

<400> SEQUENCE: 203

Thr Leu Pro Arg Arg Tyr Pro Glu Leu
1               5

<210> SEQ ID NO 204
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 204

Lys Gln Phe Gln Lys Glu Tyr Pro Leu
1               5

<210> SEQ ID NO 205
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 205

Ile Met Gly Gly Ser Cys His Asn Leu
1               5

<210> SEQ ID NO 206
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 206

Tyr Glu Leu Phe Val Asn Ile Leu Val
1               5

<210> SEQ ID NO 207
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 207

Thr Ile Ala Asp Tyr Phe Leu Asp Leu
1               5

<210> SEQ ID NO 208
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 208

Ala Leu Gln Leu Cys Cys Leu Leu Leu
1               5

<210> SEQ ID NO 209
<211> LENGTH: 9
<212> TYPE: PRT
<213> ORGANISM: Artificial
```

```
<220> FEATURE:
<223> OTHER INFORMATION: An artificially synthesized peptide sequence

<400> SEQUENCE: 209

Arg Leu Cys Lys Ser Thr Ile Glu Leu
1               5

<210> SEQ ID NO 210
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 210

Gln Leu Cys Arg Ser Gln Ser Leu Leu
1               5

<210> SEQ ID NO 211
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 211

Val Ile Leu Ile Tyr Leu Gln Thr Ile
1               5

<210> SEQ ID NO 212
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 212

Glu Leu Phe Val Asn Ile Leu Val Val
1               5

<210> SEQ ID NO 213
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 213

Ile Leu Gln Asn Lys Ser Asp Asp Leu
1               5

<210> SEQ ID NO 214
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 214

Lys Leu Gln Leu Leu Met Arg Met Ile
1               5

<210> SEQ ID NO 215
<211> LENGTH: 9
<212> TYPE: PRT
<213> ORGANISM: Artificial
<220> FEATURE:
<223> OTHER INFORMATION: An artificially synthesized peptide sequence
```

```
<400> SEQUENCE: 215

Met Ile Ser Arg Met Ser Gln Asn Val
1               5

<210> SEQ ID NO 216
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 216

Thr Ile Gln Leu Leu Arg Lys Phe Leu
1               5

<210> SEQ ID NO 217
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 217

Cys Ser Leu Glu Gly Ile Val Asp Val
1               5

<210> SEQ ID NO 218
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 218

Leu Val Val Cys Gly Tyr Ile Thr Val
1               5

<210> SEQ ID NO 219
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 219

Tyr Ile Asn Thr Pro Val Ala Glu Ile
1               5

<210> SEQ ID NO 220
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 220

Ile Leu Ile Tyr Leu Gln Thr Ile Leu
1               5

<210> SEQ ID NO 221
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 221
```

Lys Ser Asp Asp Leu Pro His Trp Val
1               5

<210> SEQ ID NO 222
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 222

Leu Leu Pro Ala Ser Ser Met Leu Thr
1               5

<210> SEQ ID NO 223
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 223

Met Ile His Thr Phe Ser Arg Cys Val
1               5

<210> SEQ ID NO 224
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 224

Leu Met Ile His Thr Phe Ser Arg Cys
1               5

<210> SEQ ID NO 225
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 225

Cys Val Leu Cys Cys Ala Glu Glu Val
1               5

<210> SEQ ID NO 226
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 226

Glu Leu Phe Val Asn Ile Leu Gly Leu
1               5

<210> SEQ ID NO 227
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 227

Leu Leu Ala Gly Arg Leu Val Ser Phe Leu

```
<210> SEQ ID NO 228
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 228

Phe Leu Met Asp His His Gln Glu Ile Leu
1               5                   10

<210> SEQ ID NO 229
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 229

Ser Leu Leu Gln Pro His Leu Glu Arg Val
1               5                   10

<210> SEQ ID NO 230
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 230

Ile Leu Val Val Cys Gly Tyr Ile Thr Val
1               5                   10

<210> SEQ ID NO 231
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 231

Leu Thr Phe Glu Tyr Tyr Glu Leu Phe Val
1               5                   10

<210> SEQ ID NO 232
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 232

Ile Leu Gly Val Pro Ser Leu Glu Glu Val
1               5                   10

<210> SEQ ID NO 233
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 233

Leu Ile Tyr Leu Gln Thr Ile Leu Gly Val
1               5                   10
```

```
<210> SEQ ID NO 234
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 234

Tyr Leu Gln Thr Ala Val Glu Lys His Leu
1               5                   10

<210> SEQ ID NO 235
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 235

Leu Met Ile His Thr Phe Ser Arg Cys Val
1               5                   10

<210> SEQ ID NO 236
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 236

Ser Met Leu Thr Gly Thr Gln Ser Leu Leu
1               5                   10

<210> SEQ ID NO 237
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 237

Arg Met Ile Ser Arg Met Ser Gln Asn Val
1               5                   10

<210> SEQ ID NO 238
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 238

Gln Leu Leu Met Arg Met Ile Ser Arg Met
1               5                   10

<210> SEQ ID NO 239
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 239

Val Leu Cys Cys Ala Glu Glu Val Asp Leu
1               5                   10

<210> SEQ ID NO 240
```

```
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 240

Ser Leu Met Ile His Thr Phe Ser Arg Cys
1               5                   10

<210> SEQ ID NO 241
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 241

Ser Leu Leu Pro Ala Ser Ser Met Leu Thr
1               5                   10

<210> SEQ ID NO 242
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 242

Tyr Glu Leu Phe Val Asn Ile Leu Val Val
1               5                   10

<210> SEQ ID NO 243
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 243

Gln Leu Cys Arg Ser Gln Ser Leu Leu Leu
1               5                   10

<210> SEQ ID NO 244
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 244

Lys Gln Phe Gln Lys Glu Tyr Pro Leu Ile
1               5                   10

<210> SEQ ID NO 245
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 245

Ile Leu Gln Val Pro Ser Tyr Leu Gln Thr
1               5                   10

<210> SEQ ID NO 246
<211> LENGTH: 10
<212> TYPE: PRT
```

-continued

```
<213> ORGANISM: Artificial
<220> FEATURE:
<223> OTHER INFORMATION: An artificially synthesized peptide sequence

<400> SEQUENCE: 246

Val Gly Phe Glu Arg Asp Val Phe Arg Thr
1               5                   10

<210> SEQ ID NO 247
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 247

Gln Leu Val Asn Leu Arg Asn Arg Arg Val
1               5                   10

<210> SEQ ID NO 248
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 248

Phe Leu Asp Leu Pro Glu Pro Leu Leu Thr
1               5                   10

<210> SEQ ID NO 249
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 249

Ile Met Gly Gly Ser Cys His Asn Leu Ile
1               5                   10

<210> SEQ ID NO 250
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 250

Leu Ile Gly Leu Ser Asn Met His Asp Leu
1               5                   10

<210> SEQ ID NO 251
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 251

Leu Ile Tyr Gln Lys Arg Phe Pro Thr Thr
1               5                   10

<210> SEQ ID NO 252
<211> LENGTH: 10
<212> TYPE: PRT
<213> ORGANISM: Artificial
<220> FEATURE:
```

```
<223> OTHER INFORMATION: An artificially synthesized peptide sequence

<400> SEQUENCE: 252

Thr Leu Thr Val Gln Asp Gln Glu Glu Leu
1               5                   10

<210> SEQ ID NO 253
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 253

Asn Met Ala Asn Thr Ser Lys Arg Gly Val
1               5                   10

<210> SEQ ID NO 254
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 254

Tyr Glu Leu Phe Val Asn Ile Leu Gly Leu
1               5                   10

<210> SEQ ID NO 255
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 255

Asn Ile Leu Gly Leu Leu Gln Pro His Leu
1               5                   10
```

PEPTIDE VACCINES FOR CANCERS EXPRESSING MPHOSPH1 OR DEPDC1 POLYPEPTIDES

This application is a divisional of U.S. patent application Ser. No. 12/445,729, having a 371(c) date of Oct. 16, 2009, which is a U.S. National Stage Application of PCT/JP2007/001122, filed Oct. 16, 2007, which claims the benefit of U.S. Provisional Application No. 60/852,575, filed Oct. 17, 2006. The entire contents of each of the aforementioned applications are incorporated by reference herein.

TECHNICAL FIELD

This application includes a Sequence Listing as a text file named "87331-010130US-843990_SEQLIST.txt" created Jun. 26, 2012, and containing 139,840 bytes. The material contained in this text file is incorporated by reference in its entirety for all purposes.

The present invention relates to the field of biological science, more specifically to the field of cancer therapy. In particular, the present invention relates to novel peptides that serve as extremely effective cancer vaccines, and drugs for treating and preventing tumors containing such peptides.

BACKGROUND ART

It has been demonstrated that $CD8^+$ cytotoxic T lymphocytes (CTLs) recognize epitope peptides derived from tumor-associated antigens (TAAs) presented on MHC class I molecules, and lyse the tumor cells. Since the discovery of the MAGE family as the first example of TAAs, many other TAAs have been discovered using immunological approaches (Boon T. (1993) Int J Cancer 54: 177-80; Boon T. et al., (1996) J Exp Med 183: 725-9; van der Bruggen P et al., (1991) Science 254: 1643-7; Brichard V et al., (1993) J Exp Med 178: 489-95; Kawakami Y et al., (1994) J Exp Med 180: 347-52). Some of them are now in clinical development as targets of immunotherapy. TAAs discovered so far include MAGE (van der Bruggen P et al., (1991) Science 254: 1643-7), gp100 (Kawakami Y et al., (1994) J Exp Med 180: 347-52), SART (Shichijo S et al., (1998) J Exp Med 187:277-88), and NY-ESO-1 (Chen Y. T. et al., (1997) Proc. Natl. Acd. Sci. USA, 94: 1914-8). On the other hand, certain gene products demonstrated to be somewhat specifically over-expressed in tumor cells have been shown to be recognized as targets for inducing cellular immune responses. Such gene products include p53 (Umano Y et al., (2001) Br J Cancer, 84:1052-7), HER2/neu (Tanaka H et al., (2001) Br J Cancer, 84: 94-9), CEA (Nukaya I et al., (1999) Int. J. Cancer 80, 92-7) and the like.

Despite significant progress in basic and clinical research concerning TAAs (Rosenberg S A et al., (1998) Nature Med, 4: 321-7; Mukherji B. et al., (1995) Proc Natl Acad Sci USA, 92: 8078-82: Hu X et al., (1996) Cancer Res, 56: 2479-83), only a very limited number of candidate TAAs suitable for treatment of cancers are presently available. TAAs that are abundantly expressed in cancer cells, and whose expression is restricted to cancer cells, would be promising candidates as immunotherapeutic targets.

Both HLA-A24 and HLA-A0201 are common HLA alleles in the Japanese and Caucasian populations (Date Y et al., (1996) Tissue Antigens 47: 93-101; Kondo A et al., (1995) J Immunol 155: 4307-12; Kubo R T et al., (1994) J Immunol 152: 3913-24; Imanishi et al., Proceeding of the eleventh International Histocompatibility Workshop and Conference Oxford University Press, Oxford, 1065 (1992); Williams F et al., (1997) Tissue Antigen 49: 129-33). Thus, antigenic peptides of cancers presented by these HLA alleles may find particular utility in the treatment of cancers among Japanese and Caucasian patients. Further, it is known that the induction of low-affinity CTL in vitro usually results from exposure to high concentrations of peptide, generating a high level of specific peptide/MHC complexes on antigen-presenting cells (APCs), which can effectively activate these CTL (Alexander-Miller et al., (1996) Proc Natl Acad Sci USA 93: 4102-7).

Recent developments in cDNA microarray technologies have enabled the construction of comprehensive profiles of gene expression of malignant cells as compared to normal cells (Okabe, H. et al., (2001) Cancer Res., 61, 2129-37; Lin Y M. et al., (2002) Oncogene, 21; 4120-8; Hasegawa S. et al., (2002) Cancer Res 62:7012-7). This approach enables an understanding of the complex nature of cancer cells and the mechanisms of carcinogenesis and facilitates the identification of genes whose expression is deregulated in tumors (Bienz M. et al., (2000) Cell 103, 311-20). Among the transcripts identified as up-regulated in cancers, MPHOSPH1 (M-phase phosphoprotein 1; GenBank Accession No. NM_016195; SEQ ID Nos.1, 2), and DEPDC1 (DEP domain containing 1; GenBank Accession No. BM683578) have been recently discovered. See WO 2004/031413, WO 2006/085684 and WO 2007/013,665, the entire contents of which are incorporated by reference herein. DEPDC1 has been described in the context of two different transcriptional variants—DEPDC1 V1 (SEQ ID Nos.3, 4) and DEPDC1 V2 (SEQ ID Nos: 5, 6). These genes have been shown to be specifically up-regulated in tumor cells of the various cancer tissues of the cases analyzed (see below); however, Northern blot analyses demonstrate that these gene products are not found in normal vital organs (see PCT/JP2006/302684). In that immunogenic peptides derived from MPHOSPH1, and DEPDC1 may find utility in killing tumor cells expressing those antigens, these genes are of particular interest to the present inventors.

Since cytotoxic drugs, such as M-VAC, often cause severe adverse reactions, it is clear that thoughtful selection of novel target molecules on the basis of well-characterized mechanisms of action is important in the development of effective anti-cancer drugs having a minimized risk of negative side effects. Toward this goal, the inventors previously performed expression profile analysis on various cancers and normal human tissue, and discovered multiple genes that are specifically over-expressed in cancer (Lin Y M, et al., Oncogene. 2002 Jun. 13; 21:4120-8; Kitahara O, et al., Cancer Res. 2001 May 1; 61:3544-9; Suzuki C, et al., Cancer Res. 2003 Nov. 1; 63:7038-41; Ashida S, Cancer Res. 2004 Sep. 1; 64:5963-72; Ochi K, et al., Int J. Oncol. 2004 March; 24(3):647-55; Kaneta Y, et al., Int J. Oncol. 2003 September; 23:681-91; Obama K, Hepatology. 2005 June; 41:1339-48; Kato T, et al., Cancer Res. 2005 Jul. 1; 65:5638-46; Kitahara O, et al., Neoplasia. 2002 July-August; 4:295-303; Saito-Hisaminato A et al., DNA Res 2002, 9: 35-45). Of these, MPHOSPH1 (in house No. C2093) and DEPDC1 (in house No. B5860N) were identified genes over-expressed in various cancers. In particular, MPHOSPH1 was identified as over-expressed in bladder cancer, breast cancer, cervical cancer, cholangincellular carcinoma, CML, colorectal cancer, gastric cancer, NSCLC, lymphoma, osteosarcoma, prostate cancer, renal carcinoma, soft tissue tumor. Similarly, DEPDC1 was identified as over-expressed in bladder cancer, breast cancer, cervical cancer, cholangincellular carcinoma, CML, NSCLC, lymphoma, osteosarcoma, prostate cancer, SCLC, soft tissue tumor MPHOSPH1 was previously identified as one of the proteins specifically phosphorylated at the G2/M transition and characterized as a plus-end-directed kinesin related protein (Abaza A et al., J Biol Chem 2003, 278: 27844-52). More particularly, MPHOSPH1 has been previously documented to be a plus-end-directed molecular motor that plays a crucial role in cytokinesis, and accumulates in the midzone of the spindle during anaphase to telophase in HeLa cells (Abaza A et al., J Biol Chem 2003, 278: 27844-52; Kamimoto T et al., J Biol Chem 2001, 276: 37520-8). The MPHOSPH1 cDNA encodes a 1780-amino acid protein that is composed of three domains: an NH2-kinasin motor domain, a central coiled coil-stalk domain, and a C-globular tail domain. Together, this data suggests that MPHOSPH1 is an NH2-type kinesin-related protein.

As for DEPDC1, its function remains unclear. The DEP domain contained in this protein is also found in Dishevelled, Egl-10, and Pleckstrin. The DEP domain in *Drosophila* dishevelled plays an essential role in rescue planar polarity defects and induces JNK signaling; nevertheless, its function in Humans has not yet been clarified. However, as disclosed in PCT/JP2006/302684, DEPDC1 siRNAs can suppress the growth of cancer cells. These results demonstrate that DEPDC1 plays an important role in growth of most cancer cells.

SUMMARY OF THE INVENTION

As noted above, MPHOSPH1 (M-phase phosphoprotein 1), and DEPDC1 (DEP domain containing 1) have been identified as up-regulated in various cancers. More particularly, the genes were identified using gene expression profiling with a genome-wide cDNA microarray. As discussed above, expression of MPHOSPH1 and DEPDC1 has been shown to be specifically up-regulated in various tumor cells, including lung cancer and bladder cancer. As described in Table 1, MPHOSPH1 expression was shown to be validly elevated in 30 out of 31 bladder cancers, 8 out of 36 breast cancers, 18 out of 18 cervical cancers, 5 out of 17 cholangincellular carcinomas, 25 out of 31 CMLs, 6 out of 11 colorectal cancers, 6 out of 14 gastric cancers, 5 out of 5 NSCLCs, 7 out of 7 lymphomas, 6 out of 10 osteosarcomas, 7 out of 22 prostate cancers, 10 out of 18 renal carcinomas and 15 out of 21 soft tissue tumors. At the same time, DEPDC1 expression was shown to be validly elevated in 23 out of 25 bladder cancers, 6 out of 13 breast cancers, 12 out of 12 cervical cancers, 6 out of 6 cholangincellular carcinomas, 3 out of 4 CMLs 2 out of 4 colorectal cancers, 6 out of 6 NSCLCs, 7 out of 7 lymphomas, 10 out of 14 osteosarcomas, 11 out of 24 prostate cancers, 14 out of 14 SCLCs and 22 out of 31 soft tissue tumors as described in Table 1.

The present invention is based, at least in part, on the identification of specific epitope peptides of the gene products of these genes (MPHOSPH1 and DEPDC1) which possess the ability to induce cytotoxic T lymphocytes (CTLs) specific to the corresponding molecules. As discussed in detail below, Peripheral Blood Mononuclear Cells (PBMC) of healthy donor were stimulated using HLA-A*2402 and HLA-A*0201 binding candidate peptides derived from MPHOSPH1 or DEPDC1. CTL clones and/or lines were then established with specific cytotoxicity against the HLA-A24 or HLA-A2 positive target cells pulsed with each of the candidate peptides. These results demonstrate that these peptides are HLA-A24 or HLA-A2 restricted epitope peptides that can induce potent and specific immune responses against cells expressing MPHOSPH1 or DEPDC1.

Accordingly, the present invention provides methods for treating or preventing a disease associated with the over-expression of MPHOSPH1 and/or DEPDC1, e.g. cancer. Such methods involves the step of administering to a subject in need thereof a MPHOSPH1 and/or DEPDC1 polypeptide of the invention. Administration of such peptide(s) results in the induction of anti-tumor immunity. Thus, the present invention provides methods for inducing anti-tumor immunity in a subject, such methods involving the step of administering to the subject a MPHOSPH1 and/or DEPDC1 polypeptide, as well as pharmaceutical compositions for treating or preventing a disease associated with the over-expression of MPHOSPH1 and/or DEPDC1, e.g cancer, that include the MPHOSPH1 and/or DEPDC1 polypeptides. Exemplary cancers include, but are not limited to, bladder cancer, breast cancer, cervical cancer, cholangincellular carcinoma, CML, colorectal cancer, gastric cancer, NSCLC, lymphoma, osteosarcoma, prostate cancer, renal carcinoma, SCLC, and soft tissue tumor.

That is, the present application includes following embodiments, and any combinations thereof.

[1] An isolated peptide having cytotoxic T cell inducibility, wherein said peptide derived from amino acid sequence of SEQ ID NO: 2, 4, or 6.

[2] An isolated peptide of less than about 15 amino acids selected from the group consisting of peptides comprising the amino acid sequences of SEQ ID NO: 7, 8 and 12, or a peptide having cytotoxic T cell inducibility, wherein said peptide comprises an amino acid sequence selected from the group consisting of SEQ ID NO: 7, 8 and 12, wherein 1, 2, or several amino acids are substituted, deleted, or added.

[3] The peptide having cytotoxic T cell inducibility of [2], wherein the second amino acid from the N-terminus is phenylalanine, tyrosine, methionine, or tryptophan.

[4] The peptide having cytotoxic T cell inducibility of [2], wherein the C-terminal amino acid is phenylalanine, leucine, isoleucine, tryptophan, or methionine.

[5] An isolated peptide of less than about 15 amino acids selected from the group consisting of peptides comprising the amino acid sequences of SEQ ID NO: 9, 10, 11, 192, 195, 197, 209, 225, 226, 228, 230, 240, 241, 243, 244, 253, 254 and 255, or a peptide having cytotoxic T cell inducibility, wherein said peptide comprises an amino acid sequence selected from the group consisting of SEQ ID NO: 9, 10, 11, 192, 195, 197, 209, 225, 226, 228, 230, 240, 241, 243, 244, 253, 254 and 255, wherein 1, 2, or several amino acids are substituted, deleted, or added.

[6] The peptide having cytotoxic T cell inducibility of [5], wherein the second amino acid from the N-terminus is leucine or methionine.

[7] The peptide having cytotoxic T cell inducibility of [5], wherein the C-terminal amino acid is valine or leucine.

[8] A vector in which the DNA encodes peptides of any one of [1] to [7].

[9] A pharmaceutical composition for treating or preventing a disease associated with over-expression of the genes of SEQ ID NO: 1, 3 and/or 5, said composition comprising one or more peptides of any one of [1] to [7].

[10] The pharmaceutical composition of [9], wherein the disease is cancer.

[11] The pharmaceutical composition of [10], wherein the cancer is selected from the group consisting of bladder cancer, breast cancer, cervical cancer, cholangincellular carcinoma, CML, colorectal cancer, gastric cancer, NSCLC, lymphoma, osteosarcoma, prostate cancer, renal carcinoma, SCLC and soft tissue tumor.

[12] An exosome that presents on its surface a complex comprising a peptide of any one of [1] to [7] and an HLA antigen.

[13] The exosome of [12], wherein the HLA antigen is HLA-A24.

[14] The exosome of [13], wherein the HLA antigen is HLA-A2402.

[15] The exosome of [12], wherein the HLA antigen is HLA-A2.

[16] The exosome of [13], wherein the HLA antigen is HLA-A0201.

[17] A method of inducing antigen-presenting cells having a high cytotoxic T cell inducibility comprising the step of contacting an antigen-presenting cell with a peptide of any one of [1] to [7].

[18] A method of inducing cytotoxic T cells by contacting a T cell with a peptide of any one of [1] to [7].

[19] A method of inducing antigen-presenting cells having high cytotoxic T cell inducibility, said method comprising the step of transferring a gene comprising a polynucleotide encoding a peptide of any one of [1] to [7] to an antigen-presenting cell.

[20] An isolated cytotoxic T cell, which is induced by contacting a T cell with a peptide of any one of [1] to [7] or which is transduced with the nucleic acids encoding the TCR subunits polypeptides binding with a peptide of any one of [1] to [7] in the context of HLA-A24 or HLA-A2.

[21] An antigen-presenting cell, which comprises a complex formed between an HLA antigen and a peptide of any one of [1] to [7].

[22] The antigen-presenting cell of [21], induced by the method of [17].

[23] A vaccine for inhibiting proliferation of cells expressing genes of SEQ ID NO: 1, 3 and/or 5, wherein the vaccine comprises a peptide of any one of [1] to [7] as the active ingredient.

[24] The vaccine of [23], wherein the cell is a cancer cell.

[25] The vaccine of [24], wherein the cancer is selected from the group consisting of bladder cancer, breast cancer, cervical cancer, cholangincellular carcinoma, CML, colorectal cancer, gastric cancer, NSCLC, lymphoma, osteosarcoma, prostate cancer, renal carcinoma, SCLC and soft tissue tumor.

[26] The vaccine of [23], formulated for administration to a subject whose HLA antigen is HLA-A24 or HLA-A2.

[27] A method of treating or preventing a disease associated with the over-expression of the genes of SEQ ID NO: 1, 3 and/or 5 in a subject comprising administering to said subject a vaccine comprising one or more peptide of any one of [1] to [7], an immunologically active fragment thereof, or a polynucleotide encoding said peptide or immunologically active fragment.

[28] The method of [27], wherein the disease is cancer.

[29] The method of [28], wherein the cancer is selected from the group consisting of bladder cancer, breast cancer, cervical cancer, cholangincellular carcinoma, CML, colorectal cancer, gastric cancer, NSCLC, lymphoma, osteosarcoma, prostate cancer, renal carcinoma, SCLC and soft tissue tumor.

Alternatively, the present invention also relates to a method of inducing cytotoxic T cells comprising the step of contacting a T-cell with the antigen-presenting cell produced by the method of [19].

These and other objects and features of the invention will become more fully apparent when the following detailed description is read in conjunction with the accompanying figures and examples. However, it is to be understood that both the foregoing summary of the invention and the following detailed description are of preferred embodiments, and not restrictive of the invention or other alternate embodiments of the invention.

BRIEF DESCRIPTION OF THE DRAWINGS

FIG. 1A depicts the results of an IFN-gamma ELISPOT assay for the screening of epitope peptides which, in turn, demonstrate that MPHOSPH1-A24-9-278 (SEQ ID NO: 7) is a potent producer of IFN-gamma. CTLs for those peptides derived from MPHOSHP1 were generated according to the protocols described in "Materials and Methods" section of the examples below. Resulting CTLs having detectable specific CTL activity are shown. In particular, the cells in the well number #4 stimulated with MPHOSPH1-A24-9-278 showed potent IFN-gamma production to recognize peptide pulsed target cells, as compared to the control. FIG. 1B depicts the results of the IFN-gamma ELISPOT assay for the screening of CTL clones after limiting dilution (MPHOSPH1-A24-9-278 CTL clone). The cells in the positive well were expanded and limiting dilution was performed. As the depicted results demonstrate, CTL clones having higher specific CTL activities against the peptide-pulsed target as compared to the activities against target without peptide pulse were established.

FIG. 2A depicts the results of an IFN-gamma ELISPOT assay for the screening of epitope peptides cytotoxicity, which, in turn, demonstrate that MPHOSPH1-A24-10-278 (SEQ ID NO: 8) is a potent producer of IFN-gamma. CTLs for those peptides derived from MPHOSHP1 were generated according to the protocols described in "Materials and Methods" section of the examples below. Resulting CTLs having detectable specific CTL activity are shown. In particular, the cells in the well number #8 stimulated with MPHOSPH1-A24-10-278 showed potent IFN-gamma production as compared to the control. FIG. 2B depicts the results of an IFN-gamma ELISPOT assay for the screening of CTL clones after limiting dilution (MPHOSPH1-A24-10-278 CTL clone). The cells in the positive well were expanded and limiting dilution was performed. As the depicted results demonstrate, CTL clones having higher specific CTL activities against the MPHOSPH1-A24-10-278-pulsed target as compared to the activities against target without peptide pulse as shown were established.

R means Responder: CTL clone.

S means Stimulator: peptide-pulsed A24-LCL ($1 \times 10^4$/well).

Figure 4:
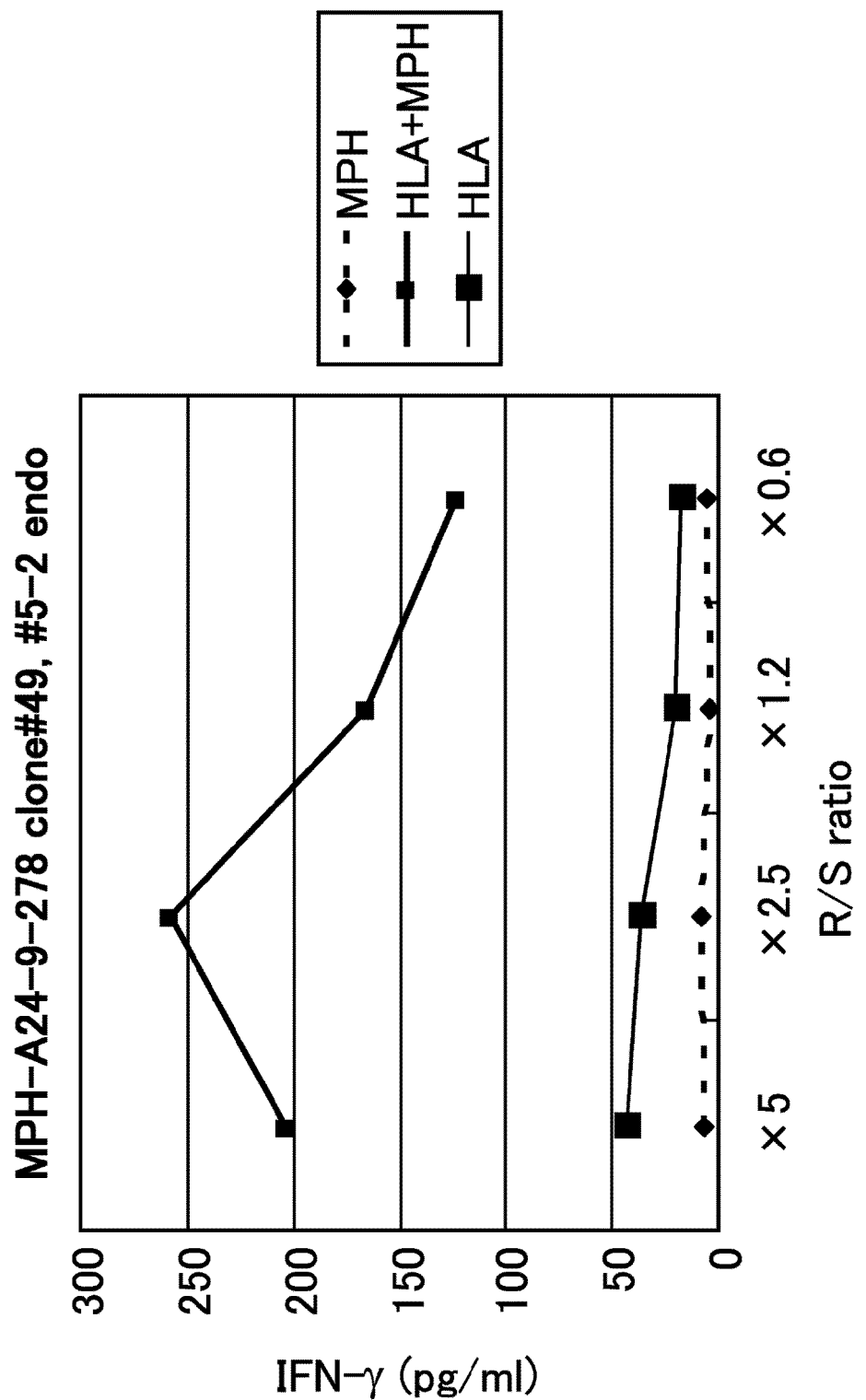

FIG. 4 depicts the expression of MPHOSPH1-A24-9-278 (SEQ ID NO: 7) on the target cell surface with HLA-A24. Specific CTL activity against COS7 transfected both with the full length MPHOSPH1 gene and the HLA-A*2402 molecule was assayed using as effector cells the CTL clone raised by MPHOSPH1-A24-9-278. COS7 transfected with full length MPHOSPH1 but not HLA-A*2402 and COS7 transfected with HLA-A*2402 but not full length MPHOSPH1 were prepared as controls. The CTL clone demonstrated high specific CTL activity against COS7 transfected with both MPHOSPH1 and HLA-A24. However, it did not show significant specific CTL activity against COS7 transfected neither MPHOSPH1 nor HLA-A24.

R means Responder: CTL clone.
S means Stimulator: COS7 transfectant (1×10$^4$/well).

Figure 5:
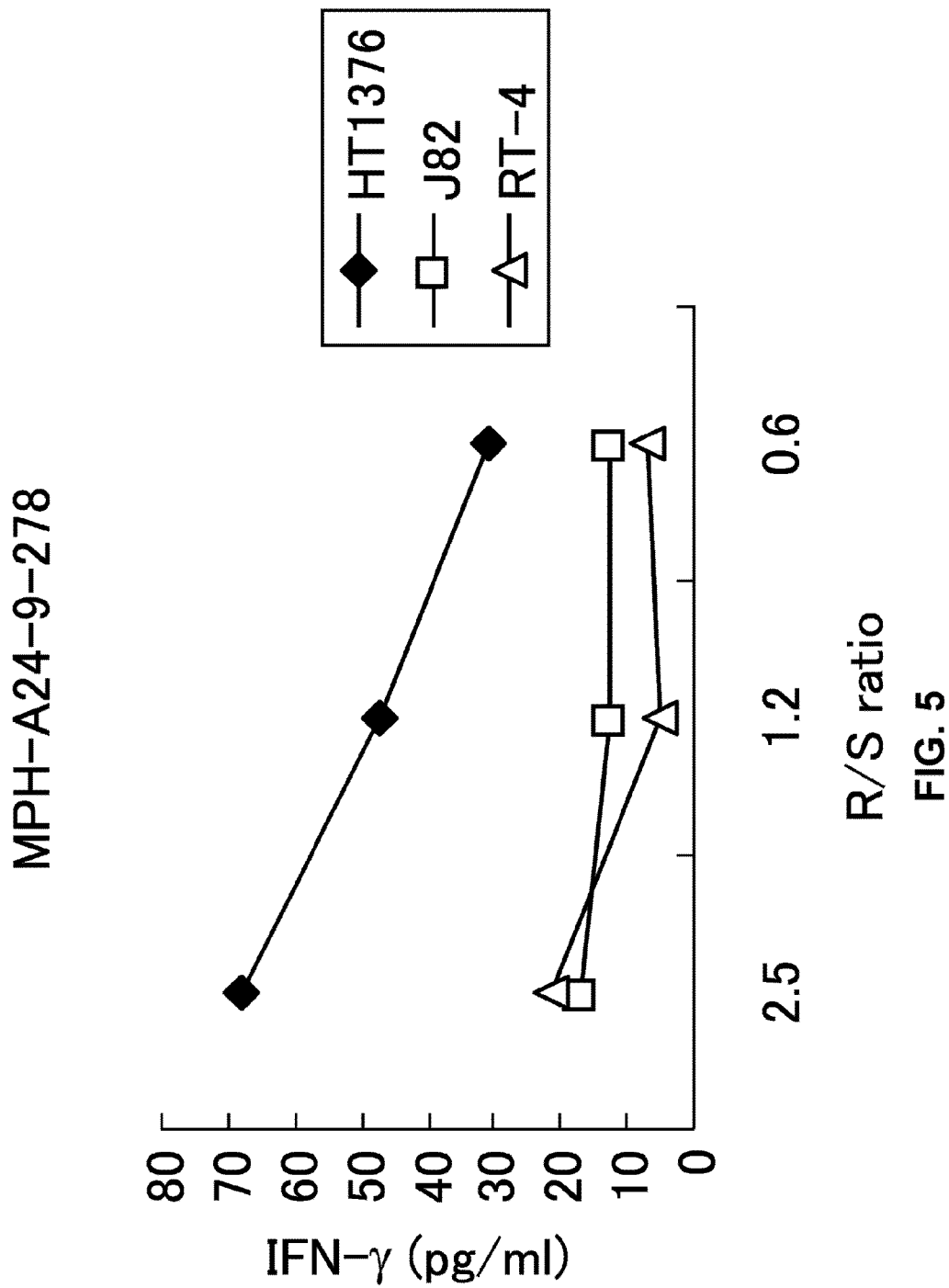

FIG. 5 depicts the CTL activity against bladder cancer cell lines endogenously expressing MPHOSPH1. The established CTL clone induced with MPHOSPH1-A24-9-278 peptide recognized tumor cells endogenously expressing MPHOSPH1. HT1376, RT-4 and J82 cells expressed MPHOSPH1 endogenously, respectively. CTL clone showed IFN-gamma production against HT1376 which have HLA-A*2402 genotype, but no showing response against RT-4 and J82, does not have HLA-A*2402 genotype.

Figure 6:
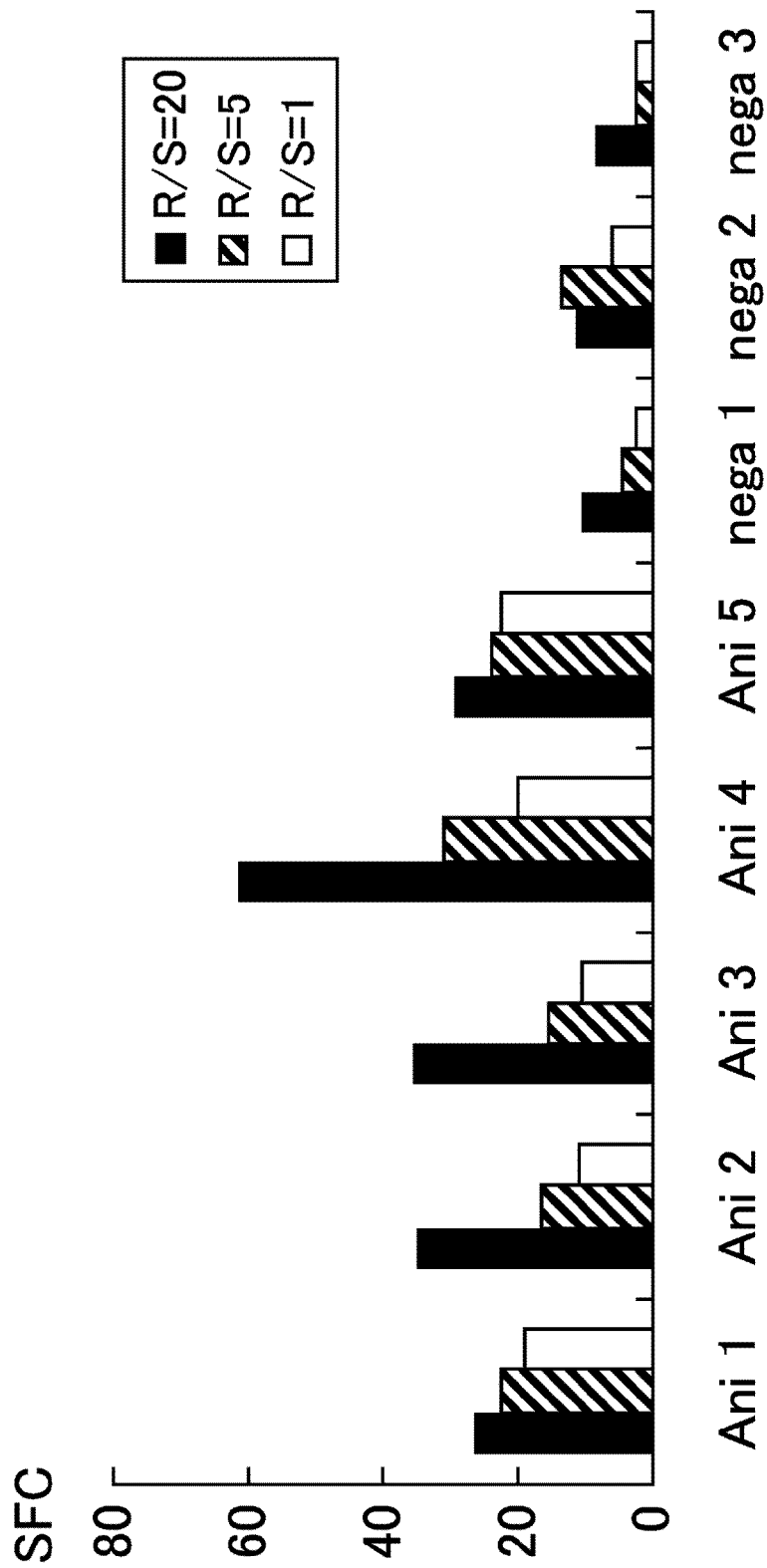

FIG. 6 depicts in vivo immunogenicity analysis using MPHOSPH1-A24-9-278 peptide. IFA-conjugated peptide was injected subcutaneously into BALB/c mice on days 0 and 7. On day 14, splenocytes of vaccinated mice were harvested and used as responder cells, and 1×10$^4$ RLmale1 cells pulsed MPHOSPH1-A24-9-278 peptide were used as stimulator cells for IFN-gamma ELISPOT assay. Spot forming counts (SFC) were indicated in cases of each mice; five mice (Ani1~Ani5) were vaccinated epitope peptide and three mice (nega1~nega3) were injected Mock IFA emulsion as a negative control.

Figure 7A:
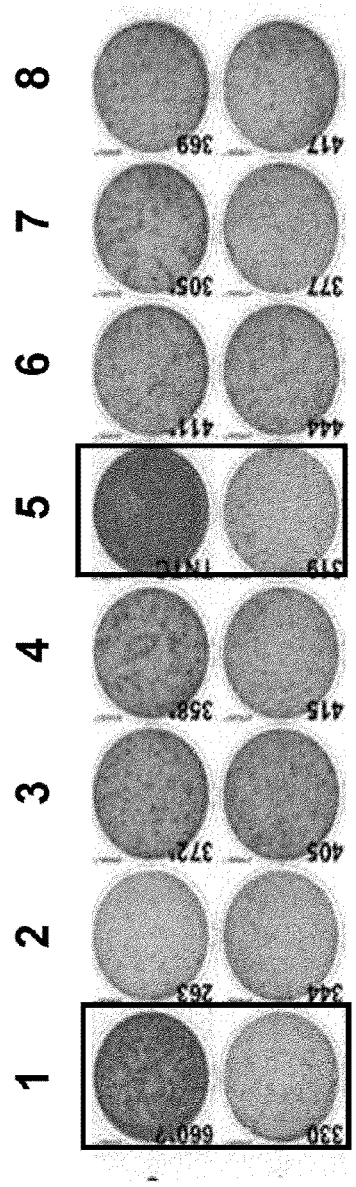
Figure 7B:
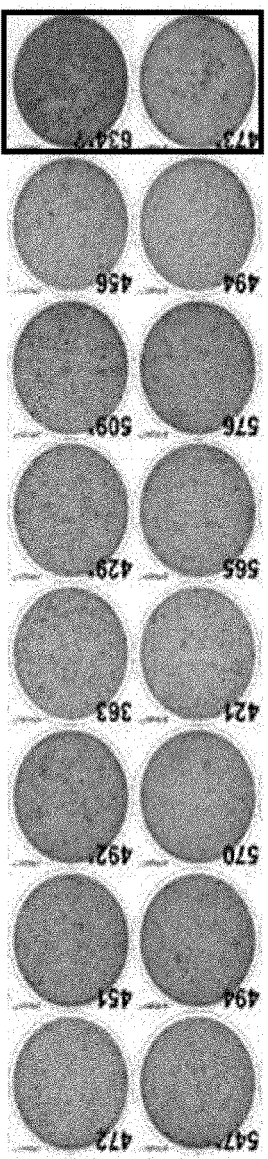
Figure 7C:
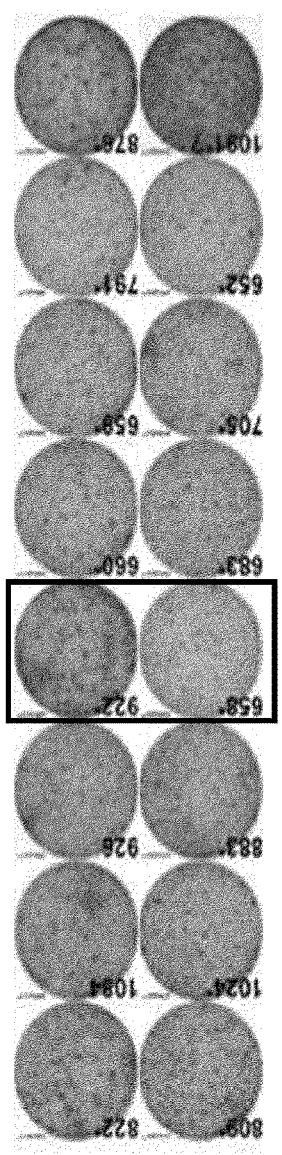

FIG. 7 depicts the results of an IFN-gamma ELISPOT assay for the screening of epitope peptides, which, in turn, demonstrate that MPHOSPH1-A2-9-282 (SEQ ID NO: 9), MPHOSPH1-A2-9-638 (SEQ ID NO: 10) and MPHOSPH1-A2-10-1714 (SEQ ID NO: 11) possess potent IFN-gamma production activity. CTLs for those peptides derived from MPHOSHP1 were generated according to the protocols described in "Materials and Methods" section of the examples set forth below. Resulting CTLs having detectable specific CTL activity are shown. In particular, FIG. 7A demonstrates that the cells in the well number #1 and #5, stimulated with MPHOSPH1-A2-9-282, showed potent IFN-gamma production sufficient to recognize peptide pulsed target cells, as compared to the control. FIG. 7B demonstrates that the cells in the well number #8 stimulated with MPHOSPH1-A2-9-638 showed potent IFN-gamma production sufficient to recognize peptide pulsed target cells, as compared to the control. FIG. 7C demonstrates that the cells in the well number #4 stimulated with MPHOSPH1-A2-10-1714 showed potent IFN-gamma production to recognize peptide pulsed target cells, as compared to the control.

Figure 8A:
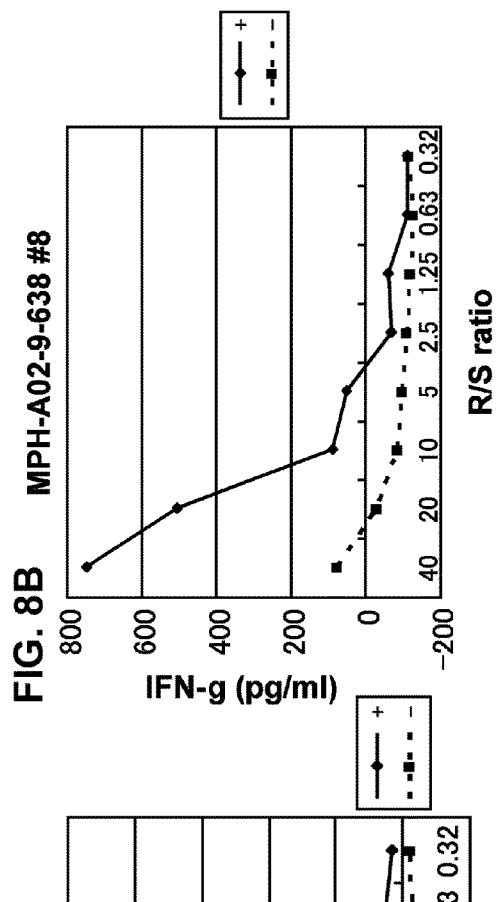
Figure 8B:
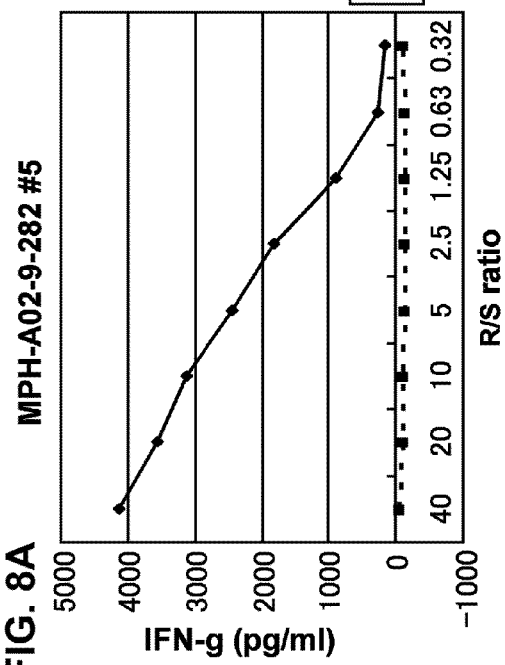
Figure 8C:
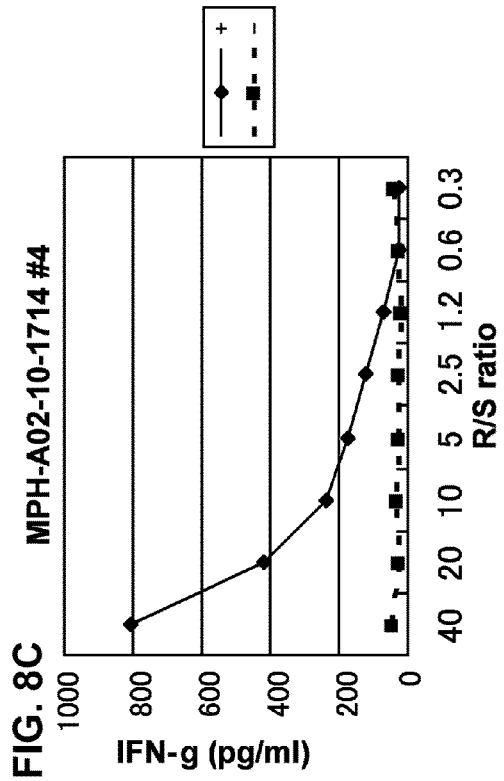

FIG. 8 depicts the establishment for CTL lines stimulated with MPHOSPH1-A02-9-282, (SEQ ID NO: 9) MPHOSPH1-A02-9-638 (SEQ ID NO: 10) and MPHOSPH1-A02-10-1714 (SEQ ID NO: 11). The cells in the positive well were expanded, and, as the depicted results demonstrate, CTL lines having higher specific CTL activities against the MPHOSPH1-A02-9-282-pulsed target (FIG. 8A), MPHOSPH1-A02-9-638-pulsed target (FIG. 8B) or MPHOSPH1-A02-10-1714-pulsed target (FIG. 8C) compared to the activities against target without peptide pulse were established.

R means Responder: CTL lines.
S means Stimulator: peptide-pulsed T2 (1×10$^4$/well).

Figure 9A:
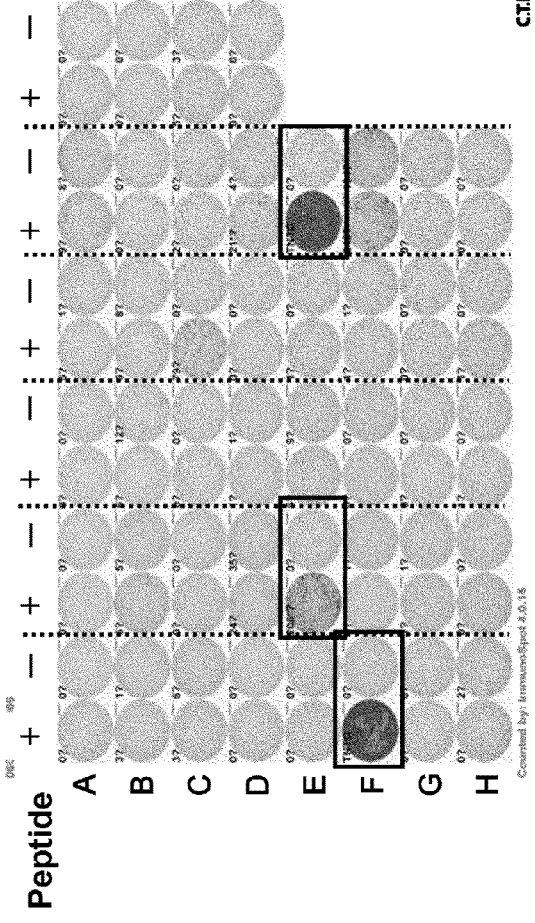
Figure 9B:
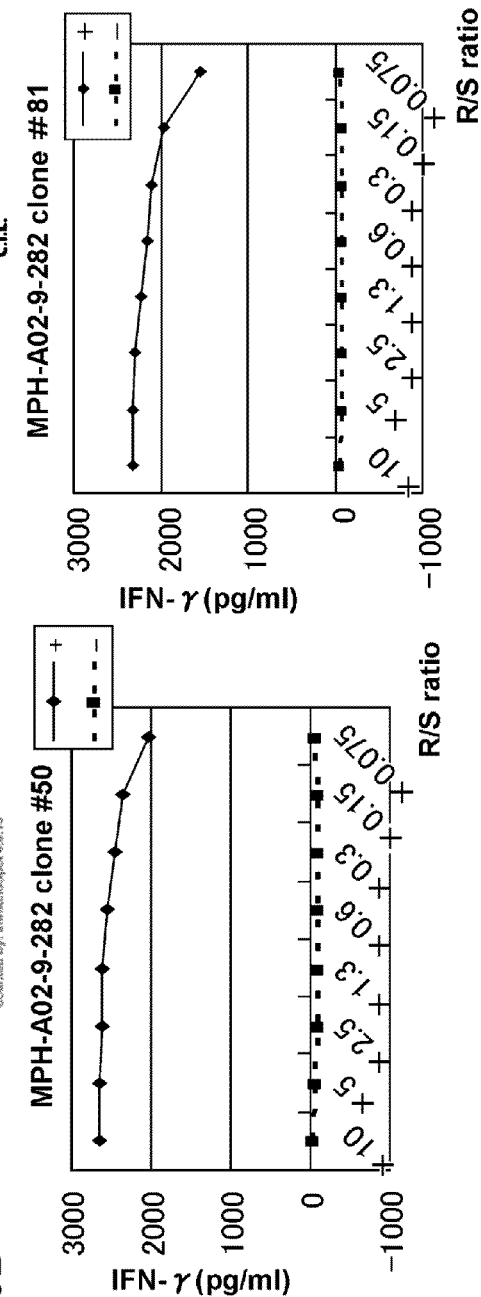

FIG. 9A depicts the results of an IFN-gamma ELISPOT assay for the screening of CTL clones after limiting dilution (MPHOSPH1-A2-9-282 CTL clone). The cells in the positive well were expanded and limiting dilution was performed. As the depicted results demonstrate CTL clones having higher specific CTL activities against the MPHOSPH1-A2-9-282 (SEQ ID NO: 9) pulsed target as compared to the activities against target without peptide pulse were established. FIG. 9B depicts the establishment of CTL clones stimulated with MPHOSPH1-A02-9-282. The CTL clone demonstrated high specific CTL activity against target cells (T2) pulsed with MPHOSPH1-A2-9-282, but did not possess significant CTL activity against the same target cells (T2) pulsed with no peptides.

R means Responder: CTL clone.
S means Stimulator: peptide-pulsed T2 (1×10$^4$/well).

FIG. 10A depicts the results of an IFN-gamma ELISPOT assay for the screening of epitope peptides, which, in turn, demonstrate that DEPDC1-A24-9-294 (SEQ ID NO: 12) is a potent producer of IFN-gamma. CTLs for those peptides derived from DEPDC1 were generated according to the protocols described in "Materials and Methods" section of the examples set forth below. Resulting CTLs showing detectable specific CTL activity are shown. The cells in the well number #10 stimulated with DEPDC1-A24-9-294 showed potent IFN-gamma production to recognize peptide pulsed target cells, compared with the control. FIG. 10B depicts the results of an IFN-gamma ELISPOT assay for the screening of CTL clones after limiting dilution (DEPDC1-A24-9-294 CTL clone). The cells in the positive well were expanded and limiting dilution performed. As the depicted results demonstrate, CTL clones having higher specific CTL activities against the DEPDC1-A24-9-294-pulsed target compared to the activities against target without peptide pulse were established.

Figure 11:
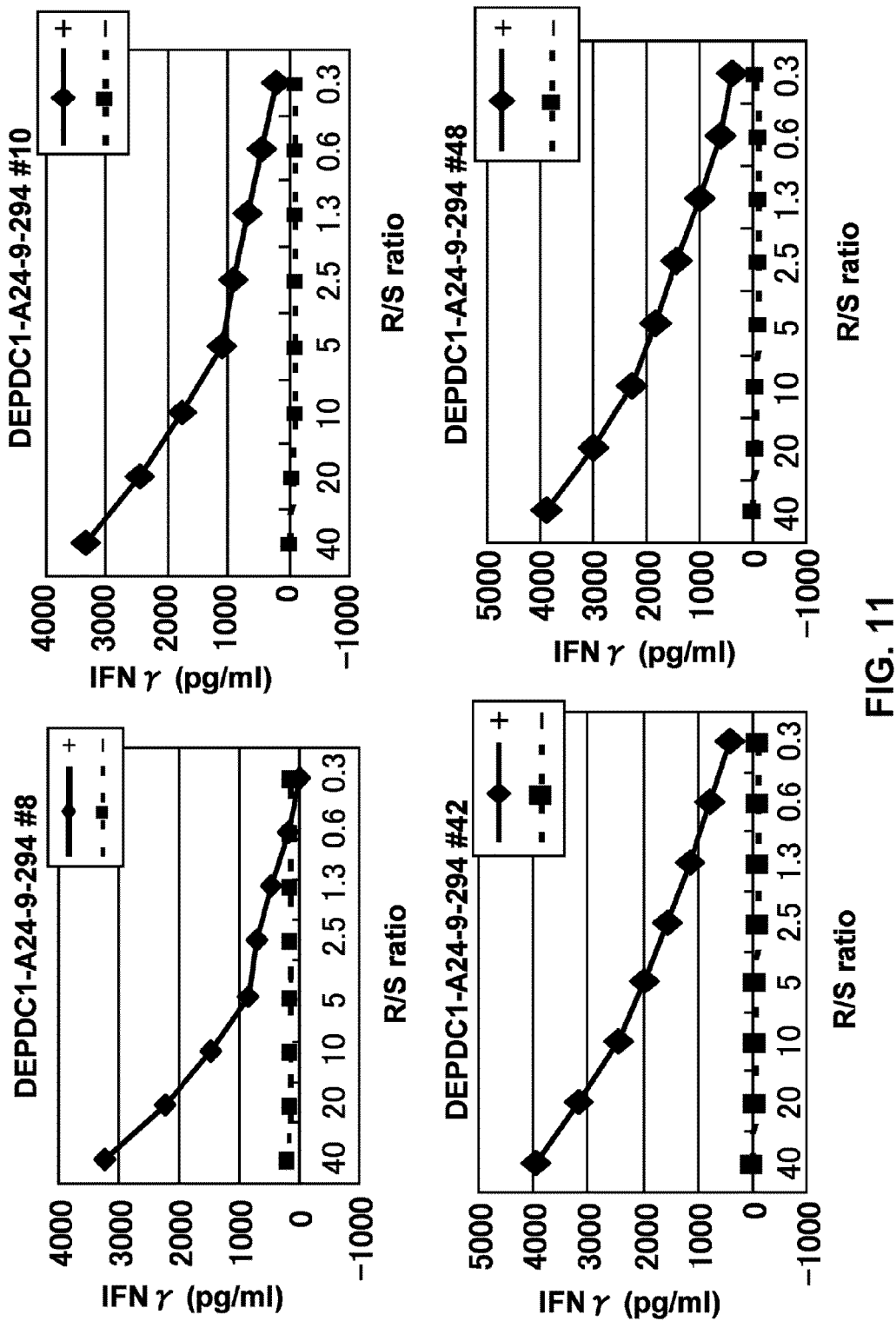

FIG. 11 depicts the establishment for CTL clones stimulated with DEPDC1-A24-9-294 (SEQ ID NO: 12). The CTL clone showed high specific CTL activity against target cells (A24LCL) pulsed with DEPDC1-A24-9-294, whereas it did not show significant CTL activity against the same target cells (A24LCL) pulsed with no peptides.

R means Responder: DEPDC-A24-9-294 CTL clone.
S means Stimulator: peptide-pulsed A24-LCL (1×10$^4$/well).

Figure 12:
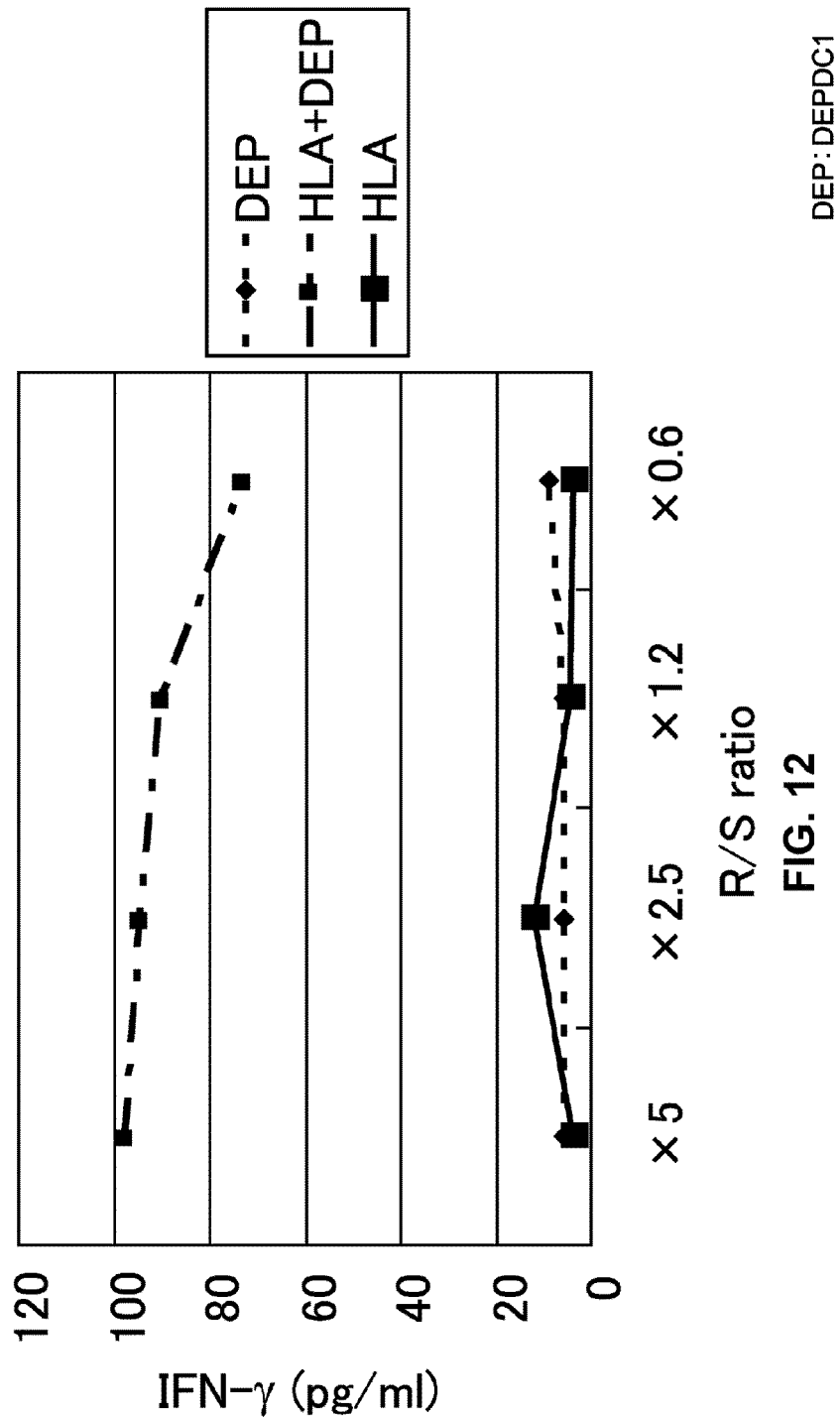

FIG. 12 depicts the expression of DEPDC1-A24-9-294 (SEQ ID NO: 12) on the target cell surface with HLA-A24. Specific CTL activity against COS7 transfected with both the full length DEPDC1 gene and the HLA-A*2402 molecule was assayed using as effector cells the CTL clone raised by DEPDC1-A24-9-294. COS7 transfected with full length DEPDC1 but not HLA-A*2402 and COS7 transfected HLA-A*2402 but not full length DEPDC1 were prepared as controls. The CTL clone established demonstrated high specific CTL activity against COS7 transfected with both DEPDC1 and HLA-A24. However, it did not show significant specific CTL activity against COS7 transfected with neither DEPDC1 nor HLA-A24.

R means Responder: DEP-A24-9-294 CTL clone.
S means Stimulator: COS7 transfectant (1×10$^4$/well).

Figure 13:
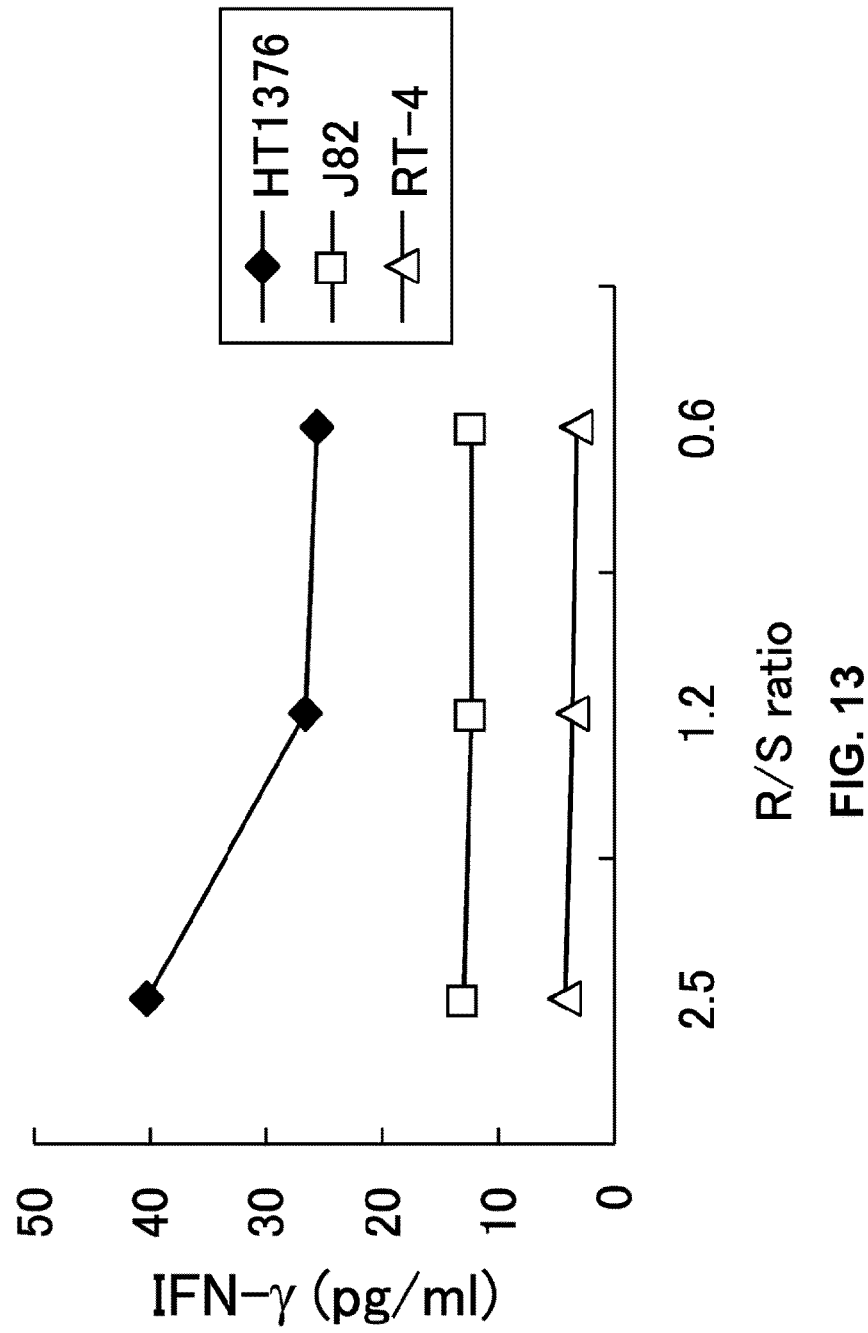

FIG. 13 depicts the CTL activity against bladder cancer cell lines endogenously expressing DEPDC1. The established CTL clone induced with DEPDC1-A24-9-294 peptide recognized tumor cells endogenously expressing DEPDC1. HT1376, RT-4 and J82 cells expressed DEPDC1 endogenously, respectively. CTL clone showed IFN-gamma production against HT1376 which have HLA-A*2402 genotype, but no showing response against RT-4 and J82, does not have HLA-A*2402 genotype.

Figure 14:
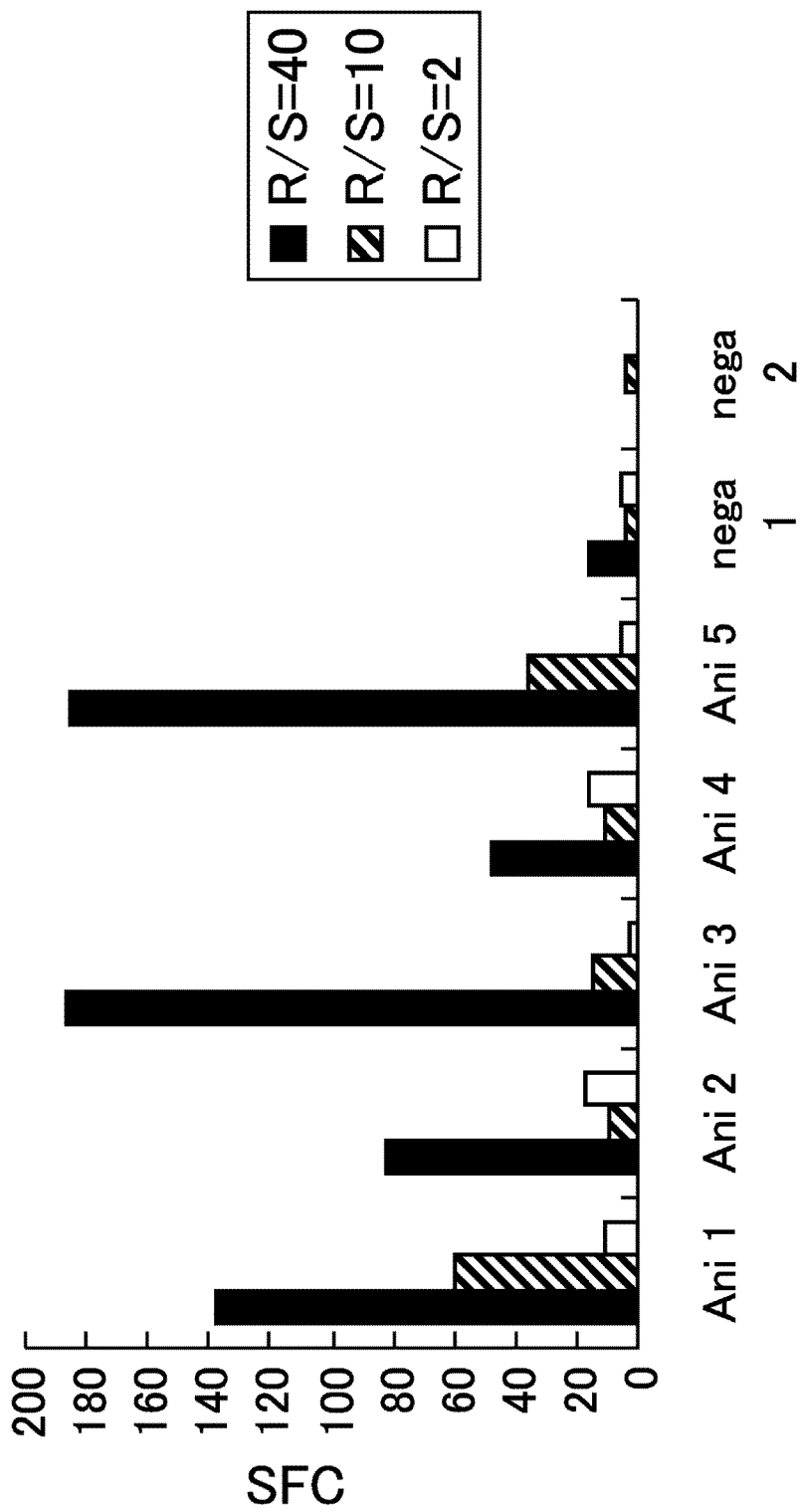

FIG. 14 depicts the in vivo immunogenicity analysis using DEPDC1-A24-9-294 peptide. IFA-conjugated peptide was injected subcutaneously into BALB/c mice on days 0 and 7. On day 14, splenocytes of vaccinated mice were harvested and used as responder cells, and 1×10$^4$ RLmale1 cells pulsed DEPDC1-A24-9-294 peptide were used as stimulator cells for IFN-gamma ELISPOT assay. Spot forming counts (SFC)

were indicated in cases of each mice; five mice (Ani1~Ani5) were vaccinated epitope peptide and two mice (nega1 and nega2) were injected Mock IFA emulsion as a negative control.

Figure 15:
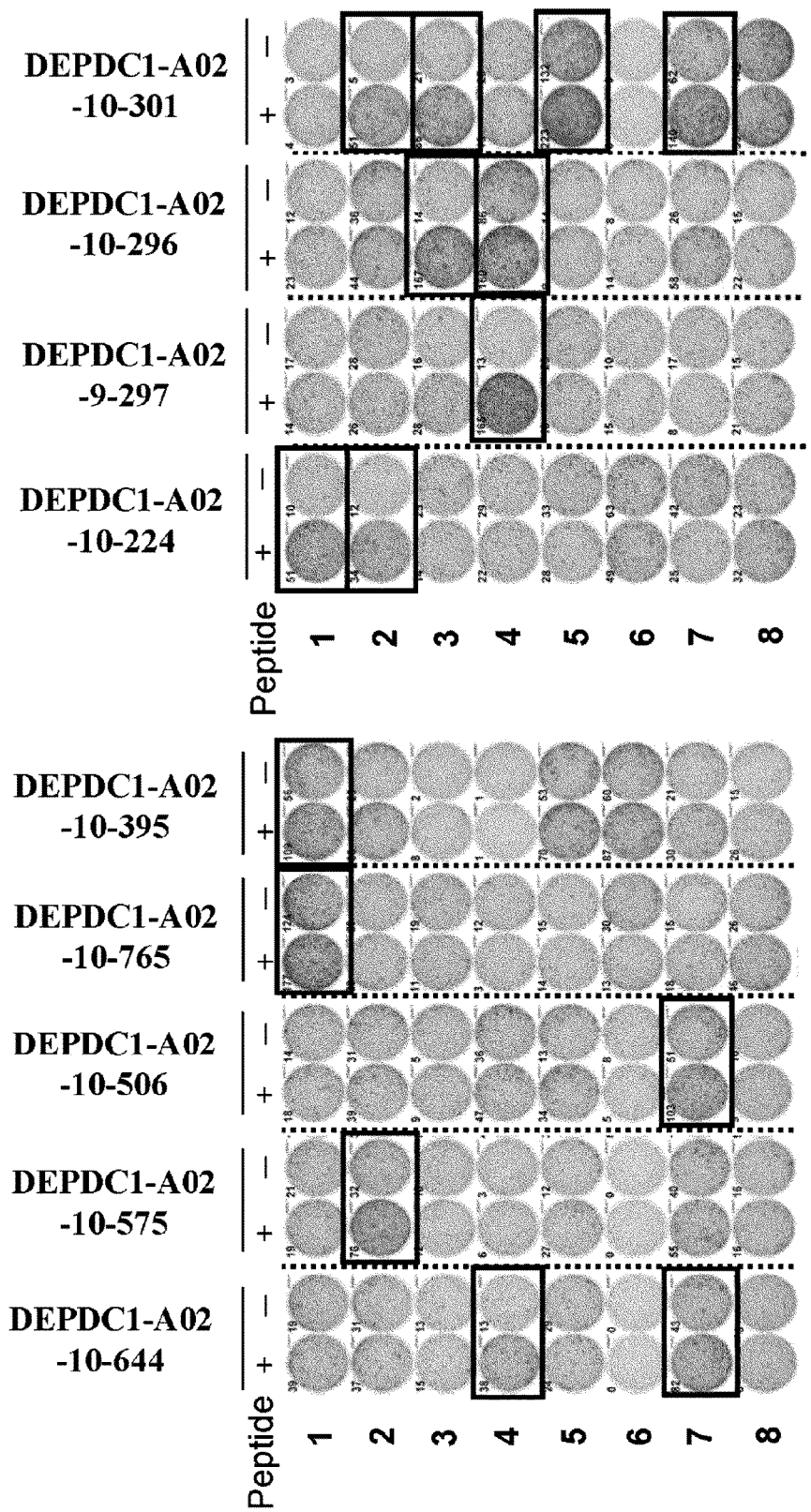

FIG. 15 depicts potent IFN-gamma production of DEPDC1-A02-10-644, -10-575, -10-506, -10-765, -10-395, -10-224, -9-297, -10-296 and -10-302 by IFN-gamma ELISPOT assay for the screening of epitope peptides. CTLs for those peptides derived from DEPDC1 were generated in the way described in "Materials and Methods". The cells in the well number #4 and #7 stimulated with DEPDC1-A02-10-644, #2 with DEPDC1-A02-10-575, #7 with DEPDC1-A02-10-506, #1 with DEPDC1-A02-10-765 and #1 with DEPDC1-A02-10-395, #1 and #2 with DEPDC1-A02-10-224, #4 with DEPDC1-A02-9-297, #3 and #4 with DEPDC1-A02-10-296 and #2, #3, #5 and #7 with DEPDC1-A02-10-302 showed potent IFN-gamma production compared with the control.

Figure 16:
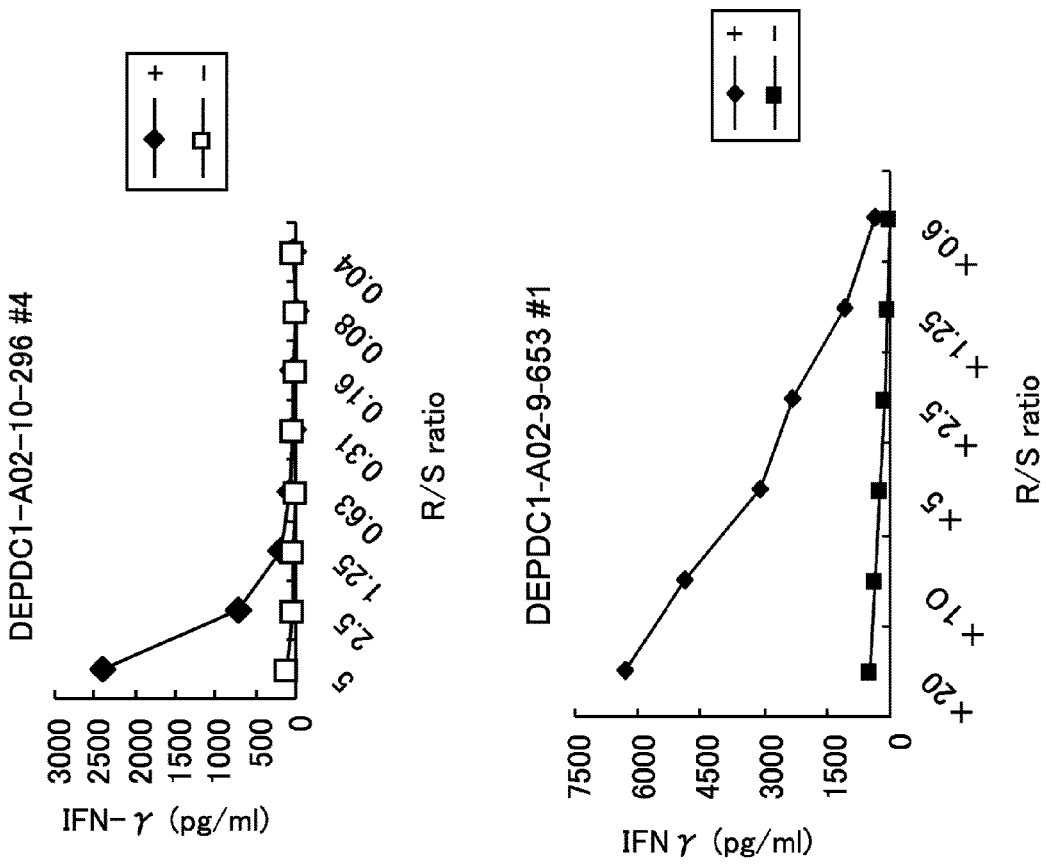

FIG. 16 depicts IFN-gamma production of CTL line generated with DEPDC1-A02-10-296 peptide. The established CTL lines raised by DEPDC1-A02-10-296 peptide have potent IFN-gamma production activity. It was shown IFN-gamma production against peptide-pulsed target cells, but not shown that against target cells without peptide pulse. Target cells were used T2 cells, expressed HLA-A2 molecule at cell surface.

Figure 17:
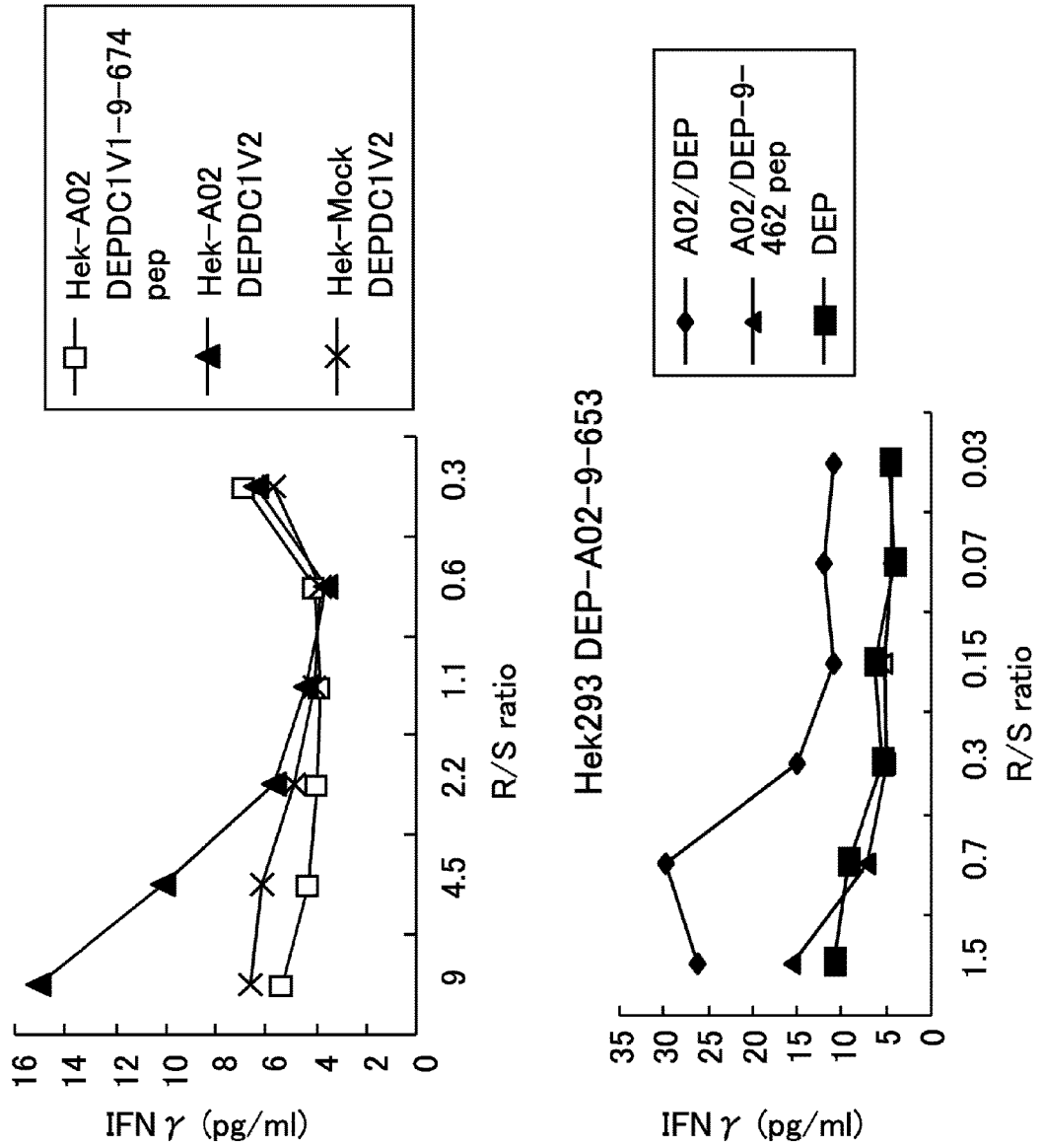

FIG. 17 depicts CTL activity against targets endogenously expressing DEPDC1 and HLA-A2 molecule. It was shown in upper panel that the established CTL line generated with DEPDC1-A02-10-296 peptide possessed IFN-gamma production activity against target cells which endogenously expressed DEPDC1V2 and HLA-A2. The case of using DEPDC1-A02-10-296 peptide was shown in lower panel. The target cells expressing only DEPDC1V2 and expressing only HLA-A2 with treatment of DEPDC1V1-9-674 or DEP-9-462 peptide pulse were prepared as the negative control. The target cells were prepared from HEK293 transfectant which stable expressed HLA-A2 or mock.

Figure 18:
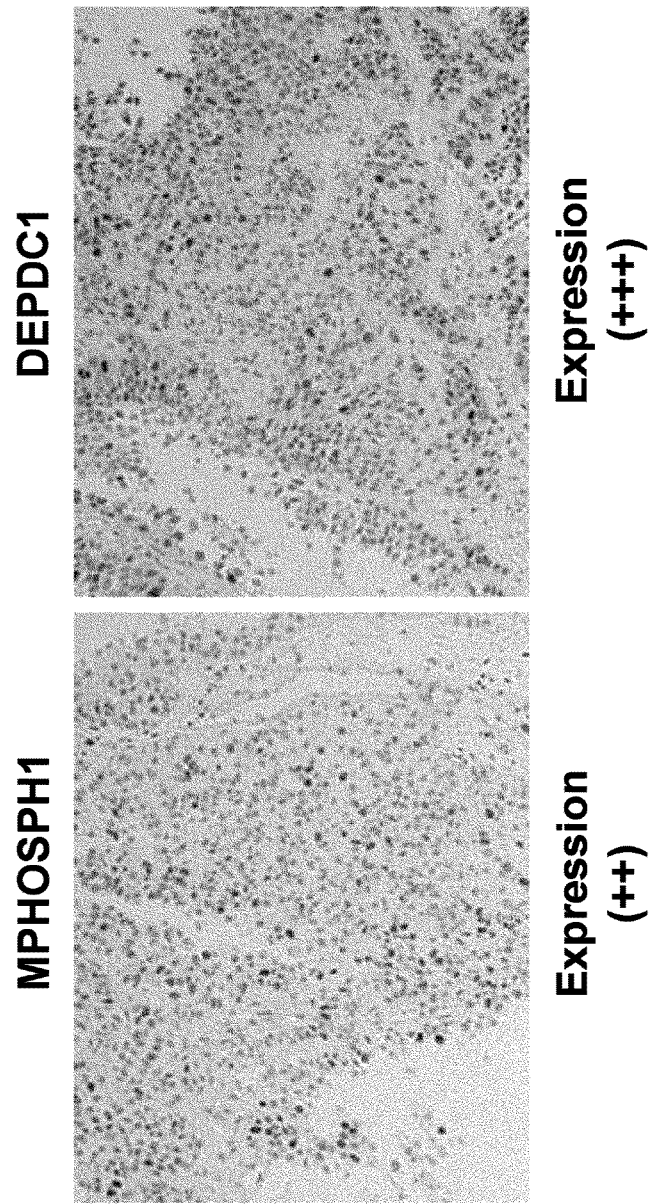

FIG. 18 depicts antigen expression in Case 2. In Case 2, both MPHOSPH1 and DEPDC1 were expressed strongly. Therefore, two kinds of epitope peptides derived from MPHOSPH1 and DEPDC1 have been vaccinated.

FIG. 19 depicts the clinical evaluation for local recurrence of bladder cancer in Case 2. Case 2 were evaluated SD in accordance with RECIST criteria.

Figure 20:
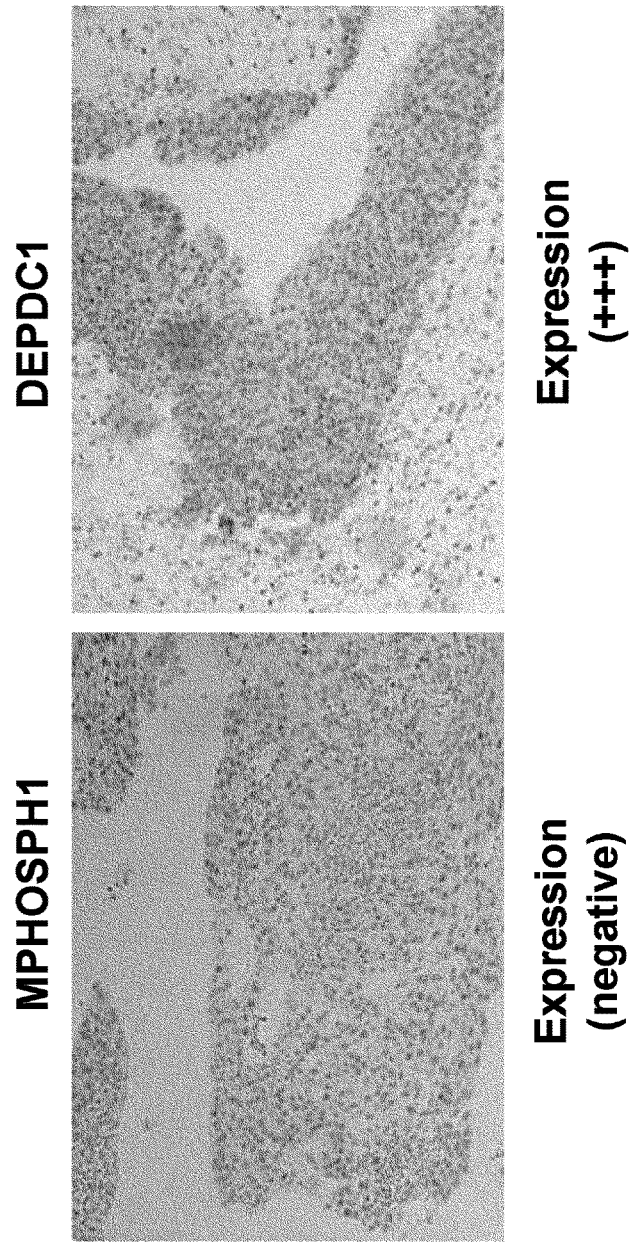

FIG. 20 depicts antigen expression in Case 3. In Case 3, DEPDC1 was expressed strongly. Therefore, we have vaccinated the epitope peptide derived from DEPDC1 alone.

FIG. 21 depicts clinical evaluation for right lobe of metastatic lung in Case 3. The progression rate was decreased after vaccination. Especially, the size of the tumor was decreased after 3rd courses.

Figure 22:
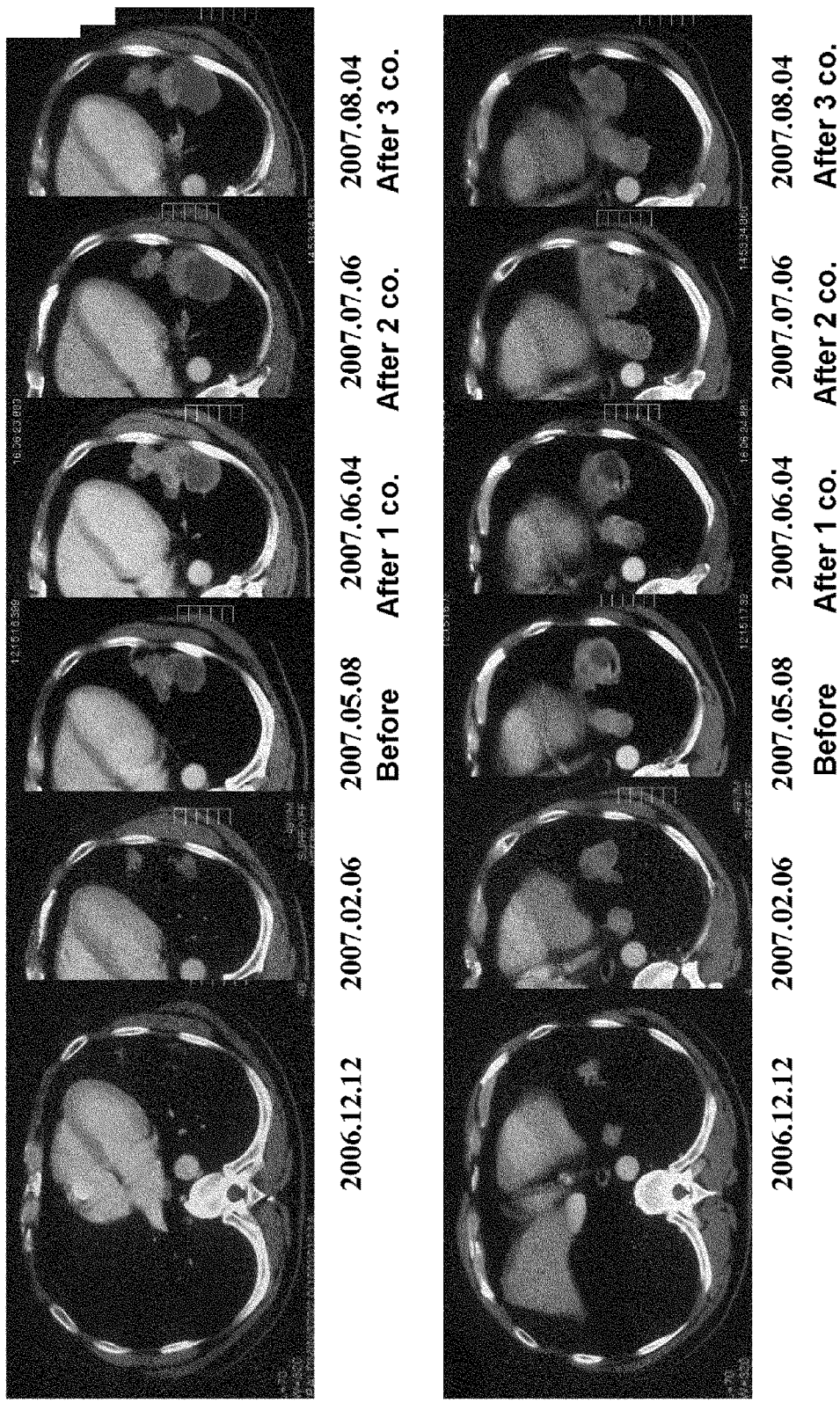

FIG. 22 depicts clinical evaluation for left lobe of metastatic lung in Case 3. The progression rate was decreased after vaccination. Especially, the size of the tumor was decreased after 3rd courses.

Figure 23:
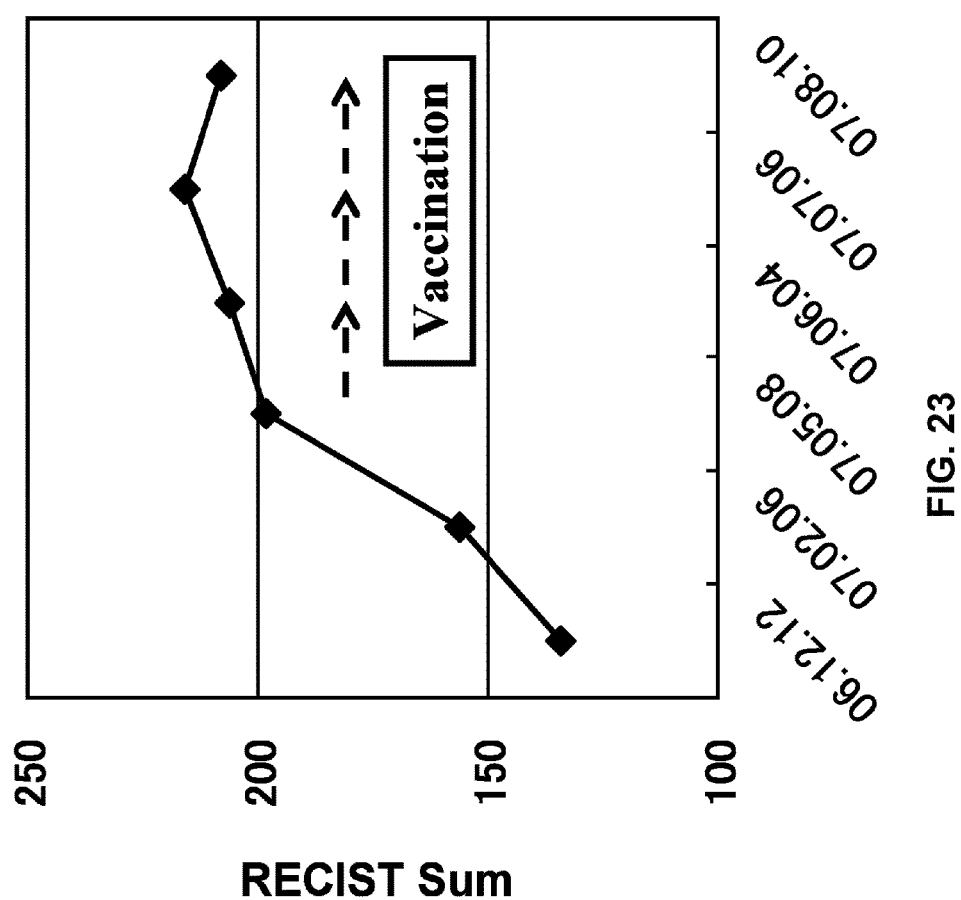

FIG. 23 depicts the Anti-tumor effect in Case 3. The progression rate of metastatic tumor was decreased after vaccination.

Figure 24:
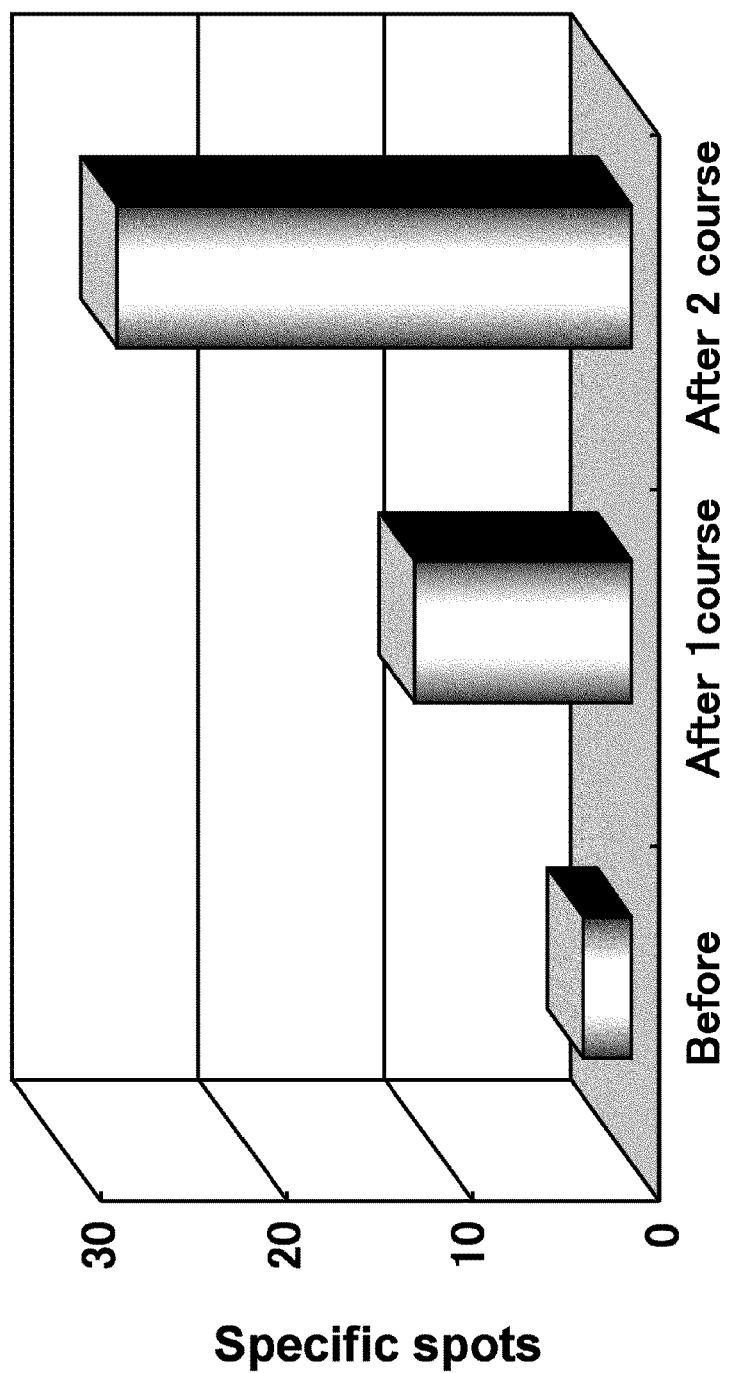

FIG. 24 depicts specific CTL response in Case 3. Specific CTL response was strongly shown after vaccination.

Figure 25:
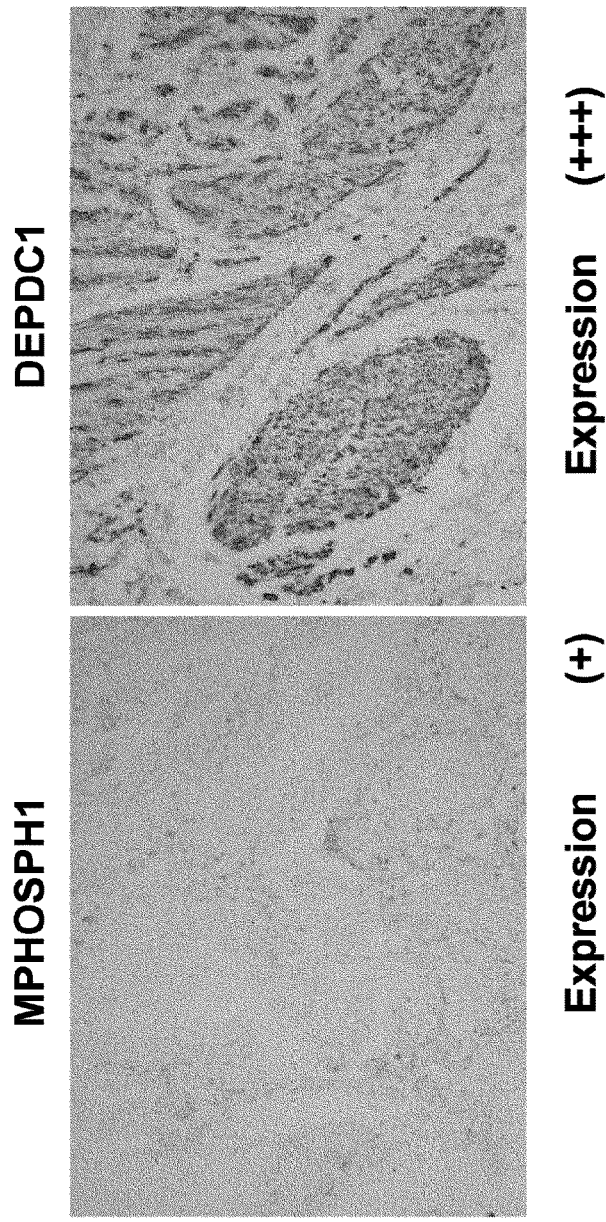

FIG. 25 depicts antigen expression in Case 4. In Case 4, MPHOSPH1 and DEPDC1 were expressed. Therefore, two kinds of epitope peptides derived from MPHOSPH1 and DEPDC1 have been vaccinated.

Figure 26:
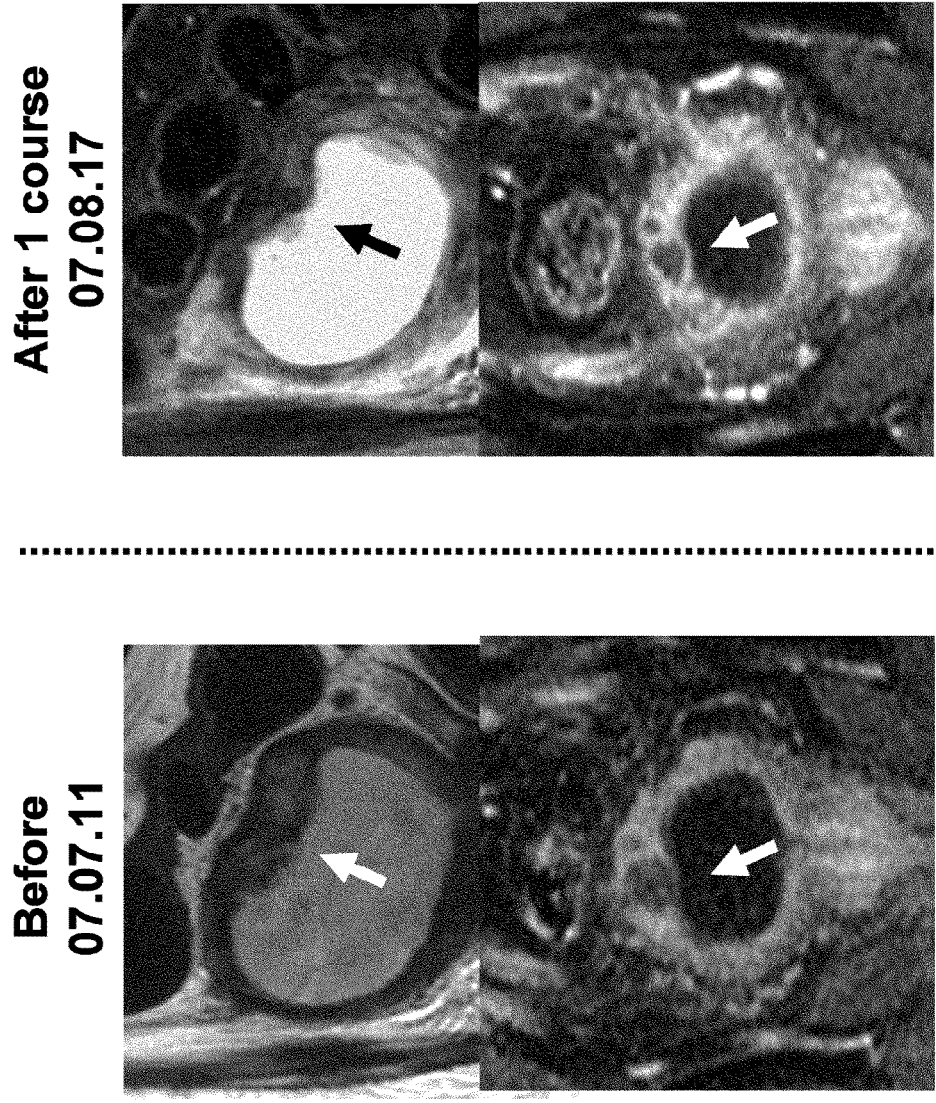

FIG. 26 depicts the clinical evaluation for local recurrence of bladder cancer in Case 4. The size of the tumor was reduced 20% in accordance with RECIST criteria after 1st course vaccination.

DETAILED DESCRIPTION OF THE INVENTION

The words "a", "an", and "the" as used herein mean "at least one" unless otherwise specifically indicated.

Unless otherwise defined, all technical and scientific terms used herein have the same meaning as commonly understood by one of ordinary skill in the art to which this invention belongs.

Identification of new TAAs, particularly those that induce potent and specific anti-tumor immune responses, warrants further development of the clinical application of the peptide vaccination strategy in various types of cancer (Boon T et al., (1996) J Exp Med 183: 725-9; van der Bruggen P et al., (1991) Science 254: 1643-7; Brichard V et al., (1993) J Exp Med 178: 489-95; Kawakami Y et al., (1994) J Exp Med 180: 347-52; Shichijo S et al., (1998) J Exp Med 187:277-88; Chen Y T et al., (1997) Proc. Natl. Acd. Sci. USA, 94: 1914-8; Harris C C, (1996) J Natl Cancer Inst 88:1442-55; Butterfield L H et al., (1999) Cancer Res 59:3134-42; Vissers J L et al., (1999) Cancer Res 59: 5554-9; van der Burg S H et al., (1996) J. Immunol. 156:3308-14; Tanaka F et al., (1997) Cancer Res 57:4465-8; Fujie T et al., (1999) Int J Cancer 80:169-72; Kikuchi M et al., (1999) Int J Cancer 81: 459-66; Oiso M et al., (1999) Int J Cancer 81:387-94). As noted above, MPHOSPH1 (M-phase phosphoprotein 1; GenBank Accession No. NM_016195; SEQ ID Nos.1, 2) and DEPDC1 (DEP domain containing 1; GenBank Accession No. BM683578), more particularly its two variants, DEPDC1V1 (SEQ ID Nos.3, 4) and DEPDC1V2 (SEQ ID No. 5, 6), were previously identified using cDNA microarray technologies as over-expressed in various cancers. MPHOSPH1 was previously identified as one of the proteins specifically phosphorylated at the G2/M transition, and characterized as a plus-end-directed kinesin related protein (Abaza A et al., J Biol Chem 2003, 278: 27844-52). More particularly, MPHOSPH1 was previously documented to be plus-end-directed molecular motor that plays a crucial role in cytokinesis, and accumulates in the midzone of the spindle during anaphase to telophase in HeLa cells (Abaza A et al., J Biol Chem 2003, 278: 27844-52; Kamimoto T et al., J Biol Chem 2001, 276: 37520-8). The MPHOSPH1 cDNA encodes a 1780-amino acid protein that is composed of three domains: an NH2-kinasin motor domain, a central coiled coil-stalk domain, and a C-globular tail domain. These data suggest that MPHOSPH1 is an NH2-type kinesin-related protein.

The function of DEPDC1 protein remains unclear. The DEP domain included this protein is found in Dishevelled, Egl-10, and Pleckstrin. In particular, the DEP domain in *Drosophila* dishevelled is essential to rescue planar polarity defects and induces JNK signaling; nevertheless, its function in Human has not yet been clarified. However, as disclosed in PCT/JP2006/302684, DEPDC1 (in house No. B5860N) has two different transcriptional variants consisting of 12 and 11 exons, corresponding to DEPDC1 V1 and V2, respectively. Alternative variations in exon 8 of V1 were noted, and the other remaining exons were found to be common to both variants. V2 variant has no exon 8 of the V1, but generates the same stop codon within last exon. The full-length cDNA sequences of the B5860NV1 and B5860NV2 variants consist of 5318 and 4466 nucleotides, respectively. The ORF of these variants start at within each exon 1. Eventually, V1 and V2 transcripts encode 811 and 527 amino acids, respectively.

siRNAs suppressed the growth of cancer cells. These results demonstrate that DEPDC1 plays important roles in growth of most cancer cells.

As disclosed in PCT/JP2006/302684, MPHOSPH1 and DEPDC1 are over-expressed in bladder cancer but show minimal expression in normal tissues. In addition, these genes were found to have a significant function related to cell proliferation.

In the present invention, peptides derived from MPHOSPH1 or DEPDC1 are shown to be TAA epitopes restricted by HLA-A24 and HLA-A2, an HLA allele commonly found in the Japanese and Caucasian populations. Specifically, using their binding affinities to HLA-A24 and HLA-A2, candidates of HLA-A24 and HLA-A2 binding peptides derived from MPHOSPH1 or DEPDC1 were identified. After the in vitro stimulation of T-cells by dendritic cells (DCs) loaded with these peptides, CTLs were successfully established using MPHOSPH1-A24-9-278 (IYNEYIYDL (SEQ ID NO: 7)), MPHOSPH1-A24-10-278 (IYNEyIYDLF (SEQ ID NO: 8)), MPHOSPH1-A2-9-282 (YIYDLFVPV (SEQ ID NO: 9)), MPHOSPH1-A2-9-638 (RLAIFKDLV (SEQ ID NO: 10)), MPHOSPH1-A2-10-1714 (TMSSsKL-SNV (SEQ ID NO: 11)), DEPDC1-A24-9-294 (EYYELFVNI (SEQ ID NO: 12)), DEPDC1-A02-10-644 (SLMIhTFSRC (SEQ ID NO: 240)), DEPDC1-A02-10-575 (SLLPaSSMLT (SEQ ID NO: 241)), DEPDC1-A02-10-506 (QLCRsQSLLL (SEQ ID NO: 243)), DEPDC1-A02-10-765 (KQFQkEYPLI (SEQ ID NO: 244)), DEPDC1-A02-10-395 (IMGGSCHNLI (SEQ ID NO: 249), DEPDC1-A02-10-224 (NMANtSKRGV (SEQ ID NO: 253)), DEPDC1-A02-9-297 (ELFVNILGL (SEQ ID NO: 226)), DEPDC1-A02-10-296 (YELFvNILGL (SEQ ID NO: 254)), DEPDC1-A02-10-301 (NILGILQPHL (SEQ ID NO: 255)), DEPDC1-A2-9-589 (LLQPHLERV (SEQ ID NO: 192)), DEPDC1-A2-9-619 (LLMRMISRM (SEQ ID NO: 195)), DEPDC1-A2-9-290 (LLTFEYYEL (SEQ ID NO: 197)), DEPDC1-A2-9-563 (RLCKSTIEL (SEQ ID NO: 209)), DEPDC1-A2-9-653 (CV-LCCAEEV (SEQ ID NO: 225)), DEPDC1-A2-10-674 (FLMDhHQEIL (SEQ ID NO: 228)) and DEPDC1-A2-10-302 (ILVVcGYITV (SEQ ID NO: 230)). These CTLs demonstrated potent cytotoxic activity against the peptide-pulsed A24LCL and T2 cells. Furthermore, CTL clones derived from these cells also demonstrated specific cytotoxicity against HLA-A24 or HLA-A2 positive cells expressing MPHOSPH1 or DEPDC1, respectively. However, these CTL clones did not express cytotoxic activity against cells having expression of only one of peptides, including HLA-A24, HLA-A2, MPHOSPH1 and DEPDC1. Together these results suggest the utility of MPHOSPH1 and DEPDC1 as TAAs for cancer cells and that MPHOSPH1-A24-9-278 (IYNEYIYDL (SEQ ID NO: 7)), MPHOSPH1-A24-10-278 (IYNEyIYDLF (SEQ ID NO: 8)), MPHOSPH1-A2-9-282 (YIYDLFVPV (SEQ ID NO: 9)), MPHOSPH1-A2-9-638 (RLAIFKDLV (SEQ ID NO: 10)), MPHOSPH1-A2-10-1714 (TMSSsKL-SNV (SEQ ID NO: 11)), DEPDC1-A24-9-294 (EYYELFVNI (SEQ ID NO: 12)), DEPDC1-A02-10-644 (SLMIhTFSRC (SEQ ID NO: 240)), DEPDC1-A02-10-575 (SLLPaSSMLT (SEQ ID NO: 241)), DEPDC1-A02-10-506 (QLCRsQSLLL (SEQ ID NO: 243)), DEPDC1-A02-10-765 (KQFQkEYPLI (SEQ ID NO: 244)), DEPDC1-A02-10-395 (IMGGSCHNLI (SEQ ID NO: 249), DEPDC1-A02-10-224 (NMANtSKRGV (SEQ ID NO: 253)), DEPDC1-A02-9-297 (ELFVNILGL (SEQ ID NO: 226)), DEPDC1-A02-10-296 (YELFvNILGL (SEQ ID NO: 254)), DEPDC1-A02-10-301 (NILGILQPHL (SEQ ID NO: 255)), DEPDC1-A2-9-589 (LLQPHLERV (SEQ ID NO: 192)), DEPDC1-A2-9-619 (LLMRMISRM (SEQ ID NO: 195)), DEPDC1-A2-9-290 (LLTFEYYEL (SEQ ID NO: 197)), DEPDC1-A2-9-563 (RLCKSTIEL (SEQ ID NO: 209)), DEPDC1-A2-9-653 (CV-LCCAEEV (SEQ ID NO: 225)), DEPDC1-A2-10-674 (FLMDhHQEIL (SEQ ID NO: 228)) and DEPDC1-A2-10-302 (ILVVcGYITV (SEQ ID NO: 230)) are epitope peptides of each TAA restricted by HLA-A24 or HLA-A2. Since these antigens are over-expressed in most cancers and are associated with tumor cell proliferation, they find utility as immunotherapeutic targets against cancers. Exemplary cancers include, but are not limited to, bladder cancer, breast cancer, cervical cancer, cholangincellular carcinoma, CML, colorectal cancer, gastric cancer, NSCLC, lymphoma, osteosarcoma, prostate cancer, renal carcinoma, SCLC, soft tissue tumor.

Accordingly, the present invention further provides methods of treating or preventing a disease associated with the over-expression of MPHOSPH1 and/or DEPDC1, e.g. cancers, in a subject, such methods including the steps of administering to a subject in need thereof an immunogenic peptide of less than about 40 amino acids, often less than about 20 amino acids, usually less than about 15 amino acids and having the amino acid sequence of SEQ ID NOs: 7, 8, 9, 10, 11, 12, 192, 195, 197, 209, 225, 226, 228, 230, 240, 241, 243, 244, 249, 253, 254 or 255. Alternatively, the immunogenic peptide may be composed of a sequence of SEQ ID NOs: 7, 8, 9, 10, 11, 12, 192, 195, 197, 209, 225, 226, 228, 230, 240, 241, 243, 244, 249, 253, 254 or 255 in which 1, 2, or several (e.g., up to 5) amino acids are substituted, deleted or added, provided the resulting variant peptide retains the immunogenic activity (i.e., the ability to induce CTLs specific to cells expressing MPHOSPH1 and/or DEPDC1, e.g. cancers). The number of residues to be substituted, deleted, or added is generally 5 amino acids or less, preferably 4 amino acids or less, more preferably 3 amino acids or less, even more preferably one or two amino acids. The cancers contemplated include, but are not limited to, bladder cancer, breast cancer, cervical cancer, cholangincellular carcinoma, CML, colorectal cancer, gastric cancer, NSCLC, lymphoma, osteosarcoma, prostate cancer, renal carcinoma, SCLC, soft tissue tumor.

Variant peptides (i.e., peptides having an amino acid sequence modified by substituting, deleting, or adding one, two or several amino acid residues to an original amino acid sequence) are known to retain the original biological activity (Mark D F et al., (1984) Proc Natl Acad Sci USA 81: 5662-6; Zoller M J and Smith M, (1982) Nucleic Acids Res 10:6487-500; Dalbadie-McFarland G et al., (1982) Proc Natl Acad Sci USA 79: 6409-13). In the context of the present invention, it is preferable that the amino acid modification results in conservation of the properties of the original amino acid side-chain (a process known as conservative amino acid substitution). Examples of properties of amino acid side chains include hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

In preferred embodiments, the immunogenic peptide is a nonapeptide (9-mer) or a decapeptide (10-mer).

The present invention further provides a method of inducing anti-tumor immunity for a disease associated with the over-expression of MPHOSPH1 and/or DEPDC1, e.g. cancers, in a subject, such a method including the steps of administering to a subject in need thereof an immunogenic peptide of the present invention, namely one having the amino acid sequence of S SEQ ID NOs: 7, 8, 9, 10, 11, 12, 192, 195, 197, 209, 225, 226, 228, 230, 240, 241, 243, 244, 249, 253, 254 or 255 or a variant thereof (i.e., including 1, 2, or several amino acid substitutions, deletions, or additions). The cancers contemplated include, but are not limited to, bladder cancer, breast cancer, cervical cancer, cholangincellular carcinoma, CML, colorectal cancer, gastric cancer, NSCLC, lymphoma, osteosarcoma, prostate cancer, renal carcinoma, SCLC, soft tissue tumor.

In the context of the present invention, the subject is preferably a mammal. Exemplary mammals include, but are not limited to, e.g., a human, non-human primate, mouse, rat, dog, cat, horse, or cow.

In the present invention, the peptide can be administered to a subject via an in vivo or ex vivo protocol. Furthermore, the present invention also provides use of nonapeptide or decapeptide selected from peptides having the amino acid sequence of SEQ ID NOs: 7, 8, 9, 10, 11, 12, 192, 195, 197, 209, 225, 226, 228, 230, 240, 241, 243, 244, 249, 253, 254 and 255 (and variants thereof) for manufacturing an immunogenic composition for treating or preventing a disease associated with the over-expression of MPHOSPH1 and/or DEPDC1, e.g. cancers. The cancers contemplated include, but are not limited to, bladder cancer, breast cancer, cervical cancer, cholangincellular carcinoma, CML, colorectal cancer, gastric cancer, NSCLC, lymphoma, osteosarcoma, prostate cancer, renal carcinoma, SCLC, soft tissue tumor.

Homology analyses of MPHOSPH1-A24-9-278 (IYNEY-IYDL (SEQ ID NO: 7)), MPHOSPH1-A24-10-278 (IYNEy-IYDLF (SEQ ID NO: 8)), MPHOSPH1-A2-9-282 (YIY-DLFVPV (SEQ ID NO: 9)), MPHOSPH1-A2-9-638 (RLAIFKDLV (SEQ ID NO: 10)), MPHOSPH1-A2-10-1714 (TMSSsKLSNV (SEQ ID NO: 11)), DEPDC1-A24-9-294 (EYYELFVNI (SEQ ID NO: 12)), DEPDC1-A2-9-589 (LLQPHLERV (SEQ ID NO: 192)), DEPDC1-A2-9-619 (LLMRMISRM (SEQ ID NO: 195)), DEPDC1-A2-9-290 (LLTFEYYEL (SEQ ID NO: 197)), DEPDC1-A2-9-563 (RLCKSTIEL (SEQ ID NO: 209)), DEPDC1-A2-9-653 (CV-LCCAEEV (SEQ ID NO: 225)), DEPDC1-A2-10-674 (FLMDhHQEIL (SEQ ID NO: 228)), DEPDC1-A2-10-302 (ILVVcGYITV (SEQ ID NO: 230)) DEPDC1-A02-10-644 (SLMIhTFSRC (SEQ ID NO: 240)), DEPDC1-A02-10-575 (SLLPaSSMLT (SEQ ID NO: 241)), DEPDC1-A02-10-506 (QLCRsQSLLL (SEQ ID NO: 243)), DEPDC1-A02-10-765 (KQFQkEYPLI (SEQ ID NO: 244)), DEPDC1-A02-10-395 (IMGGSCHNLI (SEQ ID NO: 249)), DEPDC1-A02-10-224 (NMANtSKRGV (SEQ ID NO: 253)), DEPDC1-A02-9-297 (ELFVNILGL (SEQ ID NO: 226)), DEPDC1-A02-10-296 (YELFvNILGL (SEQ ID NO: 254)) and DEPDC1-A02-10-301 (NILGILQPHL (SEQ ID NO: 255)) demonstrate that they do not have significant homology with the peptides derived from any known human gene products. Accordingly, the possibility of unknown or undesirable immune responses with immunotherapy against these molecules is significantly reduced.

Regarding HLA antigens, the data presented here demonstrate that the uses of A-24 type or A-2 type antigens (which are said to be highly expressed among the Japanese) are favorable for obtaining effective results. The uses of subtypes such as A-2402 and A-0201 are even more preferable. Typically, in the clinic, the type of HLA antigen of the patient requiring treatment is investigated in advance, which, in turn, enables the selection of appropriate peptides having high levels of binding affinity to the patient antigen, or having cytotoxic T cell (CTL) inducibility by antigen presentation. Furthermore, in order to obtain peptides having high binding affinity and CTL inducibility, substitution, deletion, or addition of 1, 2, or several amino acids may be performed based on the amino acid sequence of the naturally occurring MPHOSPH1 and DEPDC1 partial peptide. Herein, the term "several" means refers to 5 or less, more preferably 3 or less. Furthermore, in addition to peptides that are naturally displayed, since the regularity of the sequences of peptides displayed by binding to HLA antigens is already known (Kubo R T, et al., (1994) J. Immunol., 152, 3913-24; Rammensee H G, et al., (1995) Immunogenetics. 41:178-228; Kondo A, et al., (1995) J. Immunol. 155:4307-12), modifications based on such regularity can be performed on the immunogenic peptides of the invention. For example, peptides possessing high HLA-24 binding affinity in which the second amino acid from the N terminus substituted with phenylalanine, tyrosine, methionine, or tryptophan may be favorably used. Likewise, peptides whose C-terminal amino acid is substituted with phenylalanine, leucine, isoleucine, tryptophan, or methionine may also be used favorably. On the other hand, peptides possessing high HLA-A2 binding affinity having their second amino acid from the N terminus substituted with leucine or methionine, and peptides whose C-terminal amino acid is substituted with valine or leucine may be used favorably. Furthermore, 1 to 2 amino acids may be added to the N terminus and/or C terminus of the peptide.

However, when the peptide sequence is identical to a portion of the amino acid sequence of an endogenous or exogenous protein having a different function, side effects such as autoimmune disorders or allergic symptoms against specific substances may be induced. Therefore, it is preferable to avoid the situation wherein the immunogenic sequence matches the amino acid sequence of a known protein. This situation may be avoided by performing a homology search using available databases. If homology searches confirm that peptides in which 1, 2 or several different amino acids do not exist in nature, then the danger that modifications of the above-mentioned amino acid sequence that, for example, increase the binding affinity with HLA antigens, and/or increase the CTL inducibility can be avoided.

Although peptides having high binding affinity to the HLA antigens as described above are expected to be highly effective as cancer vaccines, the candidate peptides, which are selected according to the presence of high binding affinity as an indicator, must be examined for the actual presence of CTL inducibility. CTL inducibility may be routinely confirmed by inducing antigen-presenting cells carrying human MHC antigens (for example, B-lymphocytes, macrophages, and dendritic cells), or more specifically dendritic cells derived from human peripheral blood mononuclear leukocytes, and, after stimulation with the peptide of interest, mixing with CD8-positive cells and measuring the cytotoxic activity against the target cells. As the reaction system, transgenic animals produced to express a human HLA antigen (for example, those described in BenMohamed L, et al., (2000) Hum. Immunol.; 61(8):764-79 Related Articles, Books, Linkout.) may be used. For example, the target cells can be radio-labeled with $^{51}$Cr and such, and cytotoxic activity can be calculated from radioactivity released from the target cells. Alternatively, it can be examined by measuring IFN-gamma produced and released by CTL in the presence of antigen-presenting cells that carry immobilized peptides, and visualizing the inhibition zone on the media using anti-IFN-gamma monoclonal antibodies.

As a result of examining the CTL inducibility of peptides as described above, it was discovered that those peptides having high binding affinity to an HLA antigen did not necessarily have high inducibility. However, nonapeptides or decapeptides selected from the group of peptides having the amino acid sequences indicated by IYNEYIYDL (SEQ ID NO: 7), IYNEyIYDLF (SEQ ID NO: 8), YIYDLFVPV (SEQ ID NO: 9), RLAIFKDLV (SEQ ID NO: 10), TMSSsKLSNV (SEQ ID NO: 11), EYYELFVNI (SEQ ID NO: 12), LLQPHLERV (SEQ ID NO: 192), LLMRMISRM (SEQ ID NO: 195), LLTFEYYEL (SEQ ID NO: 197), RLCKSTIEL (SEQ ID NO: 209), CVLCCAEEV (SEQ ID NO: 225), FLM-DhHQEIL (SEQ ID NO: 228), ILVVcGYITV (SEQ ID NO: 230) DEPDC1-A02-10-644 (SLMIhTFSRC (SEQ ID NO: 240)), DEPDC1-A02-10-575 (SLLPaSSMLT (SEQ ID NO: 241)), DEPDC1-A02-10-506 (QLCRsQSLLL (SEQ ID NO: 243)), DEPDC1-A02-10-765 (KQFQkEYPLI (SEQ ID NO: 244)), DEPDC1-A02-10-395 (IMGGSCHNLI (SEQ ID NO: 249), DEPDC1-A02-10-224 (NMANtSKRGV (SEQ ID NO: 253)), DEPDC1-A02-9-297 (ELFVNILGL (SEQ ID NO: 226)), DEPDC1-A02-10-296 (YELFvNILGL (SEQ ID NO: 254)) and DEPDC1-A02-10-301 (NILGILQPHL (SEQ ID NO: 255)) showed particularly high CTL inducibility.

As noted above, the present invention provides peptides having cytotoxic T cell inducibility, namely those having the amino acid sequence of SEQ ID NOs: 7, 8, 9, 10, 11, 12, 192, 195, 197, 209, 225, 226, 228, 230, 240, 241, 243, 244, 249, 253, 254 or 255 or a variant thereof (i.e., those in which 1, 2, or several amino acids are substituted, deleted, or added). It is preferable that the amino acid sequences composed of 9 or 10 amino acids indicated in SEQ ID NOs: 7, 8, 9, 10, 11, 12, 192, 195, 197, 209, 225, 226, 228, 230, 240, 241, 243, 244, 249, 253, 254 or 255 or a variant thereof do not match an amino acid sequence associated with another endogenous protein. In particular, amino acid substitution to leucine or methionine at the second amino acid from the N terminus, amino acid substitution to valine or leucine at the C-terminal amino acid, and amino acid addition of 1 to 2 amino acids at the N terminus and/or C terminus are examples of preferred variants. One of skill in the art will recognize that in addition to amino acid substitutions and additions, immunologically active fragments of the peptides may also be used in the methods of the invention. Methods for determining active fragments are well known in the art. CTL clones obtained by stimulation by these modified peptides can recognize the original peptides and cause damage for cells expressing the original peptides.

Peptides of the present invention can be prepared using well known techniques. For example, the peptides can be prepared synthetically, using either recombinant DNA technology or chemical synthesis. Peptides of the present invention may be synthesized individually or as longer polypeptides comprising two or more peptides. The peptides of the present invention are preferably isolated, i.e., substantially free of other naturally occurring host cell proteins and fragments thereof.

The peptides of the present invention may contain modifications, such as glycosylation, side chain oxidation, or phosphorylation; so long as the modifications do not destroy the biological activity of the peptides as described herein, namely the ability to binding to an HLA antigen and induce CTL. Other modifications include incorporation of D-amino acids or other amino acid mimetics that can be used, for example, to increase the serum half life of the peptides.

The peptides of this invention can be prepared as a combination, which includes two or more of peptides of the invention, for use as a vaccine for a disease associated with the over-expression of MPHOSPH1 and/or DEPDC1, e.g. cancers, such a vaccine inducing CTL in vivo. The cancers contemplated include, but are not limited to, bladder cancer, breast cancer, cervical cancer, cholangincellular carcinoma, CML, colorectal cancer, gastric cancer, NSCLC, lymphoma, osteosarcoma, prostate cancer, renal carcinoma, SCLC, soft tissue tumor. The peptides may be in a cocktail or may be conjugated to each other using standard techniques. For example, the peptides can be expressed as a single polypeptide sequence. The peptides in the combination may be the same or different. By administering the peptides of this invention, the peptides are presented at a high density on the HLA antigens of antigen-presenting cells, which, in turn, induces CTLs that specifically react toward the complex formed between the displayed peptide and the HLA antigen. Alternatively, antigen-presenting cells having immobilized the peptides of this invention on their cell surface, obtained by removing dendritic cells from the subjects, may be stimulated by the peptides of this invention. Re-administration of these cells to the respective subjects induces CTL, and, as a result, aggressiveness towards the target cells can be increased.

More specifically, the present invention provides drugs for treating and/or preventing proliferation, metastasis, and such of a disease associated with the over-expression of MPHOSPH1 and/or DEPDC1, e.g., cancers, which include one or more of peptides of this invention. The peptides of this invention find particular utility in the treatment of a disease associating MPHOSPH1 and/or DEPDC1, e.g. cancers. The cancers contemplated include, but are not limited to, bladder cancer, breast cancer, cervical cancer, cholangincellular carcinoma, CML, colorectal cancer, gastric cancer, NSCLC, lymphoma, osteosarcoma, prostate cancer, renal carcinoma, SCLC, soft tissue tumor.

The peptides of this invention can be administered to a subject directly, as a pharmaceutical composition that has been formulated by conventional formulation methods. In such cases, in addition to the peptides of this invention, carriers, excipients, and such that are ordinarily used for drugs can be included as appropriate, without particular limitations. The immunogenic compositions of this invention may be used for treatment and prevention of a disease associating MPHOSPH1 and/or DEPDC1, e.g. cancers. The cancers contemplated include, but are not limited to, bladder cancer, breast cancer, cervical cancer, cholangincellular carcinoma, CML, colorectal cancer, gastric cancer, NSCLC, lymphoma, osteosarcoma, prostate cancer, renal carcinoma, SCLC, soft tissue tumor.

The immunogenic compositions for treatment and/or prevention of a disease associated with the over-expression of MPHOSPH1 and/or DEPDC1, e.g. cancers, which comprise as the active ingredient one or more peptides of the present invention, can further include an adjuvant so that cellular immunity will be established effectively. Alternatively, they may be administered with other active ingredients, such as anti-cancer agents. The cancers contemplated include, but are not limited to, bladder cancer, breast cancer, cervical cancer, cholangincellular carcinoma, CML, colorectal cancer, gastric cancer, NSCLC, lymphoma, osteosarcoma, prostate cancer, renal carcinoma, SCLC, soft tissue tumor. Suitable formulations include granules. Suitable adjuvants are described in the literature (Johnson A G. (1994) Clin. Microbiol. Rev., 7:277-89). Exemplary adjuvants include, but are not limited to, aluminum phosphate, aluminum hydroxide, and alum. Furthermore, liposome formulations, granular formulations in which the drug is bound to few-micrometer diameter beads, and formulations in which a lipid is bound to the peptide may be conveniently used. The method of administration may be oral, intradermal, subcutaneous, intravenous injection, or such, and may include systemic administration or local administration to the vicinity of the targeted tumor. The dose of the peptide(s) of this invention can be adjusted appropriately according to the disease to be treated, age of the patient, weight, method of administration, and such. Though the dosage is ordinarily 0.001 mg to 1000 mg, preferably 0.01 mg to 100 mg, more preferably 0.1 mg to 10 mg, preferably administered once in a few days to few months, one skilled in the art can readily select the appropriate dose and method of administration, as, the selection and optimization of these parameters is well within routine skill.

The present invention further provides intracellular vesicles called exosomes, which present complexes formed between the peptides of this invention and HLA antigens on their surface. Exosomes can be prepared, for example, by using the methods described in detail in Published Japanese Translation of International Publication Nos. Hei 11-510507 and 2000-512161, and are preferably prepared using antigen-presenting cells obtained from subjects who are targets of treatment and/or prevention. The exosomes of this invention can be inoculated as cancer vaccines, similarly to the peptides of this invention.

The type of HLA antigens used must match that of the subject requiring treatment and/or prevention. For example, in the Japanese population, HLA-A24 or HLA-A2, particularly HLA-A2402 or HLA-A0201, is often appropriate.

In some embodiments, the vaccine compositions of the present invention include a component which primes cytotoxic T lymphocytes. Lipids have been identified as agents capable of priming CTL in vivo against viral antigens. For example, palmitic acid residues can be attached to the epsilon- and alpha-amino groups of a lysine residue and then linked to an immunogenic peptide of the invention. The lipidated peptide can then be administered either directly, in a' micelle or particle, incorporated into a liposome, or emulsified in an adjuvant. As another example of a lipid priming of CTL responses, $E.$ $coli$ lipoproteins, such as tripalmitoyl-S-glycerylcysteinlyseryl-serine (P3CSS), can be used to prime CTL when covalently attached to an appropriate peptide (see, e.g., Deres K, et al., (1989) Nature 342:561-4).

The immunogenic compositions of the present invention may also include nucleic acids encoding one or more of the immunogenic peptides disclosed here. See, e.g., Wolff J A et al., (1990) Science 247:1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

The immunogenic peptides of the invention can also be expressed by viral or bacterial vectors. Examples of suitable expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another suitable vector is BCG (Bacille Calmette Guerin). BCG vectors are described in Stover C K, et al., (1991) Nature 351:456-60. A wide variety of other vectors useful for therapeutic administration or immunization e.g., adeno and adeno-associated virus vectors, retroviral vectors, $Salmonella$ $typhia$ vectors, detoxified anthrax toxin vectors, and the like, are known in the art. See, e.g., Shata M T, et al., (2000) Mol. Med. Today 6:66-71; Shedlock D J and Weiner D B., et al., (2000) J. Leukoc. Biol. 68:793-806; and Hipp J D, et al., (2000) In Vivo 14:571-85.

The present invention also provides methods of inducing antigen-presenting cells using one or more peptides of this invention. The antigen-presenting cells can be induced by inducing dendritic cells from the peripheral blood monocytes and then contacting (stimulating) them with one or more peptides of this invention in vitro, ex vivo or in vivo. When peptides of the present invention are administered to the subjects, antigen-presenting cells that have the peptides of this invention immobilized to them are induced in the body of the subject. Alternatively, after immobilizing the peptides of this invention to the antigen-presenting cells, the cells can be administered to the subject as a vaccine. For example, the ex vivo administration may include the steps of:

a: collecting antigen-presenting cells from a subject, and b: contacting the antigen-presenting cells of step a with a peptide of the present invention.

The antigen-presenting cells obtained by step b can be administered to the subject as a vaccine.

This invention also provides a method for inducing antigen-presenting cells having a high level of cytotoxic T cell inducibility, in which the method includes the step of transferring genes composed of polynucleotide(s) encoding one or more peptides of this invention to antigen-presenting cells in vitro. The introduced genes may be in the form of DNAs or RNAs. For the method of introduction, without particular limitations, various methods conventionally performed in this field, such as lipofection, electroporation, and calcium phosphate method may be suitably used. More specifically, transfection may be performed as described in Reeves M E, et al., (1996) Cancer Res., 56:5672-7; Butterfield L H, et al., (1998) J. Immunol., 161:5607-13; Boczkowski D, et al., (1996) J. Exp. Med., 184:465-72; Published Japanese Translation of International Publication No. 2000-509281. By transferring the gene into antigen-presenting cells, the gene undergoes transcription, translation, and such in the cell, and then the obtained protein is processed by MHC Class I or Class II, and proceeds through a presentation pathway to present partial peptides.

The present invention further provides methods for inducing CTL using one or more peptides of this invention. When the peptides of this invention are administered to a subject, CTL are induced in the body of the subject, and the strength of the immune system targeting the cells expressing MPHOSPH1 and/or DEPDC1, e.g. cancer cells in the tumor tissues is thereby enhanced. The cancers contemplated include, but are not limited to, bladder cancer, breast cancer, cervical cancer, cholangincellular carcinoma, CML, colorectal cancer, gastric cancer, NSCLC, lymphoma, osteosarcoma, prostate cancer, renal carcinoma, SCLC, soft tissue tumor. Alternatively, the peptides of the present invention may be used in the context of an ex vivo therapeutic method, in which subject-derived antigen-presenting cells and CD8-positive cells or peripheral blood mononuclear leukocytes are contacted (stimulated) with one or more peptides of this invention in vitro, and, after inducing CTL, the cells are returned to the subject. For example, the method may include the steps of:

a: collecting antigen-presenting cells from a subject, b: contacting the antigen-presenting cells of step a with a peptide of the present invention, c: mixing the antigen-presenting cells of step b with $CD^{8+}$ T cells and co-culturing so as to induce cytotoxic T-cells, and d: collecting $CD^{8+}$ T cells from the co-culture of step c.

The $CD^{8+}$ T cells having cytotoxic activity obtained by step d can be administered to the subject as a vaccine.

The present invention further provides methods for producing activated cytotoxic T cell using the peptides of this invention. For example, the method may include the following steps of:
a: collecting T cells from a subject, and
b: contacting T cells with following peptides.
(1) An isolated peptide of less than about 15 amino acids selected from the group consisting of peptides having the amino acid sequences of SEQ ID NOs: 7, 8, 9, 10, 11, 12, 192, 195, 197, 209, 225, 226, 228, 230, 240, 241, 243, 244, 249, 253, 254 and 255.
(2) A peptide having cytotoxic T cell inducibility, wherein said peptide has an amino acid sequence selected from the group consisting of SEQ ID NOs: 7, 8, 9, 10, 11, 12, 192, 195, 197, 209, 225, 226, 228, 230, 240, 241, 243, 244, 249, 253, 254 and 255, wherein 1, 2, or several amino acids are substituted, deleted, or added.

The present invention also provides method for producing APC having activated T-cell inducibility using the peptides of the present invention. For instance, the method may include the step of contacting antigen presenting cells with the peptides to produce antigen presenting cells presenting the peptide and HLA antigen on the surface.

In the context of the present invention, "activated cytotoxic T cell" induces IFN-gamma producing, IFN-gamma releasing, and death of tumor cells.

The present invention further provides isolated cytotoxic T cells induced using the peptides of this invention. The cytotoxic T cells, induced by stimulation with an antigen-presenting cell presenting one or more peptides of this invention, are preferably derived from subjects who are the target of treatment and/or prevention, and can be administered alone or in combination with other drugs, including one or more peptides of this invention or exosomes having anti-tumor activity. The obtained cytotoxic T cells act specifically against target cells presenting the peptides of this invention, or preferably the same peptide(s) used for induction. The target cells may be cells that express MPHOSPH1 and/or DEPDC1 endogenously, or cells that are transfected with MPHOSPH1 and/or DEPDC1 genes. Cells that present the peptides of this invention on the cell surface, due to stimulation with these peptides, can also become targets of attack.

The present invention also provides antigen-presenting cells presenting complexes formed between HLA antigens and one or more peptides of this invention. The antigen-presenting cells, obtained through contact with the peptides of this invention or the nucleotides encoding such peptides, are preferably derived from subjects who are the target of treatment and/or prevention, and can be administered as vaccines, alone or in combination with other drugs, including the peptides, exosomes, or cytotoxic T cells of the present invention.

The present invention also provides a composition comprising nucleic acids encoding polypeptides that are capable of forming a subunit of a T cell receptor (TCR), and methods of using the same. The TCR subunits have the ability to form TCRs that confer specificity to T cells for tumor cells presenting MPHOSPH1 or DEPDC1. By using the known method in the art, the nucleic acids of alpha- and beta-chain as the TCR subunits of the CTL induced with one or more peptides of this invention may be identified (WO2007/032255 and Morgan et al., J Immunol, 171, 3288 (2003)). The derivative TCRs preferably bind target cells displaying the MPHOSPH1 or DEPDC1 peptide with high avidity, and optionally mediate efficient killing of target cells presenting the MPHOSPH1 or DEPDC1 peptide in vivo and in vitro.

The nucleic acids encoding the TCR subunits can be incorporated into suitable vectors e.g. retroviral vectors. These vectors are well known in the art. The nucleic acids or the vectors comprising them usefully can be transferred into a T cell, which T cell is preferably from a patient. Advantageously, the invention provides an off-the-shelf composition allowing rapid modification of a patient's own T cells (or those of another mammal) to rapidly and easily produce modified T cells having excellent cancer cell killing properties.

Also, the present invention provides CTLs which are prepared by transduction with the nucleic acids encoding the TCR subunits polypeptides binding with MPHOSPH1 or DEPDC1 peptide e.g. SEQ ID NOs: 7, 8, 9, 10, 11, 12, 192, 195, 197, 209, 225, 226, 228, 230, 240, 241, 243, 244, 249, 253, 254 or 255 in the context of HLA-A24 or HLA-A2. The transduced CTLs are capable of homing to cancer cells in vivo, and expanded by well known culturing method in vitro (e.g., Kawakami et al., J. Immunol., 142, 3452-3461 (1989)). The T cells of the invention can be used to form an immunogenic composition useful in treating or preventing cancer in a patient in need of therapy or protection (WO2006/031221).

In the context of the present invention, the term "vaccine" (also referred to as an immunogenic composition) refers to a substance that induces anti-tumor immunity or suppresses cancers upon inoculation into animals. According to the present invention, polypeptides having the amino acid sequence of SEQ ID NO: 7, 8 or 12 were suggested to be HLA-A24 restricted epitope peptides and those of SEQ ID NO: 9, 10, 11, 192, 195, 197, 209, 225, 226, 228, 230, 240, 241, 243, 244, 249, 253, 254 or 255 were suggested to be HLA-A2 restricted epitope peptides that may induce potent and specific immune response against cells expressing MPHOSPH1 and/or DEPDC1, e.g. cancer cells expressing MPHOSPH1 and/or DEPDC1. The cancers contemplated include, but are not limited to, bladder cancer, breast cancer, cervical cancer, cholangincellular carcinoma, CML, colorectal cancer, gastric cancer, NSCLC, lymphoma, osteosarcoma, prostate cancer, renal carcinoma, SCLC, soft tissue tumor. Thus, the present invention also encompasses a method of inducing anti-tumor immunity using polypeptides having the amino acid sequence of SEQ ID NO: 7, 8, 9, 10, 11, 12, 192, 195, 197, 209, 225, 226, 228, 230, 240, 241, 243, 244, 249, 253, 254 or 255 or a variant thereof (i.e., including 1, 2, or several amino acid substitutions, deletions, or additions). In general, anti-tumor immunity includes immune responses such as follows:

an induction of cytotoxic lymphocytes against tumors containing cells expressing MPHOSPH1 and/or DEPDC1,
an induction of antibodies that recognize tumors containing cells expressing MPHOSPH1 and/or DEPDC1, and
an induction of anti-tumor cytokine production.

Therefore, when a certain peptide induces any one of these immune responses upon inoculation into an animal, the peptide is decided to have anti-tumor immunity inducing effect. The induction of the anti-tumor immunity by a peptide can be detected by observing in vivo or in vitro the response of the immune system in the host against the peptide.

For example, a method for detecting the induction of cytotoxic T lymphocytes is well known. A foreign substance that enters the living body is presented to T cells and B cells by the action of antigen-presenting cells (APCs). T cells that respond to the antigen presented by APC in antigen specific manner differentiate into cytotoxic T cells (also referred to as cytotoxic T lymphocytes or CTLs) due to stimulation by the antigen, and then proliferate; this process is referred to herein as "activation" of T cells. Therefore, CTL induction by a certain peptide can be evaluated by presenting the peptide to a T cell by APC, and detecting the induction of CTL. Furthermore, APCs have the effect of activating CD4+ T cells, CD8+ T cells, macrophages, eosinophils and NK cells. Since CD4+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC and then this DC is contacted with T cells. Detection of T cells having cytotoxic effects against the cells of interest after the contact with DC shows that the test polypeptide has an activity of inducing the cytotoxic T cells. Activity of CTL against tumors can be detected, for example, using the lysis of $^{51}$Cr-labeled tumor cells as the indicator. Alternatively, it is well known to evaluate the degree of tumor cell damage using $^{3}$H-thymidine uptake activity or LDH (lactose dehydrogenase)-release as the indicator. Furthermore, it can be also examined by measuring IFN-gamma produced and released by CTL in the presence of antigen-presenting cells that carry immobilized peptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against tumor cells are useful as vaccines against diseases associated with the over-expression of MPHOSPH1 and/or DEPDC1, e.g. cancers. Furthermore, APC that have acquired the ability to induce CTL against a disease associating MPHOSPH1 and/or DEPDC1, e.g. cancers, by contacting with the polypeptides are useful as vaccines against the disease. Furthermore, CTL that have acquired cytotoxicity due to presentation of the polypeptide antigens by APC can be also used as vaccines against a disease associating MPHOSPH1 and/or DEPDC1, e.g. cancers. Such therapeutic methods for a disease associating MPHOSPH1 and/or DEPDC1, e.g. cancers, using anti-tumor immunity due to APC and CTL, are referred to as cellular immunotherapy. The cancers contemplated include, but are not limited to, bladder cancer, breast cancer, cervical cancer, cholangincellular carcinoma, CML, colorectal cancer, gastric cancer, NSCLC, lymphoma, osteosarcoma, prostate cancer, renal carcinoma, SCLC, soft tissue tumor.

Generally, when using a polypeptide for cellular immunotherapy, efficiency of the CTL-induction can be increased by combining a plurality of polypeptides having different structures and contacting them with DC. Therefore, when stimulating DC with protein fragments, it is advantageous to use a mixture of multiple types of fragments.

The induction of anti-tumor immunity by a polypeptide can be further confirmed by observing the induction of antibody production against tumors. For example, when antibodies against a polypeptide are induced in a laboratory animal immunized with the polypeptide, and when growth, proliferation and/or metastasis of tumor cells is suppressed by those antibodies, the polypeptide is determined to induce anti-tumor immunity.

Anti-tumor immunity can be induced by administering a vaccine of this invention, and the induction of anti-tumor immunity enables treatment and prevention of a disease associated with the over-expression of MPHOSPH1 and/or DEPDC1, e.g. cancers. Therapy against or prevention of the onset of a disease associated with the over-expression of MPHOSPH1 and/or DEPDC1, e.g. cancers, may include inhibition of the growth of cells expressing MPHOSPH1 and/or DEPDC1, e.g. cancer cells, involution of these cells and suppression of occurrence of these cells, e.g. cancer cells. Decrease in mortality of individuals having a disease associating MPHOSPH1 and/or DEPDC1, e.g. cancers, decrease of the disease markers in the blood, alleviation of detectable symptoms accompanying the disease and such are also included in the therapy or prevention of the disease, e.g. cancers. Such therapeutic and preventive effects are preferably statistically significant, for example, observed at a significance level of 5% or less, wherein the therapeutic or preventive effect of a vaccine against a disease associating MPHOSPH1 and/or DEPDC1, e.g. cancers, is compared to a control without vaccine administration. For example, Student's t-test, the Mann-Whitney U-test or ANOVA may be used for determining statistical significance.

In that the present invention provides a method for treating, or preventing a disease associated with the over-expression of MPHOSPH1 and/or DEPDC1, e.g. cancers, the therapeutic compounds or compositions may be administered prophylactically or therapeutically to subjects suffering from or at risk of (or susceptible to) developing the disease. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur "t primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

In the context of cancer treatment, the term "efficacious" refers to a treatment that leads to a decrease in size, prevalence or metastatic potential of cancer in a subject. When a treatment is applied prophylactically, "efficacious" means that the treatment retards or prevents occurrence of non cancer or alleviates a clinical symptom of cancer. The assessment of cancer can be made using standard clinical protocols. Furthermore, the efficaciousness of a treatment may be determined in association with any known method for diagnosing or treating cancer. For example, cancer can be diagnosed histopathologically or by identifying symptomatic anomalies.

The above-mentioned peptide, having immunological activity, or a polynucleotide or vector encoding such a peptide, may be combined with an adjuvant. An adjuvant refers to a compound that enhances the immune response against the peptide when administered together (or successively) with the peptide having immunological activity. Examples of suitable adjuvants include cholera toxin, *salmonella* toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

When using APC or CTL as the vaccine of this invention, a disease associated with the over-expression of MPHOSPH1 and/or DEPDC1, e.g. cancers, can be treated or prevented, for example, by the ex vivo method. More specifically, PBMCs of the subject receiving treatment or prevention are collected, contacted ex vivo with a peptide of the present invention. Following the induction of APC or CTL, the cells may be administered to the subject. APC can be also induced by introducing a vector encoding the peptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of diseases in other individuals.

Aspects of the present invention are described in the following examples, which are presented only to illustrate the present invention and to assist one of ordinary skill in making and using the same. The examples are not intended in any way to otherwise limit the scope of the invention.

Although methods and materials similar or equivalent to those described herein can be used in the practice or testing of the present invention, suitable methods and materials are described below.

EXAMPLES

Hereinafter, the present invention is exemplified, but not restricted, by the following Examples. However, materials, methods and such described herein only illustrate aspects of the invention and in no way are intended to limit the scope of the present invention. As such, materials, methods and such similar or equivalent to those described therein may be used in the practice or testing of the present invention.

Example 1

Materials and Methods
Cell Lines
A24LCL cells (HLA-A24/24), human B-lymphoblastoid cell lines, T2 cell and COST were purchased from ATCC.
Candidate Selection of Peptide Derived from MPHOSOH1 and DEPDC1

9-mer and 10-mer peptides derived from MPHOSOH1 or DEPDC1 that bind to HLA-A*2402 and HLA-A*0201 molecule were predicted using binding prediction software "BIMAS" (bimas.dcrtnih.gov/cgi-bin/molbio/ken_parker_comboform) (Parker K C, et al., (1994) J. Immunol.; 152(1): 163-75; Kuzushima K, et al., (2001) Blood; 98(6):1872-81). These peptides were synthesized by Sigma (Sapporo, Japan) according to the standard solid phase synthesis method and purified by reversed phase HPLC. The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce CTL responses against peptides presented on HLA. DCs were generated in vitro as described elsewhere (Nukaya I et al., (1999) Int. J. Cancer 80, 92-7, Tsai V et al., (1997) J. Immunol. 158:1796-802). Briefly, peripheral blood mononuclear cells (PBMCs) isolated from a normal volunteer (HLA-A*2402 and/or HLA-A*0201) by Ficoll-Paque (Pharmacia) solution were separated by adherence to a plastic tissue culture flask (Becton Dickinson) so as to enrich them for the monocyte fraction. The monocyte-enriched population was cultured in the presence of 1000 U/ml of GM-CSF (Genzyme) and 1000 U/ml of IL-4 (Genzyme) in AIM-V (Invitrogen) containing 2% heat-inactivated autologous serum (AS). After 7 days in the culture, the cytokine-generated DCs were pulsed with 20 mcg/ml of the synthesized peptides in the presence of 3 mcg/ml of beta 2-microglobulin for 4 hrs at 20 degrees C. in AIM-V. These peptide-pulsed DCs were then inactivated by MMC (30 mcg/ml for 30 mins) and mixed at a 1:20 ratio with autologous CD8+ T cells, obtained by positive selection with Dynabeads M-450 CD8 (Dynal) and DETACHa BEAD™ (Dynal). These cultures were set up in 48-well plates (Corning); each well contained $1.5 \times 10^4$ peptide-pulsed DCs, $3 \times 10^5$ CD8+ T cells and 10 ng/ml of IL-7 (Genzyme) in 0.5 ml of AIM-V/2% AS. Three days later, these cultures were supplemented with IL-2 (CHIRON) to a final concentration of 20 IU/ml. On day 7 and 14; the T cells were further restimulated with the autologous peptide-pulsed DCs. The DCs were prepared each time by the same way described above. CTL was tested against peptide-pulsed A24LCL cells or T2 cells after the 3rd round of peptide stimulation on day 21.

CTL Expansion Procedure

CTLs were expanded in culture using the method similar to that described by Riddell S R, et al., (Walter E A et al., (1995) N Engl J Med 333:1038-44; Riddel S R, et al., (1996) Nature Med. 2:216-23). A total $5 \times 10^4$ of CTLs were resuspended in 25 ml of AIM-V/5% AS with 2 kinds of human B-lymphoblastoid cell lines, inactivated by MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS containing 30 IU/ml of IL-2 on days 5, 8 and 11.

Establishment of CTL Clones

The dilutions were made to have 0.3, 1, and 3 CTLs/well in 96 round-bottomed micro titer plate (Nalge Nunc International). CTLs were cultured with $7 \times 10^4$ cells/well of 2 kinds of human B-lymphoblastoid cell lines, 30 ng/ml of anti-CD3 antibody, and 125 U/ml of IL-2 in total of 150 mcl/well of AIM-V containing 5% AS. 50 mcl/well of IL-2 was added to the medium 10 days later so that IL-2 became 125 U/ml in the final concentration. CTL activity of CTLs was tested on the 14th day, and CTL clones were expanded using the same method above.

Specific CTL Activity

To examine the specific CTL activity, IFN-gamma ELISPOT assay and IFN-gamma ELISA were performed.

Briefly, peptide-pulsed A24-LCL or T2 cell ($1\times10^4$/well) was prepared as a stimulator cell. Cultured Cells in 48 wells or CTL clones after limiting dilution were used as a responder cells. IFN-gamma ELISPOT assay and ELISA were performed under manufacture procedure.

Cell Culture and Transfection

HLA-A24 B-LCLs (A24LCL), Epstein Bar virus-transformed, was established. Jiyoye, EB-3, COS7, HT1376, RT-4 and J82 were purchased from American Type Culture Collection (Rockville, Md.). A24LCL, Jiyoye and EB-3 were maintained in RPMI1640 containing 10% fetal bovine serum (GEMINI Bio-Products) and 1% antibiotic solution (Sigma). COS7, HT1376, RT-4 and J82 were maintained in appropriate medium and antibiotics. Transfection of COS7 and HEK were performed using FUGENE6 (Roche). HEK-A2 cell, HLA-A*0201 molecule expressing stable clone, was established by transfection of pcDNA6.2-HLA-A2 plasmid and isolated by limiting dilution method in the presence of 5 mcg/ml Blastcidin S.

Immunogenicity of Epitope Peptides in BALB/c Mice

For induction of the peptide-specific CTLs, immunization was given using 100 ml of vaccine mixture, which contains 50 mcl (100 mcg) of HLA-A24 restricted peptide and 50 mcl of IFA per mouse. The vaccine was subcutaneously injected in the right flank for the first immunization on day 0 and in the left flank for the second on the day 7. On day 14, splenocytes of the vaccinated mice, without any in vitro stimulation, were used responder cells, and RLmale1 cells pulsed with or without peptides were used as the stimulator cells for IFN-gamma ELISPOT assay.

Results

Enhanced MPHOSPH1 and DEPDC1 Expression in Cancers

The global gene expression profile data obtained from various cancers using cDNA-microarray revealed that MPHOSPH1 (GenBank Accession No. NM_016195; SEQ ID No.1) and DEPDC1 (GenBank Accession No. BM683578) which had two variants; DEPDC1 V1 (SEQ ID Nos.3) and DEPDC1 V2 (SEQ ID No. 5) expression was elevated. MPHOSPH1 expression was validly elevated in 30 out of 31 bladder cancers, 8 out of 36 breast cancers, 18 out of 18 cervical cancers, 5 out of 17 cholangincellular carcinomas, 25 out of 31 CMLs, 6 out of 11 colorectal cancers, 6 out of 14 gastric cancers, 5 out of 5 NSCLCs, 7 out of 7 lymphomas, 6 out of 10 osteosarcomas, 7 out of 22 prostate cancers, 10 out of 18 renal carcinomas and 15 out of 21 soft tissue tumors as compared with corresponding normal tissue. DEPDC1 expression was validly elevated in 23 out of 25 bladder cancers, 6 out of 13 breast cancers, 12 out of 12 cervical cancers, 6 out of 6 cholangincellular carcinomas, 3 out of 4 CMLs, 2 out of 4 colorectal cancers, 6 out of 6 NSCLCs, 7 out of 7 lymphomas, 10 out of 14 osteosarcomas, 11 out of 24 prostate cancers, 14 out of 14 SCLCs and 22 out of 31 soft tissue tumors as compared with corresponding normal tissue (Table 1).

TABLE 1

Ratio of cases observed up-regulation of MPHOSPH1 or DEPDC1 in cancerous tissue as compared with normal corresponding tissue

| | Bladder cancer | Breast cancer | Cervical cancer | Cholangiocellular Carcinoma | CML | Colorectal cancer | Gastric cancer |
|---|---|---|---|---|---|---|---|
| MPHOSPH1 | 30/31 | 8/36 | 18/18 | 5/17 | 25/31 | 6/11 | 6/14 |
| DEPDC1 | 23/25 | 6/13 | 12/12 | 6/6 | 3/4 | 2/4 | — |

| | NSCLC | Lymphoma | Osteosarcoma | Prostate cancer | Renal cancer | SCLC | Soft Tissue Tumor |
|---|---|---|---|---|---|---|---|
| MPHOSPH1 | 5/5 | 7/7 | 6/10 | 7/22 | 10/18 | — | 15/21 |
| DEPDC1 | 6/6 | 7/7 | 10/14 | 11/24 | — | 14/14 | 22/31 |

Prediction of HLA-A24 and HLA-A2 Binding Peptides Derived from MPHOSPH1 or DEPDC1

Table 2 sets forth the HLA-A*2402 binding peptides for MPHOSPH1 in order of binding affinity. Table 2A sets forth 9-mer peptides derived from MPHOSPH1 and Table 2B sets forth 10-mer peptides derived from MPHOSPH1.

Table 3 sets forth the HLA-A*0201 binding peptides for MPHOSPH1 in order of binding affinity. Table 3A sets forth 9-mer peptides derived from MPHOSPH1 and Table 3B sets forth 10-mer peptides derived from MPHOSPH1.

Table 4 sets forth the HLA-A*2402 binding peptides for DEPDC1 V1 and V2 in order of binding affinity. Table 4A sets forth 9-mer peptides derived from DEPDC1 V1 and V2 and Table 4B sets forth 10-mer peptides derived from DEPDC1 V1.

Table 5 sets forth the HLA-A*0201 binding peptides for DEPDC1 V1 and V, Table 5A sets forth 9-mer peptides derived from DEPDC1 V1 and V2 and Table 5B sets forth 10-mer peptides derived from DEPDC 1 V1 and V2.

TABLE 2A

HLA-A*2402 binding 9-mer peptides derived from MPHOSPH1

| Start Position | Amino Acid Sequence | SEQ ID NO. | Binding Score | Start Position | Amino Acid Sequence | SEQ ID NO. | Binding Score |
|---|---|---|---|---|---|---|---|
| 278 | IYNEYIYDL | 7 | 360 | 179 | LFDSLQERL | 29 | 24 |
| 1244 | DYADLKEKL | 13 | 316.8 | 268 | KFSVWVSFF | 30 | 20 |
| 1319 | QYERACKDL | 14 | 300 | 575 | KLLDLIEDL | 31 | 17.28 |
| 459 | CYLAYDETL | 15 | 300 | 1577 | RFPKPELEI | 32 | 16.5 |
| 462 | AYDETLNVL | 16 | 288 | 1414 | KYNADRKKW | 33 | 16.5 |
| 1054 | GYKDENNRL | 17 | 288 | 1230 | RTQNLKADL | 34 | 14.4 |
| 236 | LYGSLTNSL | 18 | 288 | 1421 | KWLEEKMML | 35 | 14.4 |
| 1446 | KYAEDRERF | 19 | 240 | 1617 | KSNEMEEDL | 36 | 14.4 |
| 899 | NYDIAIAEL | 20 | 220 | 1555 | KIEDGSVVL | 37 | 14.4 |
| 1118 | CYKAKIKEL | 21 | 220 | 1456 | KQQNEMEIL | 38 | 12 |
| 57 | DYLQVCLRI | 22 | 105 | 389 | KTQNEGERL | 39 | 12 |
| 676 | KFNQIKAEL | 23 | 92.4 | 1371 | KWKEKCNDL | 40 | 11.52 |
| 14 | SYVFSADPI | 24 | 75 | 1122 | KIKELETIL | 41 | 11.52 |
| 326 | AYRLLKLGI | 25 | 60 | 850 | FLLTIENEL | 42 | 11.088 |
| 255 | DYEQANLNM | 26 | 37.5 | 763 | SSLIINNKL | 43 | 11.088 |
| 29 | NFDGIKLDL | 27 | 28 | 1400 | KLTNLQDEL | 44 | 10.56 |
| 286 | LFVPVSSKF | 28 | 27.72 | 133 | IMQPVKDLL | 45 | 10.08 |

Start position indicates the number of amino acid from N-terminal of MPHOSPH1. Binding score is derived from "BIMAS" described in Materials and Methods.

TABLE 2B

HLA-A*2402 binding 10-mer peptides derived from MPHOSPH1

| Start Position | Amino Acid Sequence | SEQ ID NO. | Binding Score | Start Position | Amino Acid Sequence | SEQ ID NO. | Binding Score |
|---|---|---|---|---|---|---|---|
| 1414 | KYNAdRKKWL | 46 | 600 | 1274 | KLLRiKINEL | 56 | 15.84 |
| 278 | IYNEyIYDLF | 8 | 252 | 1332 | KIIEdMRMTL | 57 | 14.4 |
| 1446 | KYAEdRERFF | 47 | 240 | 1299 | RTIQqLKEQL | 58 | 14.4 |
| 611 | QYWAqREADF | 48 | 100 | 1134 | KVECsHSAKL | 59 | 13.2 |
| 1740 | LYTSeISSPI | 49 | 70 | 859 | KNEKeEKAEL | 60 | 13.2 |
| 293 | KFQKrKMLRL | 50 | 60 | 586 | KLINeKKEKL | 61 | 13.2 |
| 849 | AFLLtIENEL | 51 | 55.44 | 943 | KLMHtKIDEL | 62 | 13.2 |
| 1667 | TYSLrSQASI | 52 | 50 | 838 | RVLQeNNEGL | 63 | 12 |
| 1695 | DFLQhSPSIL | 53 | 30 | 369 | RVIRvSELSL | 64 | 12 |
| 174 | RTLNvLFDSL | 54 | 17.28 | 1159 | RNLKeFQEHL | 65 | 12 |
| 870 | KQIVhFQQEL | 55 | 15.84 | 281 | EYIYdLFVPV | 66 | 10.8 |

Start position indicates the number of amino acid from N-terminal of MPHOSPH1. Binding score is derived from "BIMAS" described in Materials and Methods.

TABLE 3A

| \multicolumn{4}{|c|}{HLA-A*0201 binding 9-mer peptides derived from MPHOSPH1} | | | | |
|---|---|---|---|---|---|---|---|
| Start Position | Amino Acid Sequence | SEQ ID NO. | Binding Score | Start Position | Amino Acid Sequence | SEQ ID NO. | Binding Score |
| 575 | KLLDLIEDL | 31 | 1278.29 | 1184 | KLKEEITQL | 93 | 24.677 |
| 282 | YIYDLFVPV | 9 | 1096.62 | 888 | TLSKEVQQI | 94 | 23.995 |
| 298 | KMLRLSQDV | 67 | 650.504 | 280 | NEYIYDLFV | 95 | 23.802 |
| 218 | ALLRQIKEV | 68 | 591.888 | 552 | LLDEDLDKT | 96 | 23.415 |
| 850 | FLLTIENEL | 42 | 363.588 | 461 | LAYDETLNV | 97 | 21.546 |
| 1108 | ALSELTQGV | 69 | 285.163 | 980 | NLPNTQLDL | 98 | 21.362 |
| 331 | KLGIKHQSV | 70 | 243.432 | 409 | TLGKCINVL | 99 | 20.145 |
| 1689 | TLQKFGDFL | 71 | 218.772 | 175 | TLNVLFDSL | 100 | 19.888 |
| 1251 | KLTDAKKQI | 72 | 149.711 | 923 | KLSNEIETA | 101 | 19.596 |
| 638 | RLAIFKDLV | 10 | 129.506 | 1389 | KEHENNTDV | 102 | 19.407 |
| 1467 | QLTEKDSDL | 73 | 87.586 | 987 | DLLGNDYLV | 103 | 19.301 |
| 1195 | NLQDMKHLL | 74 | 87.586 | 920 | KIMKLSNEI | 104 | 18.577 |
| 270 | SVWVSFFEI | 75 | 83.497 | 1703 | ILQSKAKKI | 105 | 17.736 |
| 129 | FQGCIMQPV | 76 | 74.608 | 512 | ILNVKRATI | 106 | 17.736 |
| 839 | VLQENNEGL | 77 | 72.959 | 1124 | KELETILET | 107 | 17.695 |
| 1094 | TLDVQIQHV | 78 | 63.988 | 453 | IVNISQCYL | 108 | 17.477 |
| 1019 | AIWEECKEI | 79 | 48.816 | 771 | LICNETVEV | 109 | 16.258 |
| 1696 | FLQHSPSIL | 80 | 40.289 | 623 | TLLQEREIL | 110 | 15.879 |
| 528 | DLMEDEDLV | 81 | 38.775 | 560 | TLEENKAFI | 111 | 15.057 |
| 406 | SLLTLGKCI | 82 | 38.601 | 1415 | YNADRKKWL | 112 | 14.465 |
| 1400 | KLTNLQDEL | 44 | 36.637 | 307 | KGYSFIKDL | 113 | 13.65 |
| 170 | GILPRTLNV | 83 | 35.385 | 133 | IMQPVKDLL | 45 | 12.852 |
| 171 | ILPRTLNVL | 84 | 34.246 | 1594 | KMAVKHPGC | 114 | 12.558 |
| 786 | KICSERKRV | 85 | 33.472 | 365 | SEMSRVIRV | 115 | 11.509 |
| 880 | SLSEKKNLT | 86 | 30.553 | 1191 | QLTNNLQDM | 116 | 11.426 |
| 944 | LMHTKIDEL | 87 | 29.559 | 871 | QIVHFQQEL | 117 | 11.162 |
| 1422 | WLEEKMMLI | 88 | 28.963 | 245 | NISEFEESI | 118 | 10.951 |
| 466 | TLNVLKFSA | 89 | 28.814 | 484 | TLNSSQEKL | 119 | 10.468 |
| 1539 | KLQTEPLST | 90 | 26.082 | 764 | SLIINNKLI | 120 | 10.433 |
| 132 | CIMQPVKDL | 91 | 24.997 | 587 | LINEKKEKL | 121 | 10.032 |
| 1260 | KQVQKEVSV | 92 | 24.681 | | | | |

Start position indicates the number of amino acid from N-terminal of MPHOSPH1. Binding score is derived from "BIMAS" described in Materials and Methods.

TABLE 3B

HLA-A*0201 binding 10-mer peptides derived from MPHOSPH1

| Start Position | Amino Acid Sequence | SEQ ID NO. | Binding Score | Start Position | Amino Acid Sequence | SEQ ID NO. | Binding Score |
|---|---|---|---|---|---|---|---|
| 1274 | KLLRiKINEL | 56 | 626.279 | 1318 | QQYErACKDL | 140 | 28.417 |
| 551 | KLLDeDLDKT | 122 | 445.913 | 452 | MIVNiSQCYL | 141 | 27.464 |
| 460 | YLAYdETLNV | 123 | 319.939 | 923 | KLSNeIETAT | 142 | 26.082 |
| 943 | KLMHtKIDEL | 62 | 311.777 | 1257 | KQIKqVQKEV | 143 | 24.681 |
| 262 | NMANsIKFSV | 124 | 291.346 | 980 | NLPNtQLDLL | 144 | 24.075 |
| 178 | VLFDsLQERL | 125 | 269.948 | 985 | QLDLlGNDYL | 145 | 23.029 |
| 770 | KLICnETVEV | 126 | 243.432 | 1427 | MMLItQAKEA | 146 | 22.569 |
| 34 | KLDLsHEFSL | 127 | 173.463 | 1523 | QIMDiKPKRI | 147 | 21.762 |
| 407 | LLTLgKCINV | 128 | 118.238 | 1484 | QLVAaLEIQL | 148 | 21.362 |
| 1714 | TMSSsKLSNV | 11 | 115.534 | 466 | TLNV1KFSAI | 149 | 19.822 |
| 1353 | QVLEaKLEEV | 129 | 104.046 | 511 | KILNvKRATI | 150 | 18.577 |
| 880 | SLSEkKNLTL | 130 | 87.586 | 1340 | TLEEqEQTQV | 151 | 18.25 |
| 235 | TLYGsLTNSL | 131 | 68.36 | 372 | RVSE1SLCDL | 152 | 17.627 |
| 1019 | AIWEeCKEIV | 132 | 65.381 | 1561 | VVLDsCEVST | 153 | 16.816 |
| 552 | LLDEdLDKTL | 133 | 59.558 | 309 | YSFIkDLQWI | 154 | 14.663 |
| 1093 | VTLDvQIQHV | 134 | 57.298 | 353 | SIFTvKILQI | 155 | 12.208 |
| 559 | KTLEeNKAFI | 135 | 42.314 | 1094 | TLDVqIQHVV | 156 | 11.407 |
| 1332 | KIIEdMRMTL | 57 | 42.151 | 1688 | GTLQkFGDFL | 157 | 11.242 |
| 152 | GLTNsGKTYT | 136 | 40.986 | 311 | FIKD1QWIQV | 158 | 10.732 |
| 830 | NIAEiEDIRV | 137 | 39.21 | 1079 | TLIQqLKEEL | 159 | 10.468 |
| 586 | KLINeKKEKL | 61 | 36.637 | 1128 | TILEtQKVEC | 160 | 10.363 |
| 182 | SLQErLYTKM | 138 | 30.553 | 1487 | AALEiQLKAL | 161 | 10.352 |
| 1043 | QQIEkLQAEV | 139 | 28.912 | 170 | GILPrTLNVL | 162 | 10.249 |
| 870 | KQIVhFQQEL | 55 | 28.807 | | | | |

Start position indicates the number of amino acid from N-terminal of MPHOSPH1. Binding score is derived from "BIMAS" described as Materials and Methods.

TABLE 4A

HLA-A*2402 binding 9-mer peptides derived from DEPDC1

| Start Position | Amino Acid Sequence | SEQ ID NO. | Binding Score | Start Position | Amino Acid Sequence | SEQ ID NO. | Binding Score |
|---|---|---|---|---|---|---|---|
| 295 | YYELFVNIL | 163 | 360 | 505 | KQLCRSQSL | 167 | 14.4 |
| 294 | EYYELFVNI | 12 | 86.4 | 275 | VFRTIADYF | 168 | 14 |
| 282 | YFLDLPEPL | 164 | 43.2 | 36 | HFKKYGNCF | 169 | 12 |

TABLE 4A-continued

HLA-A*2402 binding 9-mer peptides derived from DEPDC1

| Start Position | Amino Acid Sequence | SEQ ID NO. | Binding Score | Start Position | Amino Acid Sequence | SEQ ID NO. | Binding Score |
|---|---|---|---|---|---|---|---|
| 118 | RYPELRKNN | 165 | 21.6 | 307 | GYITVSDRS | 170 | 10.5 |
| 338 | SFKSTECLL | 166 | 20 | 298 | LFVNILGLL | 171 | 42 |

Start position indicates the number of amino acid from N-terminal of DEPDC1. Binding score is derived from "BIMAS" described in Materials and Methods.

TABLE 4B

HLA-A*2402 binding 10-mer peptides derived from DEPDC1

| Start Position | Amino Acid Sequence | SRQ ID NO. | Binding Score | Start Position | Amino Acid Sequence | SRQ ID NO. | Binding Score |
|---|---|---|---|---|---|---|---|
| 294 | EYYElFVNIL | 172 | 288 | 275 | VFRTiADYFL | 182 | 20 |
| 281 | DYFLdLPEPL | 173 | 240 | 113 | KTLPrRYPEL | 183 | 15.84 |
| 118 | RYPElRKNNI | 174 | 216 | 277 | RTIAdYFLDL | 184 | 14.4 |
| 770 | EYPLiYQKRF | 175 | 150 | 270 | GFERdVFRTI | 185 | 12.6 |
| 267 | TYVGfERDVF | 176 | 150 | 146 | RTPKrHGLHL | 186 | 12 |
| 523 | SYINtPVAEI | 177 | 82.5 | 505 | KQLCrSQSLL | 187 | 12 |
| 282 | YFLDlPEPLL | 178 | 36 | 340 | KSTEcLLLSL | 188 | 11.52 |
| 191 | RYVIlIYLQT | 179 | 21 | 295 | YYELfVNILV | 189 | 10.5 |
| 338 | SFKStECLLL | 180 | 20 | 129 | NFSKdKDSIF | 190 | 10 |
| 103 | LFRFpATSPL | 181 | 20 | | | | |

Start position indicates the number of amino acid from N-terminal of DEPDC1. Binding score is derived from "BIMAS" described in Materials and Methods.

TABLE 5A

HLA-A*0201 binding 9-mer peptides derived from DEPDC1

| Start Position | Amino Acid Sequence | SEQ ID NO. | Binding Score | Start Position | Amino Acid Sequence | SEQ ID NO. | Binding Score |
|---|---|---|---|---|---|---|---|
| 674 | FLMDHHQEI | 191 | 728.022 | 563 | RLCKSTIEL | 209 | 21.362 |
| 589 | LLQPHLERV | 192 | 133.255 | 506 | QLCRSQSLL | 210 | 21.362 |
| 575 | SLLPASSML | 193 | 79.041 | 193 | VILIYLQTI | 211 | 20.753 |
| 246 | WVLSAMKCL | 194 | 73.172 | 297 | ELFVNILVV | 212 | 18.201 |
| 619 | LLMRMISRM | 195 | 71.872 | 235 | ILQNKSDDL | 213 | 17.795 |
| 581 | SMLTGTQSL | 196 | 57.085 | 616 | KLQLLMRMI | 214 | 16.797 |
| 290 | LLTFEYYEL | 197 | 54.474 | 623 | MISRMSQNV | 215 | 16.258 |
| 220 | YIMYNMANT | 198 | 40.111 | 72 | TIQLLRKFL | 216 | 16.155 |
| 283 | FLDLPEPLL | 199 | 39.307 | 421 | CSLEGIVDV | 217 | 15.841 |
| 787 | ALFGDKPTI | 200 | 38.601 | 303 | LVVCGYITV | 218 | 15.519 |
| 582 | MLTGTQSLL | 201 | 36.316 | 524 | YINTPVAEI | 219 | 15.177 |
| 773 | LIYQKRFPT | 202 | 32.33 | 194 | ILIYLQTIL | 220 | 14.89 |

TABLE 5A-continued

HLA-A*0201 binding 9-mer peptides derived from DEPDC1

| Start Position | Amino Acid Sequence | SEQ ID NO. | Binding Score | Start Position | Amino Acid Sequence | SEQ ID NO. | Binding Score |
|---|---|---|---|---|---|---|---|
| 114 | TLPRRYPEL | 203 | 32.044 | 239 | KSDDLPHWV | 221 | 14.333 |
| 505 | KQLCRSQSL | 167 | 28.049 | 576 | LLPASSMLT | 222 | 12.668 |
| 765 | KQFQKEYPL | 204 | 28.049 | 646 | MIHTFSRCV | 223 | 12.356 |
| 395 | IMGGSCHNL | 205 | 26.228 | 645 | LMIHTFSRC | 224 | 11.589 |
| 296 | YELFVNILV | 206 | 23.018 | 653 | CVLCCAEEV | 225 | 11.034 |
| 278 | TIADYFLDL | 207 | 22.882 | 297 | ELFVNILGL | 226 | 13.635 |
| 601 | ALQLCCLLL | 208 | 21.362 | | | | |

Start position indicates the number of amino acid from N-terminal of DEPDC1. Binding score is derived from "BIMAS" described in Materials and Methods.

TABLE 5B

HLA-A*0201 binding 10-mer peptides derived from DEPDC1

| Start Position | Amino Acid Sequence | SEQ ID NO. | Binding Score | Start Position | Amino Acid Sequence | SEQ ID NO. | Binding Score |
|---|---|---|---|---|---|---|---|
| 666 | LLAGrLVSFL | 227 | 459.398 | 575 | SLLPaSSMLT | 241 | 27.572 |
| 674 | FLMDhHQEIL | 228 | 299.484 | 296 | YELFvNILVV | 242 | 21.706 |
| 588 | SLLQpHLERV | 229 | 290.025 | 506 | QLCRsQSLLL | 243 | 21.362 |
| 302 | ILVVcGYITV | 230 | 177.358 | 765 | KQFQkEYPLI | 244 | 20.547 |
| 291 | LTFEyYELFV | 231 | 137.017 | 682 | ILQVpSYLQT | 245 | 19.003 |
| 201 | ILGVpSLEEV | 232 | 133.255 | 269 | VGFErDVFRT | 246 | 16.735 |
| 195 | LIYLqTILGV | 233 | 119.657 | 381 | QLVNlRNRRV | 247 | 13.91 |
| 688 | YLQTaVEKHL | 234 | 98.267 | 283 | FLDLpEPLLT | 248 | 13.712 |
| 645 | LMIHtFSRCV | 235 | 64.9 | 395 | IMGGsCHNLI | 249 | 12.809 |
| 581 | SMLTgTQSLL | 236 | 57.085 | 403 | LIGLsNMHDL | 250 | 11.485 |
| 622 | RMISrMSQNV | 237 | 50.232 | 773 | LIYQkRFPTT | 251 | 10.591 |
| 618 | QLLMrMISRM | 238 | 42.278 | 488 | TLTVqDQEEL | 252 | 10.468 |
| 654 | VLCCaEEVDL | 239 | 36.316 | 224 | NMANtSKRGV | 253 | 10.046 |
| 644 | SLMIhTFSRC | 240 | 34.925 | 296 | YELFvNILGL | 254 | 16.26 |
| 505 | KQLCrSQSLL | 187 | 28.049 | 301 | NILGlLQPHL | 255 | 10.868 |

Start position indicates the number of amino acid from N-terminal of DEPDC1. Binding score is derived from "BIMAS" described in Materials and Methods.

Stimulation of the T Cells Using the Predicted Peptides from MPHOSPH1 Restricted with HLA-A*2402

CTLs for those peptides derived from MPHOSHP1 (SEQ ID No: 2) were generated according to the protocols set forth in "Materials and Methods" section above. Resulting CTLs having detectable specific CTL activity, as assessed by IFN-gamma ELISPOT assay, are shown in FIG. 1A and FIG. 2A. In FIG. 1A, the cells in the well number #4 stimulated with MPHOSPH1-A24-9-278 (SEQ ID NO: 7) demonstrated potent IFN-gamma production as compared with the control. In FIG. 2A, the cells in the well number #8 stimulated with MPHOSPH1-A24-10-278 (SEQ ID NO: 8) demonstrated potent IFN-gamma production as compared with the control.

Figures 3A, 3B:
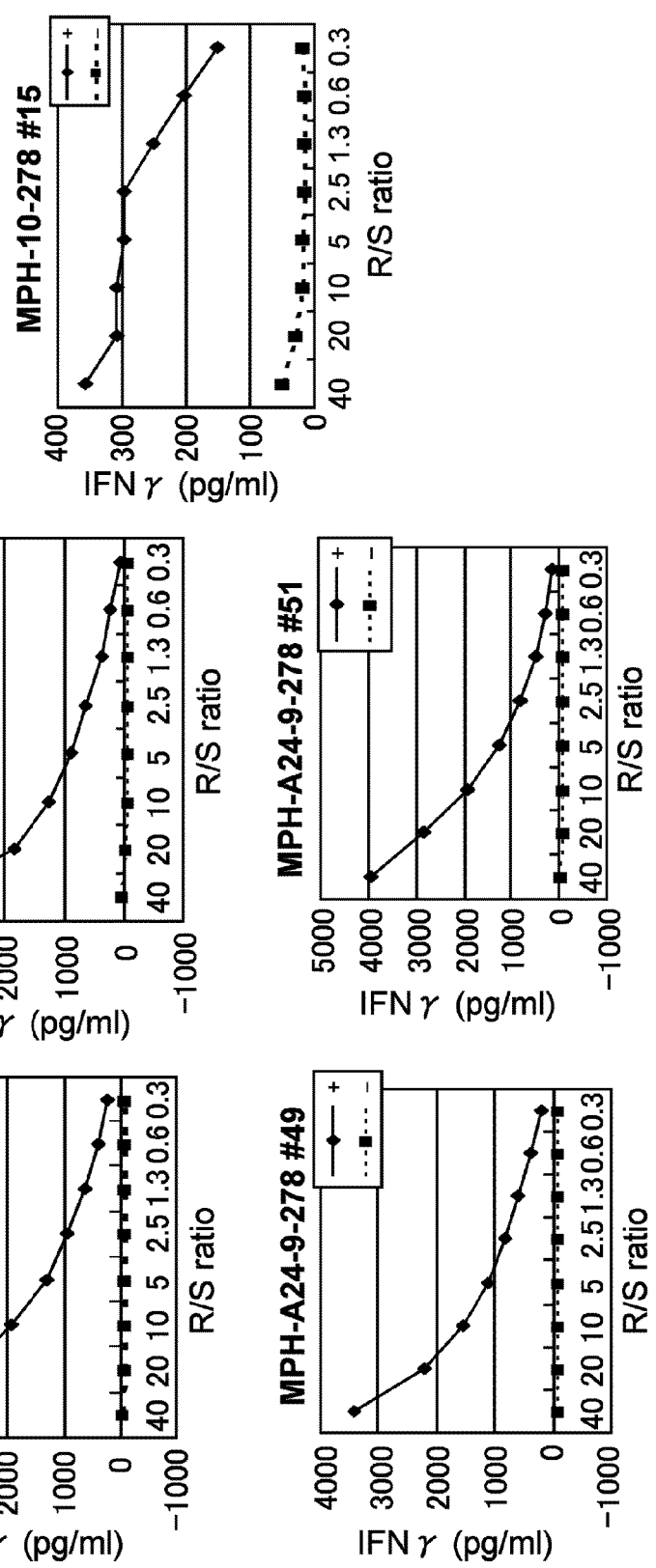
FIG. 3A depicts the establishment of CTL clones stimulated with MPHOSPH1-A24-9-278. (SEQ ID NO: 7). This CTL clone demonstrated high specific CTL activity against target cells (A24LCL) pulsed with MPHOSPH1-A24-9-278, but did not show significant CTL activity against the same target cells (A24LCL) pulsed with no peptides.
FIG. 3B depicts the establishment of CTL clones stimulated with MPHOSPH1-A24-10-278 (SEQ ID NO: 8). This CTL clone demonstrated high specific CTL activity against target cells (A24LCL) pulsed with MPHOSPH1-A24-10-278, whereas it did not show significant CTL activity against the same target cells (A24LCL) pulsed with no peptides.

Next, these cells in the positive well were expanded and limiting dilution was performed. As shown in FIG. 1B (MPHOSPH1-A24-9-278 (SEQ ID NO: 7)) and FIG. 2B (MPHOSPH1-A24-10-278 (SEQ ID NO: 8)), CTL clones having higher specific CTL activities against the peptide-pulsed target as compared to the activities against target without peptide pulse were established The CTL clones stimulated by the MPHOSPH1-A24-9-278 (IYNEYIYDL (SEQ ID NO: 7)) (FIG. 3A) and MPHOSPH1-A24-10-278 (IYNEYIYDLF (SEQ ID NO: 8)) (FIG. 3B) demonstrated potent specific CTL activity against the peptide-pulsed target without showing any significant specific CTL activity against targets not pulsed with any peptide. This suggests that the CTL clone has the peptide-specific cytotoxicity.

Specific CTL Activity Against the Target Cells Expressing MPHOSPH1

The established CTL clones raised against these peptides were examined for their ability to recognize the target cells endogenously expressing MPHOSPH1 and HLA-A*2402. Specific CTL activity against COS7 transfected with both the full length MPHOSPH1 gene and the HLA-A*2402 molecule, which is a specific model for the target cells endogenously express MPHOSPH1 and HLA-A*2402, was tested using as effector cells the CTL clone raised by MPHOSPH1-A24-9-278 (SEQ ID NO: 7). COS7 transfected with full length MPHOSPH1 but not HLA-A*2402 and COS7 transfected HLA-A*2402 but not full length MPHOSPH1 were prepared as controls. The CTL Clone having the highest specific CTL activity against COS7 was that transfected with both MPHOSPH1 and HLA-A24. However, it did not show significant specific CTL activity against COS7 transfected with neither MPHOSPH1 nor HLA-A24 (FIG. 4).

These results clearly demonstrate that MPHOSPH1-A24-9-278 (SEQ ID NO: 7) was naturally expressed to the target cell surface with HLA-A24 molecule and recognized CTL.

CTL Activity Against Bladder Cancer Cell Lines Endogenously Expressing MPHOSPH1

The established CTL clone raised against MPHOSPH1-A24-9-278 (SEQ ID NO: 7) peptide was examined for their ability to recognize the tumor cells endogenously expressing MPHOSPH1. CTL activity against HT1376 cells, which endogenously express MPHOSPH1 and HLA-A24, was tested using the CTL clone raised by MPHOSPH1-A24-9-278 (SEQ ID NO: 7) as effector cells. J82 cells and RT-4 cells were used as the target cells which endogenously express MPHOSPH1 but do not express HLA-A24. The established CTL clone showed high IFN-gamma production against HT1376 cells that express both MPHOSPH1 and HLA-A24. On the other hand, The CTL did not show significant CTL activity against J82 and RT-4 cells which express MPHOSPH1 but not HLA-A24 (FIG. 5). It clearly demonstrated that MPHOSPH1-A24-9-278 (SEQ ID NO: 7) peptide was naturally processed to the tumor cell surface with HLA-A24 molecule and recognized by CTL.

In Vivo CTL Induction with MPHOSPH1-A24-9-278 Peptide in BALB/c Mice

It has been known that H-2Kd molecule, one of the mouse MHC class I, has resemble peptide anchor motif for HLA-A24 molecule and partially cross-react HLA-A24 restricted peptide. The present inventors then examined whether MPHOSPH1-A24-9-278 peptide induce the CTL in vivo by vaccination with this peptide using BALB/c mice (H-2Kd). IFA-conjugated peptide was subcutaneously injected into BALB/c mice on the day 0 and 7. On day 14, splenocytes were harvested and used as the responder cells for ELISPOT assay. Splenocytes of all mice injected peptide (Ani1~5) showed potent IFN-gamma production compared with control mice, which were injected IFA alone (nega1~3) (FIG. 6). This data indicated that MPHOSPH1-A24-9-278 peptide could elicit CTL response even in vivo.

Stimulation of the T Cells Using the Predicted Peptides from MPHOSPH1 Restricted with HLA-A*0201

Resulting CTLs having detectable specific CTL activity, as assessed by IFN-gamma ELISPOT assay, are shown in FIG. 7. As shown in FIG. 7A, the cells in the well number #1 and #5, stimulated with MPHOSPH1-A2-9-282 (YIYDLFVPV (SEQ ID NO: 9)) demonstrated potent IFN-gamma production as compared with the control. As shown in FIG. 7B, the cells in the well number #8 stimulated with MPHOSPH1-A2-9-638 (RLAIFKDLV (SEQ ID NO: 10)) demonstrated potent IFN-gamma production as compared with the control. As shown in FIG. 7C, the cells in the well number #4 stimulated with MPHOSPH1-A2-10-1714 (TMSSsKLSNV (SEQ ID NO: 11)) demonstrated potent IFN-gamma production as compared with the control.

As shown in FIG. 8A (MPHOSPH1-A2-9-282 (SEQ ID NO: 9)), FIG. 8B (MPHOSPH1-A2-9-638 (SEQ ID NO: 10)), and FIG. 8C (MPHOSPH1-A2-10-1714 (SEQ ID NO: 9)), these cells in the positive well were expanded, and CTL lines having higher specific CTL activities against the peptide-pulsed target as compared to the activities against target without peptide pulse were established.

The CTL clones stimulated by the MPHOSPH1-A2-9-282 (YIYDLFVPV (SEQ ID NO: 9)) (FIGS. 9A, and 9B) demonstrated potent specific CTL activity against the peptide-pulsed target without any significant specific CTL activity against targets not pulsed with any peptide.

Stimulation of the T Cells Using the Predicted Peptides from DEPDC1 Restricted with HLA-A*2402

CTLs for those peptides derived from DEPDC1 were generated according to the protocol described in "Materials and Methods" section above. Resulting CTLs having detectable specific CTL activity, as assessed by IFN-gamma ELISPOT assay, are shown in FIG. 10. As shown in FIG. 10A, the cells in the well number #10 stimulated with DEPDC1-A24-9-294 (EYYELFVNI (SEQ ID NO: 12)) demonstrated potent IFN-gamma production as compared with the control. Accordingly, these cells in the positive well were expanded and limiting dilution was performed. As shown in FIG. 10B (DEPDC1-A24-9-294 (SEQ ID NO: 12)), CTL clones having higher specific CTL activities against the peptide-pulsed target compared to the activities against target without peptide pulse were established The CTL clone's stimulated by the DEPDC1-A24-9-294 (EYYELFVNI (SEQ ID NO: 12)) (FIG. 11) demonstrated potent specific CTL activity against the peptide-pulsed target without showing any significant specific CTL activity against targets not pulsed with any peptide. The results suggest that the CTL clone has the peptide-specific cytotoxicity.

Specific CTL Activity Against the Target Cells Expressing DEPDC1 and HLA-A*2402

The established CTL clones raised against these peptides were examined for their ability to recognize the target cells endogenously expressing DEPDC1 and HLA-A*2402. Specific CTL activity against COS7 transfected both with the full length DEPDC1 gene and the HLA-A*2402 molecule, which serves as a specific model for the target cells endogenously express DEPDC1 and HLA-A*2402, was tested using as effector cells the CTL clone raised by DEPDC1-A24-9-294 (EYYELFVNI (SEQ ID NO: 12)). COS7 transfected with full length DEPDC1 but not HLA-A*2402 and COS7 transfected with HLA-A*2402 but not full length DEPDC1 were prepared as controls. The CTL Clone demonstrated high specific CTL activity against COS7 transfected both DEPDC1 and HLA-A24. However, it did not demonstrate significant specific CTL activity against COS7 transfected neither DEPDC1 nor HLA-A24 (FIG. 12).

These results clearly demonstrate that DEPDC1-A24-9-294 (EYYELFVNI (SEQ ID NO: 12)) is naturally expressed to the target cell surface with HLA-A24 molecule and recognized CTL.

CTL Activity Against Bladder Cancer Cell Lines Endogenously Expressing DEPDC1

The established CTL clone raised against DEPDC1-A24-9-294 peptide was examined for their ability to recognize the tumor cells endogenously expressing DEPDC1. CTL activity against HT1376 cells, which endogenously express DEPDC1 and HLA-A24, was tested using the CTL clone raised by DEPDC1-A24-9-294 as effector cells. J82 cells and RT-4 cells were used as the target cells which endogenously express DEPDC1 but do not express HLA-A24. The established CTL clone showed high IFN-gamma production against HT1376 cells that express both DEPDC1 and HLA-A24. On the other hand, it did not show significant CTL activity against J82 and RT-4 cells which express DEPDC1 but not HLA-A24 (FIG. 13). It clearly demonstrated that DEPDC1-A24-9-294 was naturally processed to the tumor cell surface with HLA-A24 molecule and recognized by CTL.

In Vivo CTL Induction with DEPDC1-A24-9-294 Peptide in BALB/c Mice

It has been known that H-2 Kd molecule, one of the mouse MHC class I, has resemble peptide anchor motif for HLA-A24 molecule and partially cross-react HLA-A24 restricted peptide. The present inventors then examined whether DEPDC1-A24-9-294 peptide induce the CTL in vivo by vaccination of this peptide using BALB/c mice (H-2Kd). IFA-conjugated peptide was subcutaneously injected into BALB/c mice on the day 0 and 7. On day 14, splenocytes were harvested and used as the responder cells for ELISPOT assay. Splenocytes of all mice injected peptide (Ani1~5) showed potent IFN-gamma production compared with control mice, which were injected IFA alone (nega1, 2) (FIG. 14). This data indicated that DEPDC1-A24-9-294 peptide could elicit CTL response even in vivo.

Stimulation of the T Cells Using the Predicted Peptides from DEPDC1 Restricted with HLA-A*0201

Resulting CTLs having detectable specific CTL activity when screened by IFN-gamma ELISPOT assay are shown in FIG. 15 and Table 6. The cells in the well number #4 and #7 stimulated with DEPDC1-A02-10-644 ((SLMIHTFSRC SEQ ID NO: 240)) showed potent IFN-gamma production compared with the control. The cells in the well number #2 stimulated with DEPDC1-A02-10-575 (SLLPASSMLT (SEQ ID NO: 241)) showed potent IFN-gamma production compared with the control. The cells in the well number #7 stimulated with DEPDC1-A02-10-506 (QLCRSQSLLL (SEQ ID NO: 243)) showed potent IFN-gamma production compared with the control. The cells in the well number #1 stimulated with DEPDC1-A02-10-765 (KQFQKEYPLI (SEQ ID NO: 244)) showed potent IFN-gamma production compared with the control. The cells in the well number #1 stimulated with DEPDC1-A02-10-395 (IMGGSCHNLI (SEQ ID NO: 249)) showed potent IFN-gamma production compared with the control. The cells in the well number #1 and #2 stimulated with DEPDC1-A02-10-224 (NMANTSKRGV (SEQ ID NO: 253)) showed potent IFN-gamma production compared with the control. The cells in the well number #4 stimulated with DEPDC1-A02-9-297 (ELFVNILGL (SEQ ID NO: 226)) showed potent IFN-gamma production compared with the control. The cells in the well number #3 and #4 stimulated with DEPDC1-A02-10-296 (YELFVNILGL (SEQ ID NO: 254)) showed potent IFN-gamma production compared with the control. The cells in the well number #2, #3, #5 and #7 stimulated with DEPDC1-A02-10-301 (NILGLLQPHL (SEQ ID NO: 255)) showed potent IFN-gamma production compared with the control. The cells in the well number #6 stimulated with DEPDC1-A02-9-598 (LLQPHLERV (SEQ ID NO: 192)) demonstrated potent IFN-gamma production as compared with the control. The cells in the well number #6 stimulated with DEPDC1-A02-9-619 (LLMRMISRM (SEQ ID NO: 195)) demonstrated potent IFN-gamma production as compared with the control. The cells in the well number #2 stimulated with DEPDC1-A02-9-290 (LLTFEYYEL (SEQ ID NO: 197)) demonstrated potent IFN-gamma production as compared with the control. The cells in the well number #5 stimulated with DEPDC1-A02-9-563 (RLCKSTIEL (SEQ ID NO: 209)) demonstrated potent IFN-gamma production as compared with the control. The cells in the well number #1 and #3, stimulated with DEPDC1-A02-9-653 (CVLCCAEEV (SEQ ID NO: 225)), demonstrated potent IFN-gamma production as compared with the control. The cells in the well number #1 stimulated with DEPDC1-A02-10-674 (FLMDhHQEIL (SEQ ID NO: 228)) demonstrated potent IFN-gamma production as compared with the control. Finally, the cells in the well number #2 and #6, stimulated with DEPDC1-A02-10-302 (ILVVcGYITV (SEQ ID NO: 230)), demonstrated potent IFN-gamma production as compared with the control.

The CTL lines stimulated by the DEPDC1-A02-10-296 (YELFVNILGL (SEQ ID NO: 254)) and DEPDC1-A02-9-653 (CVLCCAEEV (SEQ ID NO: 225)) (FIG. 16) showed potent specific CTL activity against the peptide-pulsed target without showing any significant specific CTL activity against targets not pulsed with any peptide. It demonstrates that the CTL clone has the peptide-specific cytotoxicity.

TABLE 6

The candidate peptides from DEPDC1 restricted with HLA-A*0201

| peptide name | SEQ ID No. | Well No. |
| --- | --- | --- |
| DEPDC1-A02-9-589 | 192 | #6 |
| DEPDC1-A02-9-619 | 195 | #6 |
| DEPDC1-A02-9-290 | 197 | #2 |
| DEPDC1-A02-9-563 | 209 | #5 |
| DBPDC1-A02-9-653 | 225 | #1 |
| DEPDC1-A02-9-653 | 225 | #3 |
| DEPDC1-A02-10-674 | 228 | #1 |
| DEPDC1-A02-10-302 | 230 | #2 |
| DEPDC1-A02-10-302 | 230 | #6 |

Specific CTL Activity Against the Target Cells Expressing DEPDC1 and HLA-A*0201

The established CTL lines raised against DEPDC1-A02-10-296 peptide (YELFVNILGL (SEQ ID NO: 254)) and DEPDC1-A02-9-653 (CVLCCAEEV (SEQ ID NO: 225)) were examined for their ability to recognize the target cells endogenously expressing DEPDC1 and HLA-A2. At first, we established HEK293 cell line constitutively expressed HLA-A*0201 (HEK-A2) to efficiently determine specific CTL response. Specific CTL activity against HEK-A2 cells transfected full length of DEPDC I gene, which is specific model for the target cells expressed DEPDC1 and HLA-A2, was tested using the established CTL lines raised by DEPDC1-A02-10-296 (YELFVNILGL (SEQ ID NO: 254)) or DEPDC1-A02-9-653 (CVLCCAEEV (SEQ ID NO: 225)) as effector cells. HEK-A2 transfected Mock expressed vector and HEK-A2 pulsed with no corresponding peptide derived from DEPDC1 were prepared for the negative control. The established CTL lines showed specific CTL activity against HEK-A2 transfected DEPDC1. On the other hand, the CTL lines did not show significant specific CTL activity against HEK-A2 transfected Mock expressed vector and which pulsed DEPDC1-A02-9-674 peptide or DEPDC1-A02-9-462 peptide (FIG. 17). It clearly demonstrated that DEPDC1-A02-10-296 and DEPDC1-A02-9-653 peptide was naturally processed to the target cell surface with HLA-A2 molecule and recognized by CTL.

Homology Analysis of the Antigen Peptides

The CTLs established against peptides of this invention demonstrated potent specific CTL activity. This suggests that the sequences of MPHOSPH1-A24-9-278 (SEQ ID NO: 7), MPHOSPH1-A24-10-278 (SEQ ID NO: 8), MPHOSPH1-A2-9-282 (SEQ ID NO: 9), MPHOSPH1-A2-9-638 (SEQ ID NO: 10), MPHOSPH1-A2-10-1714 (SEQ ID NO: 11), DEPDC1-A24-9-294 (SEQ ID NO: 12), DEPDC1-A2-9-589 (SEQ ID NO: 192), DEPDC1-A2-9-619 (SEQ ID NO: 195), DEPDC1-A2-9-290 (SEQ ID NO: 197), DEPDC1-A2-9-563 (SEQ ID NO: 209), DEPDC1-A2-9-653 (SEQ ID NO: 225), DEPDC1-A2-10-674 (SEQ ID NO: 228), DEPDC1-A2-10-302 (SEQ ID NO: 230) DEPDC1-A02-10-644 (SEQ ID NO: 240), DEPDC1-A02-10-575 (SEQ ID NO: 241), DEPDC1-A02-10-506 (SEQ ID NO: 243), DEPDC1-A02-10-765 (SEQ ID NO: 244), DEPDC1-A02-10-395 (SEQ ID NO: 249), DEPDC1-A02-10-224 (SEQ ID NO: 253), DEPDC1-A02-9-297 (SEQ ID NO: 226), DEPDC1-A02-10-296 (SEQ ID NO: 254) and DEPDC1-A02-10-301 (SEQ ID NO: 255) are homologous to the peptides derived from other molecules, which are known to sensitize human immune system. To exclude this possibility, homology analysis was performed with the peptide sequences as queries using BLAST algorithm (ncbi.nlm.nih.gov/blast/blast.cgi) No significant sequence homology was revealed.

These results suggest that the sequences of MPHOSPH1-A24-9-278 (SEQ ID NO: 7), MPHOSPH1-A24-10-278 (SEQ ID NO: 8), MPHOSPH1-A2-9-282 (SEQ ID NO: 9), MPHOSPH1-A2-9-638 (SEQ ID NO: 10), MPHOSPH1-A2-10-1714 (SEQ ID NO: 11), DEPDC1-A24-9-294 (SEQ ID NO: 12), DEPDC1-A2-9-598 (SEQ ID NO: 192), DEPDC1-A2-9-619 (SEQ ID NO: 195), DEPDC1-A2-9-290 (SEQ ID NO: 197), DEPDC1-A2-9-563 (SEQ ID NO: 209), DEPDC1-A2-9-653 (SEQ ID NO: 225), DEPDC1-A2-10-674 (SEQ ID NO: 228), DEPDC1-A2-10-302 (SEQ ID NO: 230) DEPDC1-A02-10-644 (SEQ ID NO: 240), DEPDC1-A02-10-575 (SEQ ID NO: 241), DEPDC1-A02-10-506 (SEQ ID NO: 243), DEPDC1-A02-10-765 (SEQ ID NO: 244), DEPDC1-A02-10-395 (SEQ ID NO: 249), DEPDC1-A02-10-224 (SEQ ID NO: 253), DEPDC1-A02-9-297 (SEQ ID NO: 226), DEPDC1-A02-10-296 (SEQ ID NO: 254) and DEPDC1-A02-10-301 (SEQ ID NO: 255) are unique and thus possess a low risk of raising unintended immunologic response to any unrelated molecule.

Discussion

Identification of new TAAs, particularly those that induce potent and specific anti-tumor immune responses, warrants further development of the clinical application of peptide vaccination strategies in various types of cancer (Boon T. et al., (1996) J Exp Med 183: 725-9; van der Bruggen P et al., (1991) Science 254: 1643-7; Brichard V et al., (1993) J Exp Med 178: 489-95; Kawakami Y et al., (1994) J Exp Med 180: 347-52; Shichijo S et al., (1998) J Exp Med 187:277-88; Chen Y T et al., (1997) Proc. Natl. Acd. Sci. USA, 94: 1914-8; Harris C C., (1996) J Natl Cancer Inst 88:1442-5; Butterfield L H et al., (1999) Cancer Res 59:3134-42; Vissers J L et al., (1999) Cancer Res 59: 5554-9; van der Burg S H et al., (1996) J. Immunol. 156:3308-14; Tanaka F et al., (1997) Cancer Res 57:4465-8; Fujie T et al., (1999) Int J Cancer 80:169-72; Kikuchi M et al., (1999) Int J Cancer 81: 459-66; Oiso M et al., (1999) Int J Cancer 81:387-94).

cDNA microarray technologies can disclose comprehensive profiles of gene expression of malignant cells (Lin Y M, et al., Oncogene. 2002 Jun. 13; 21:4120-8; Kitahara O, et al., Cancer Res. 2001 May 1; 61:3544-9; Suzuki C, et al., Cancer Res. 2003 Nov. 1; 63:7038-41; Ashida S, Cancer Res. 2004 Sep. 1; 64:5963-72; Ochi K, et al., Int J. Oncol. 2004 March; 24(3):647-55; Kaneta Y, et al., Int J. Oncol. 2003 September; 23:681-91; Obama K, Hepatology. 2005 June; 41:1339-48; Kato T, et al., Cancer Res. 2005 Jul. 1; 65:5638-46; Kitahara O, et al., Neoplasia. 2002 Jul-Aug; 4:295-303; Saito-Hisaminato A et al., DNA Res 2002, 9: 35-45.) and, find utility in the identification of potential TAAs. Among the transcripts that are up-regulated in various cancers, two novel human genes, termed MPHOSPH1 and DEPDC1, respectively, were identified using these technologies.

As demonstrated above, MPHOSPH1 and DEPDC1, are over-expressed in various cancers but show minimal expression in normal tissues. In addition, these genes have been shown to have a significant function related to cell proliferation (See PCT/JP2006/302684). Thus, peptides derived from MPHOSPH1 and DEPDC1 can serve as TAA epitopes, which, in turn, can be used to induce significant and specific immune responses against cancer cells.

Thus, as MPHOSPH1 and DEPDC1 are novel TAAs, vaccines using these epitope peptides find utility as immunotherapeutics against various carcinomas or other disease expressing these molecules.

Example 2

Materials and Methods

Peptides and Adjuvant

The synthesized GMP grade peptides were purchased from Neo Multi Peptide System (MPS) (San Diego, Calif.). As an adjuvant, incomplete Freund's adjuvant (IFA) (MONTANIDE *ISA51) were used. 1 mg of the appropriate peptide was emulsioned with 1 mg of IFA.

Antigen Expression

The present inventors performed immunohistochemical analysis. Tumor cells or tumor tissues from bladder cancers which was obtained from surgery or biopsy was stained by each MPHOSPH1 and DEPDC1-specific polyclonal antibody. Protocol of staining was established in Human Genome Center, Institute for Medical Science, the University of Tokyo as described previously (Kanehira M et al. Cancer Res.; 67(7):3276-3285, 2007, Kanehira M et al. Oncogene. 2007 Apr. 23; [Epub ahead of print]). HLA-A*2402 expression was tested to performed at SRL (Tachikawa, Japan)

Enrolled Patients

Enrolled criteria were as follows;

1. Patients with inoperable recurrent bladder cancer with previously treated with standard chemotherapy and turned to be failure.
2. Patients with performance status 0 or 1 in Japanese Criteria.
3. Patients from 20 years old to 80 years old
4. Patients with primary tumor or metastasis which can be recognized by image inspection (CT/MRI) before treatment, regardless of RECIST guideline
5. Patients with more than 4 weeks after prior treatment (surgery, chemotherapy, radiotherapy, thermotherapy, other immunotherapy etc.)
6. Patients expected more than 3 months prognosis
7. Patients with bone marrow function (WBC more than 2000, 15000 less than, plate more than 50000), liver function (GOT less than 150, GPT less than 150, T-bil less than 3.0), renal function (Cr less than 3.0)
8 Patients with HLA-A*2402
9 Tumor of the patients with expression of MPHOSPH1 and/or DEPDC1

Exclusion criteria were as follows;

1. Patients with pregnant
2. Patients with breast-feeding
3. Patients willing to be made pregnant 4. Patients with uncontrollable infection
5. Patients with necessity of following medicine in the period of clinical trial systemic administration of steroid systemic administration of immunosuppressant
6. Patients who are not thought to be enrolled this trial by doctor or principal investigator Protocol Enrolled bladder cancer patients with HLA-A*2402, whose tumors express M phase phosphoprotein 1 (MPHOSPH1) and/or DEP domain containing 1 (DEPDC1) were immunized with HLA-A*2402-restricted epitope peptides, MPHOSPH1-9-278 (IYNEYIYDL (SEQ ID NO: 7)) and/or DEPDC1-9-294 (EYYELFVNI (SEQ ID NO: 12)). Each peptide was combined with 1 mL of incomplete Freund's adjuvant (IFA, MONTANIDE *ISA51) and was subcutaneously injected into axillary or inguinal lesion once a week. Four times injection is defined as one course, then after 1 course for immunological and clinical evaluation, blood was drawn and CT/MRI was performed.

Evaluation of Safety

Evaluation of adverse effect was performed along with National Cancer Institute-Common Toxicity Criteria version 3, (NCI-CTC ver. 3).

Immunological Evaluation

This is one of secondary endpoint in this study and we confirm whether peptide-specific CTL response occurred or not. Specific CTL response was measure as follows; Peripheral blood mononuclear cells were collected, and re-stimulated by the appropriate peptides. CTL response was tested on the 14th day by IFN-g ELISPOT assay.

Evaluation of Anti-Tumor Effects

Evaluation of clinical response was performed in accordance with RECIST criteria.

Results

Table 7 showed the summary of this clinical trial. There were no severe adverse effects, except Grade 2 of exanthema of Case 3. One minor response (Case 3) and one mixed response (Case 4) were obtained. The expression of MPHOSPH1 was 4 of 5 cases, whereas that of DEPDC1 was 5 of 5 cases, respectively.

Case 3

In case 3, 49 years old male with far advanced bladder cancer in standard chemotherapy failure was enrolled this clinical trial. Only DEPDC1 was expressed strongly (FIG. 20). Therefore, we have vaccinated the epitope peptide derived from DEPDC1 alone. Case 3 had multiple lung metastases of the bladder cancer. In right (FIG. 21) and left (FIG. 22) lobes of lung metastases, the progression rate was decreased after vaccination. Especially, the size of the tumor was decreased after 3rd courses. FIG. 23 showed the anti-tumor effect in accordance with RECIST criteria. It was clarified that the progression rate of metastatic tumor was decreased after vaccination. It indicated that minor response was obtained by vaccination using epitope peptide derived from DEPDC1. In terms of immunological evaluation in case 3, specific CTL response was measured before and after vaccination. Specific CTL response was strongly shown after vaccination (FIG. 24). It clearly indicated that CTL induced by epitope peptide derived from DEPDC1 may show the anti-tumor effect.

Case 4

In case 4, 74 years old male with far advanced bladder cancer in standard chemotherapy failure was enrolled this clinical trial. MPHOSPH1 and DEPDC1 were expressed from his tumor (FIG. 25). Therefore, we have vaccinated two kinds of epitope peptides derived from MPHOSPH1 and DEPDC1. Case 4 had local recurrence of the bladder cancer. After 1 course vaccination, the size of the tumor was reduced 20% in accordance with RECIST criteria (FIG. 26). However, new metastatic lesions in the lung were appeared. It indicated that mixed response was obtained by vaccination using two kinds of epitope peptides derived from MPHOSPH1 and DEPDC1.

Discussion

Rationale of this clinical trial is described blow;
1. Since MPHOSPH1 and DEPDC1 are not expressed in normal tissues except testis, both antigens are highly tumor-specific.
2. These peptides are considered to have strong immunogenicity, since potent and specific CTLs were established by these epitope peptides.

TABLE 7

The summary of this clinical trial

| Case | Age/Gender | Vaccination | Adv. Effect | DTH | Eva. Lesion | Eva. | Present Status | Ag expression MPHOSPH1 | DEPDC1 | CTL |
|---|---|---|---|---|---|---|---|---|---|---|
| 1 | 79/M | 1 course | No | No | LNs, Brain | PD | 1.8 mo, dead | o | o | No |
| 2 | 72/F | in 3 course | No | No | Local Rec | SD (4.5 mo) | 5.0 mo, alive | o | o | NT |
| 3 | 49/M | in 4 course | exanthema | No | Lung Mets | Minor Response | 3.7 mo, alive | x | o | Yes |
| 4 | 74/M | in 2 course | No | No | Local Rec | Minor Response | 1.4 mo, alive | o | o | NT |
| 5 | 78/M | in 2 course | No | No | Local Rec | SD | 1.4 mo, alive | o | o | NT |

NT: not tested

Case 2

In case 2, 72 years old female with far advanced bladder cancer in standard chemotherapy failure was enrolled this clinical trial. In FIG. 18, the antigen expression of her tumor revealed both MPHOSPH1 and DEPDC1 were expressed strongly. Therefore, we have vaccinated two kinds of epitope peptides derived from MPHOSPH1 and DEPDC1. Case 2 had local recurrence of the bladder cancer. It was evaluated stable disease (SD) in accordance with RECIST criteria (FIG. 19).

3. There is 60% of Japanese population with HLA-A*2402.
4. These peptides are chemically stable enough to apply to the clinical trial.

The purpose of this study is to obtain clinical information of its toxicity, immunological response and anti-tumor activity.

Previously reported adverse effects of vaccine clinical trial using peptides are fur-like symptom, such as fever, headache and discomfort. In rare cases, radical skin reaction with blisters, considered as transient cross reactivity at injected site, was reported. In this study, there were no severe adverse effects, except Grade 2 of exanthema of Case 3. This patient had clinical history to show exanthema during chemotherapy. It indicated that this adverse effect did not come from this vaccination, and therefore this protocol may be safe.

Immunological analysis was performed by specific CTL induction after vaccination. In case 1, specific CTL response was not obtained after vaccination (data not shown). In case 3, specific CTL response against DEPDC1 derived peptide was clearly shown after 1$^{st}$ and 2$^{nd}$ course of vaccination. In case 3, anti-tumor effect was obtained by vaccination. It clearly demonstrated that this DEPDC1 derived peptide showed anti-tumor effect against bladder cancer by induction of the specific CTL.

In case 4, after only 1$^{st}$ course of vaccination, anti-tumor effect was clearly obtained against the local recurrence of the bladder cancer. This evidence strongly supports that these epitope peptides show anti-tumor effect against bladder cancer.

In conclusion, it was clarified that this epitope therapy was safe, and furthermore showed strong anti-tumor effect without severe adverse effects.

Industrial Applicability

The present invention identifies new TAAs, particularly those which induce potent and specific anti-tumor immune responses. Such TAAs warrant further development as peptide vaccines against diseases associated with MPHOSPH1 and/or DEPDC1, e.g. cancers.

All patents, patent applications, and publications cited herein are incorporated by reference.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

What is claimed is:

1. An isolated peptide of less than 15 amino acids, wherein the peptide is selected from the group consisting of:
    (a) a peptide comprising the amino acid sequence of SEQ ID NO: 12, and
    (b) a peptide having cytotoxic T cell inducibility, wherein said peptide comprises the amino acid sequence of SEQ ID NO: 12, in which 1 or 2 amino acids are substituted or added;
    wherein,
        (i) the second amino acid from the N-terminus of the amino acid sequence of SEQ ID NO:12 is substituted with phenylalanine, methionine, or tryptophan, or
        (ii) the C-terminal amino acid of the amino acid sequence of SEQ ID NO: 12 is substituted with phenylalanine, leucine, tryptophan, or methionine.

2. The peptide having cytotoxic T cell inducibility of claim 1, wherein the second amino acid from the N-terminus of the amino acid sequence of SEQ ID NO:12 is substituted with phenylalanine, methionine, or tryptophan and the C-terminal amino acid of the amino acid sequence of SEQ ID NO: 12 is substituted with phenylalanine, leucine, tryptophan, or methionine.

3. A method of preparing antigen-presenting cells having a high cytotoxic T cell inducibility, said method comprising the step of contacting an antigen-presenting cell with a peptide of claim 1 or 2.

4. A method of inducing cytotoxic T cells by contacting a T cell with the antigen presenting cell prepared by the method of claim 3.

* * * * *